US008383788B2

(12) United States Patent
Oliviero

(10) Patent No.: US 8,383,788 B2
(45) Date of Patent: Feb. 26, 2013

(54) C-FOS INDUCED GROWTH FACTOR (FIGF) AND DNA ENCODING SAME

(75) Inventor: Salvatore Oliviero, Siena (IT)

(73) Assignee: Vegenics Pty Limited, Toorak, Victoria (AU)

( * ) Notice: Subject to any disclaimer, the term of this patent is extended or adjusted under 35 U.S.C. 154(b) by 1578 days.

(21) Appl. No.: 10/139,876

(22) Filed: May 7, 2002

(65) Prior Publication Data

US 2002/0123481 A1   Sep. 5, 2002

Related U.S. Application Data

(63) Continuation of application No. 09/043,476, filed as application No. PCT/IB96/01113 on Sep. 30, 1996, now abandoned.

(30) Foreign Application Priority Data

Sep. 29, 1995  (GB) ................................. 9519928.7
Jun. 13, 1996  (GB) ................................. 9612368.2

(51) Int. Cl.
| C07H 21/02 | (2006.01) |
| C07H 21/04 | (2006.01) |
| A61K 38/16 | (2006.01) |
| A61K 38/18 | (2006.01) |
| C07K 14/00 | (2006.01) |
| C12N 5/10 | (2006.01) |

(52) U.S. Cl. ..... 536/23.1; 530/380; 514/8.1; 435/365.1; 536/23.51

(58) Field of Classification Search ......................... None
See application file for complete search history.

(56) References Cited

U.S. PATENT DOCUMENTS

| 5,194,596 | A | 3/1993 | Tischer et al. |
| 5,968,778 | A | 10/1999 | Hoppe et al. |
| 6,221,839 | B1 | 4/2001 | Alitalo et al. |
| 6,235,713 | B1 | 5/2001 | Achen et al. |
| 6,383,484 | B1 | 5/2002 | Achen et al. |
| 6,689,580 | B1 | 2/2004 | Achen et al. |
| 6,828,426 | B1 * | 12/2004 | Hirata et al. .................. 530/399 |
| 7,122,654 | B2 | 10/2006 | Achen et al. |
| 7,410,639 | B2 | 8/2008 | Achen et al. |
| 2002/0123481 | A1 | 9/2002 | Oliviero |
| 2003/0166547 | A1 | 9/2003 | Oliviero |
| 2006/0177428 | A1 | 8/2006 | Achen et al. |
| 2008/0145366 | A1 | 6/2008 | Achen et al. |

FOREIGN PATENT DOCUMENTS

| EP | 01 20693 B1 | 5/1989 |
| EP | 01 25023 B1 | 6/1991 |
| EP | 0539748 A1 | 5/1993 |
| EP | 0578909 A1 | 1/1994 |
| EP | 0935001 A1 | 8/1999 |
| EP | 0 935 001 | 11/1999 |
| EP | 0956339 A1 | 11/1999 |
| EP | 1283268 A2 | 2/2003 |
| EP | 0 853 668 B | 3/2005 |
| GB | 9519928.7 | 9/1995 |
| GB | 9612368.2 | 6/1996 |
| JP | 8-185216 | 7/1996 |
| WO | WO-94/02511 A1 | 2/1994 |
| WO | 95/24473 | 9/1995 |
| WO | WO-96/11269 A2 | 4/1996 |
| WO | 9626736 | 9/1996 |
| WO | WO-96/27007 A1 | 9/1996 |
| WO | WO-96/39421 A1 | 12/1996 |
| WO | WO-97/05250 A2 | 2/1997 |
| WO | WO-97/12972 A2 | 4/1997 |
| WO | WO-98/02543 A1 | 1/1998 |
| WO | 98/07832 | 2/1998 |
| WO | WO-98/24811 A2 | 6/1998 |
| WO | 98/36052 | 8/1998 |
| WO | 01/12669 | 2/2001 |

OTHER PUBLICATIONS

Attwood, T.K. The Babel of Bioinformatics. Science 290:471-473, 2000.*
Kyrpides et al. Whole-genome sequence annotation: 'Going wrong with confidence'. Mol. Microbiology 32:886-887, 1999.*
Wells et al. The chemokine information source: Identification and characterization of novel chemokines using the WorldWideWeb and Expressed sequence Tag Databases. J. Leukoc. Biol. 61:545-550, 1997.*
Gerhold et al. It's the genes! EST access to human genome content. BioEssays 18:973-981, 1996.*
Griffin et al. t(11;18)(q21;q21) is a recurrent chromosome abnormality in small lymphocytic lymphoma. Genes, Chromosomes & Cancer 4:153-157, 1992.*
Guo et al. Protein tolerance to random amino acid change. PNAS 101:9205-9210, 2004.*
Angel et al, "The Jun Proto-Oncogene is Positively Autoregulated by Its Product, June/AP-1," *Cell*, 1998, pp. 875-885, vol. 55.
Angel et al., "The Role of Jun, Fos and the AP-1 Complex in Cell-Proliferation and Transformation," *Biochim. Biophys. Acta.*, 1991, pp. 129-157, vol. 1072.
Bauer et al., "Identification of Differentially Expressed mRNA Species by an Improved Display Technique (DDRT-PCT)," *Nucleic Acids Research*, pp. 4272-4280, vol. 21(18).
Bergers et al., "Alternative Promoter Usage of the Fos-Responsive Gene Fit-1 Generates mRNA Isoforms Coding for Either Secreted or Membrane-Bound Proteins Related to the Il-1 Receptor," *EMBO J.*, 1994, pp. 1176-1188, vol. 13.
Brenner et al., "Prolonged Activation of Jun and Collagenase Genes by Tumour Necrosis Factor-α," *Nature*, 1989, pp. 661-663, vol. 337.

(Continued)

*Primary Examiner* — Doug Schultz
(74) *Attorney, Agent, or Firm* — Marshall, Gerstein & Borun LLP

(57) ABSTRACT

A nucleotide molecule encoding a protein encoded by a Fos regulated gene or a fragment thereof, wherein said protein or fragment thereof is encoded by any one of the nucleotide sequences shown in FIG. 1 or 2 or a fragment thereof, including allelic variants and species variants of the nucleotide sequences.

23 Claims, 31 Drawing Sheets

OTHER PUBLICATIONS

Cantor et al., "Ribozyme Cleaves Rex/Tax mRNA and Inhibits Bovine Leukemia Virus Expression," *Proc. Natl. Acad. Sci. USA*, 1993, pp. 10932-10936, vol. 90.

Curran et al., "Structure of the FBJ Murine Osteosarcoma Virus Genome: Molecular Cloning of its Associated Helper Virus and the Cellular Homolog of the v-fos Gene from Mouse and Human Cells," *Mol. Cell. Biol.*, 1983, pp. 914-921, vol. 3.

Distel et al., "Nucleoprotein Complexes that Regulate Gene Expression in Adipocyte Differentiation: Direct Participation of c-Fos," *Cell*, 1987, pp. 835-844, vol. 49.

Farrar et al., "The Molecular Basis of Immune Cytokine Action," *Crit. Rev. Ther. Drug Carrier Syst.*, 1989, pp. 229-261, vol. 5.

Ferrero et al., "An Integrated Physical and Genetic Map of a 35 Mb Region on Chromosome X p22.3-X p21.3," *Human Molecular Genetics*, 1995, pp. 1821-1827, vol. 4.

Gius et al., "Transcriptional Activation and Repression by Fos Are Independent Functions: The C Terminus Represses Immediate-Early Gene Expression Via CArG Elements," *Mol. Cell. Biol.*, 1990, pp. 4243-4255, vol. 10.

Gurney et al., "Opposing Actions of Fos and Jun on Transcription of the Phosphoenolpyruvate Carboxykinase (GTP) Gene," *J. Biol. Chem.*, 1992, pp. 18133-18139, vol. 267.

Hasty et al., "The Role of Stromelysin in the Cartilage Destruction that Accompanies Inflammatory Arthritis," *Arthritis Rheum.*, 1990, pp. 388-397, vol. 33.

Hay et al., "A FOS Protein is Present in a Complex that Binds a Negative Regulator of MYC," *Genes Dev.* 1989, pp. 293-303, vol. 3.

Heuertz et al., "The Gene for Spondyloepiphyseal Dysplasia (SEDL) Maps to Xp22 Between DX16 and DXS92," *Genomics*, 1993, pp. 100-104, vol. 18.

Holt et al., "Inducible Production c-Fos Antisense RNA Inhibits 3T3 Cell Proliferation," *Proc. Natl. Acad. Sci. USA*, 1986, pp. 4794-4798, vol. 83.

Hu et al., "Targeted Disruption of the c-Fos Gene Demonstrates c-Fos-Dependent and Independent Pathways for Gene Expression Stimulated by Growth Factors or Oncogenes," *EMBO J.*, 1994, pp. 3094-3103 vol. 13.

Keck et al., "Vascular Permeability Factor, an Endothelial Cell Mitogen Related to PDGF,"*Science*, 1989, pp. 1309-1311, vol. 246.

Kerr et al., "Growth Factors Regulate Transin Gene Expression by c-Fos-Dependent and c-Fos-Independent Pathways," *Science*, 1988, pp. 1424-1427, vol. 242.

Kim et al., "Inhibition of Vascular Endothelial Growth Factor-Induced Angiogenesis Suppresses Tumour Growth In Vivo," *Nature*, 1993, pp. 841-844, vol. 362.

Kovary et al., "Expression of Different Jun and Fos Proteins During the $G_0$-to-$G_1$ Transition in Mouse Fibroblast: In Vitro and In Vivo Associations," *Mol. Cell. Biol.*, 1991, pp. 2451-2459, vol. 11.

Kovary et al., "The Jun and Fos Protein Families Are Both Required for Cell Cycle Progression in Fibroblasts," *Mol. Cell. Biol.*, 1991, pp. 4466-4472, vol. 11(9).

Leung et al., "Vascular Endothelial Growth Factor is a Secreted Angiogenic Mitogen," *Science*, 1989, pp. 1306-1309, vol. 246.

Liang et al., "Distribution and Cloning of Eukaryotic mRNAs by Means of Differential Display; Refinements and Optimization," *Nucleic Acids Research*, 1993, pp. 3269-3275, vol. 21(14).

Liotta et al., "Metalloproteinases and Cancer Invasion," *Semin. Cancer Biol.*, 1990, pp. 99-106, vol. 1.

Lord et al., "Proto-Oncogenes of the fos/jun Family of Transcription Factors Are Positive Regulators of Myeloid Differentiation," *Mol. Cell. Biol.*, 1993, pp. 841-851, vol. 13(2).

Miller et al., "c-Fos Protein Can Induce Cellular Transfohuation: A Novel Mechanism of Activation of a Cellular Oncogene," *Cell*, 1984, pp. 51-60, vol. 36.

Orlandini et al., "Identification of a c-Fos-Induced Gene That is Related to the Platelet—Derived Growth Factor/Vascular Endothelial Growth Factor Family," *Cell*, 1988, pp. 875-885, vol. 55.

Plate et al., "Up-Regulation of Vascular Endothelial Growth Factor and its Cognate Receptors in a Rat Glioma Model of Tumor Angiogenesis," *Cancer Research*, 1993, pp. 5822-5827, vol. 53.

Riabowol et al., "Microinjection of fos-Specific Antibodies Blocks DNA Synthesis in Fibroblast Cells," *Mol. Cell Biol.*, 1988, pp. 1670-1676, vol. 8.

Rollins et al., "Cloning and Expression of JE, a Gene Inducible by Platelet-Derived Growth Factor and Whose Product Has Cytokine-Like Properties," *Proc. Natl. Acad. Sci.*, 1988, pp. 3738-3742, vol. 85.

Ruther et al., "c-Fos Expression Induces Bone Tumors in Transgenic Mice," *Oncogene*, 1989, pp. 861-865, vol. 4.

Sassone et al., "Transcriptional Autoregulation of the Proto-Oncogene fos," *Nature*, 1988, pp. 314-319, vol. 334.

Schonthal et al., "Requirement for fos Gene Expression in the Transcriptional Activation of Collagenase by Other Oncogenes and Phorbol Esters," *Cell*, 1988, pp. 325-334, vol. 54.

Schusled et al., "Purification, Pharmacological Characterization and Photoaffinity Labeling of Sigma Receptors From Rat and Bovine Brain," *Brain Research*, 1995, pp. 14-28, vol. 670.

Seed et al., "Molecular Cloning of the CD2 Antigen, the T-Cell Erythrocyte Receptor, by a Rapid Immunoselection Procedure," *Proc. Natl. Acad. Sci.*, 1987, pp. 3365-3369, vol. 84.

Superti-Furga et al, "Hormone-Dependent Transcriptional Regulation and Cellular Transformation by Fos-Steroid Receptor Fusion Proteins, " *Proc. Natl. Acad. Sci.*, 1991, pp. 5114-5118, vol. 88.

Takeshtta et al., "Therapeutic Angiogenesis," *J. Clin. Invest.*, 1994, pp. 662-670, vol. 93.

Tsunoda et al., "A Model for Sensitivity Determination of Anticancer Agents Against Chemically-Induced Colon Cancer in Rats," *Anti-Cancer Res.*, 1994, pp. 2637-2642, vol. 14.

Vaziri et al., "Repression of Platelet-Derived Growth Factor-β-Receptor Expression by Mitogenic Growth Factors and Transforming Oncogenes in Murine 3T3 Fibroblasts," *Mol. Cell. Biol.*, 1995, pp. 1244-1253, vol. 15.

Woessner et al., "Role of Metalloproteinases in Human Osteoarthritis," *J. Rheumatol.*, Supp. 1991, pp. 99-101, vol. 27.

Stacker et al., "Biosynthesis of Vascular Endothelial Growth Factor-D Involves Proteolytic Processing Which Generates Non-covalent Homodimers" The Journal of Biological Chemistry, 1999, vol. 274, pp. 32127-32136.

Orlandini et al., "Identification of a c-fos-induced gene that is related to the platelet:derived growth factor/vascular endothelial growth factor family" PNAS, Oct. 1996, vol. 93, pp. 11675-11680.

Yamada Y. et al., "Molecular Cloning of a Novel Vascular Endothelial Growth Factor, VEGF-D" Genomics, 1997, vol. 42, pp. 483-488.

Baldwin M. et al., "The Specificity of Receptor Binding by Vascular Endothelial Growth Factor-D is Different in Mouse and Man" The Journal of Biological Chemistry, 2001, vol. 276, pp. 19166-19171.

Houck, "The Vascular Endothelial Growth Factor Family: Identification of a Fourth Molecular Species and Characterization of Alternative Splicing of RNA" Molecular Endocrinology, 1991, vol. 5, pp. 1809-1814.

Alberts, B. et al., Molecular Biology of the Cell, 1994, p. 237.

Kozak, M., "The Scanning Model for Translation: An Update" The Journal of Cell Biology, 1989, vol. 108, pp. 229-241.

Marconcini, L. et al., "C-fos-induced growth factor/vascular endothelial growth factor D induces angiogenesis in vivo and in vitro" PNAS, Aug. 1999, vol. 96, pp. 9671-9676.

Orlandini, M., et al., "In Fibroblasts VEGF-D Expression is Induced by Cell-Cell Contact Mediated by Cadherin-II" The Journal of Biological Chemistry, 2001, vol. 276, pp. 6576-6581.

Orlandini, M., et al., "[beta]-Catenin Inversely Regulates Vascular Endothelial Growth Factor-D mRNA Stability" The Journal of Biological Chemistry, 2003, vol. 278, pp. 44650-44656.

Rocchigiani, M. et al., "Human FIGF: Cloning, Gene Structure, and Mapping to Chromosome Xp22.1 between the PIGA and the GRPR Genes" Genomics, 1998, vol. 47, pp. 207-216.

Avantaggiato, V. et al., "Embryonic expression pattern of the murine figf gene, a growth factor belonging to platelet-derived growth factor/vascular endothelial growth factor family" Mechanisms of Development, 1998, vol. 73, pp. 221-224.

Vlahakis, N.E. et al., "The Lymphangiogenic Vascular Endothelial the Integrin [alpha] 9 [beta] 1" The Journal of Biological Chemistry, 2005, Growth Factors VEGF-C and -D Are Ligands for vol. 280, pp. 4544-4552.

Young, B.A. et al., "The Cytoplasmic Domain of the Integrin [alpha]9 Subunit Requires the Adaptor Protein Paxillin to Inhibit Cell Spreading but Promotes Cell Migration in a Paxillin independent Manner" Molecular Biology of the Cell, 2001, vol. 12, pp. 3214-3225.
Baldwin, M.E. et al., "Multiple Forms of Mouse Vascular Endothelial Growth Factor-D Are Generated by RNA Splicing and Proteolysis" The Journal of Biological Chemistry, 2001, vol. 276, pp. 44307-44314.
Rissanen, T.T. et al., "VEGF-D is the Strongest Angiogenic and Lymphangiogenic Effector Among VEGFs Delivered Into Skeletal Muscle via Adenoviruses" Circulation Research, 2003, vol. 92, pp. 1098-1106.
Stacker, S.A. et al., "A Mutant Form of Vascular Endothelial Growth Factor (VEGF) That Lacks VEGF Receptor-2 Activation Retains the Ability to Induce Vascular Permeability" The Journal of Biological Chemistry, 1999, vol. 274, pp. 34884-34892.
Achen, M.G. et al., "Monoclonal antibodies to vascular endothelial growth factor-D block its interactions with both VEGF receptor-2 and VEGF receptor-3" Eur.J.Biochem., 2000, vol. 267, pp. 2505-2515.
Zippo, A. et al., "Identification of Flk-1 target genes in vasculogenesis: Pim-I is required for endothelial and mural cell differentiation in vitro" Blood, 2004, vol. 103, pp. 4536-4544.
Salameh, A. et al., "Direct recruitment ofCRK. and GRB2 to VEGFR-3 induces proliferation, migration, and survival of endothelial cells through the activation of ERK., AKT, and JNK. pathways" Blood, 2005, vol. 106, pp. 3424-3431.
Orlandini, M. et al., "Vascular Endothelial Growth Factor-D Activates VEGFR-3 Expressed in Osteoblasts Inducing Their Differentiation" The Journal of Biological Chemistry, 2006, vol. 281, pp. 17961-17967.
Galvagni, F. et al., "Vascular Endothelial Growth Factor Receptor-3 Activity Is Modulated by its Association with Caveolin-I on Endothelial Membrane" Biochemistry, 2007, vol. 46, pp. 398-4005.
Bardelli, M. et al., "VEGF-D is expressed in activated lytnphoid cells and in tumors of hematopoietic and lytnphoid tissues" Leukemia & Lymphoma, 2007, vol. 48, pp. 2014-2021.
Li et al., "PDGF-C is a new protease-activated ligand for the PDGF [alpha]-receptor" Nature Cell Biology, vol. 2, May 2000, p. 302-309.
Albuquerque, et al., "Alternatively spliced vascular endothelial growth factor receptor-2 is an essential endogenous inhibitor of lymphatic vessel growth" Nature Medicine, vol. 15(9), Sep. 2009, p. 1023-1032.
Ahn, et al., "Production of therapeutic proteins with baculovirus expression system in insect cell" Entomological Research, vol. 38, 2008, S71-S78.
Olga Capasso (de Simone & Partners); European Patent Office, Munich, Germany; Re: European Patent Application No. 96 932 771.7-2406; Apr. 1, 2004.
GeneCard entry for Human FIGF/VEGF-D.
Opposition to EP 853668; Further submissions by the Opponent; May 16, 2008; Appendix 1 (Fibroblast assay data relating to Sienna, Experiment with human FIGF/VEGF-D) & Appendix 2 (Fibroblast assay data relating to Sienna, Experiment with Mouse VEGF-D on Fibroblasts).
Keller, G. (Lederer & Keller); Jul. 11, 2008; Re: European Patent Application No. 96.932771.7-2406; Letter to European Opposition Division with attached Annexes A and B.
Vegenics Limited; Opponent's Grounds of Appeal under Article 108 EPC following Opposition to European Patent EP0853668 granted in the name of Universita Degli Studi Di Siena, with attached communication from opponent's representative.
Vegenics Limited; Nov. 30, 2009; Opponent's Reply to Grounds of Appeal filed by the Patentee on May 12, 2009.
Universita Degli Studi Di Siena; Patentee's Grounds of Appeal; Re: European Patent Application No. 96.932771.7-2406, Patent No. 0853668; May 12, 2009, including attached list of documents cited in the Opposition Proceedings.
U.S. Appl. No. 11/397,289 as filed (claiming priority to Japanese Patent Application No. 8-185216).
Christine J. Saoud; Office Action noting allowed claims in U.S. Appl. No. 11/397,289; Oct. 10, 2007.

Declaration of interference between U.S. Appl. No. 11/397,289 and U.S. Appl. No. 11/304,585; Aug. 26, 2009; Patent Interference No. 105,695.
Christine J. Saoud; Restriction Requirement issued in U.S. Appl. No. 10/274,953 (Achen et al.); Apr. 14, 2005.
Letter dated Jun. 4, 2010 from Attorney Gass representing unnamed third party.
Letter dated Sep. 4, 2010 from Attorney Gass representing unnamed third party.
Letter dated Sep. 1, 2010 from Robert Stephen/Olswang firm to the European Patent Office in relation to T0591/09, opposition of EP 0853668.
Declaration of Salvatore Oliviero dated Feb. 2, 2010.
EP Description relating to Figure 3 compared to US Exhibit 2C.
Letter to European Patent Office dated Apr. 1, 2004.
GeneCards search results retrieved May 26, 2010.
Aachen, Vascular endothelial growth factor D (VEGF-D) is a ligand for the tyrosine kinases VEGF receptor 2 (Flkl) and VEGF receptor 3 (Flt4), Proc. Natl. Acad. Sci. USA 95:548-553, 1998.
Claims as presently in contention in opposition for EP 0853668B.
*Goeddel* v. *Sugano*, 617 F.3d. 1350 (Fed. Cir. Sept 7, 2010) (Reversing decision of United States Patent and Trademark Office, Board of Patent Appeals and Interferences, Interferences No. 105,334 and 105,337).
"List of Motions" filed on behalf of Vegenics Pty Limited in Patent Interference No. 105,845 (RT), *Vegenics Pty Limited* (U.S. Patent No. 6,689,580) v. *University Degli Studi di Siena* (U.S. Appl. No. 10/139,876, filed Oct. 18, 2011).
Achen et al., "The Non-receptor Tyrosine Kinase Lyn is Localised in the Developing Murine Blood-brain Barrier," *Differentiation*, 59:15-24 (1995).
Andersson et al., "Involvement of Loop 2 of Platelet-derived Growth Factor-AA and -BB in Receptor Binding," *Growth Factors*, 12:159-164 (1995).
Andersson et al., "Assignment of Interchain Disulfide Bonds in Platelet-derived Growth Factor (PDGF) and Evidence for Agonist Activity of Monomeric PDGF," *J. Biol. Chem.*, 267:11260-11266 (1992).
Aruffo et al., "Molecular Cloning of a CD28 cDNA by a High-efficiency COS Cell Expression System," *PNAS*, 84:8573-8577 (1987).
Cao et al., "gro-$\beta$, a -C-X-C- Chemokine, is an Angiogenesis Inhibitor that Suppresses the Growth of Lewis Lung Carcinoma in Mice," *J. Exp. Med.*, 182:2069-2077 (1995).
Claffey et al., "Structural Requirements for Dimerization, Glycosylation, Secretion, and Biological Function of VPF/VEGF," *Biochim. Biophys. Acta.*, 1246:1-9 (1995).
Dignam et al., "Balbiani Ring 3 in *Chironomus tentans* Encodes a 185-kDa Secretory Protein which is Synthesized Throughout the Fourth Larval Instar," *Gene*, 88:133-140 (1990).
Ferrara et al., "The Vascular Endothelial Growth Factor Family of Polypeptides," *J. Cell. Biochem.*, 47:211-218 (1991).
Vassbotn et al., "Reversion of Autocrine Transformation by a Dominant Negative Platelet-Derived Growth Factor Mutant," *Mol. Cell Biol.*, 13:4066-4076 (1993).
Folkman et al., "Angiogenesis," *J. Biol. Chem.*, 267:10931-10934 (1992).
Gospodarowicz et al., "Isolation and Characterization of a Vascular Endothelial Cell Mitogen Produced by Pituitary-derived Folliculo Stellate Cells," *PNAS*, 86:7311-7315 (1989).
Haefliger et al., "Four Novel Members of the Connexin Family of Gap Junction Proteins," *J. Biol. Chem.*, 267:2057-2064 (1992).
Hatva et al., "Vascular Growth Factors and Receptors in Capillary Hemangioblastomas and Hemangiopericytomas," *Am. J Pathol.*, 148(3):763-775 (1996).
Hillier et al., GenBank Accession No. H24828 (1995).
Holloway et al., "Chromosomal Mapping of Five Highly Conserved Murine Homologues of the *Drosophila* RING Finger Gene *Seven-in-absentia*," *Genomics*, 41:160-168 (1997).
Houck et al., "Dual Regulation of Vascular Endothelial Growth Factor Bioavailability by Genetic and Proteolytic Mechanisms," *J. Biol. Chem.*, 267(36):26031-26037 (1992).

Jenkins et al., "Organization, Distribution, and Stability of Endogenous Ecotropic Murine Leukemia Virus DNA Sequences in Chromosomes of *Mus musculus*," *J. Virol.*, 43:26-36 (1992).

Joukov et al., "A Novel Vascular Endothelial Growth Factor, VEGF-C, is a Ligand for the Flt4 (VEGFR-3) and KDR (VEGFR-2) Receptor Tyrosine Kinases," *EMBO J.*, 15:290-298 (1996).

Kaipainen et al., "Enhanced Expression of the Tie Receptor Tyrosine Kinase Messenger RNA in the Vascular Endothelium of Metastatic Melanomas," *Cancer Res.*, 54:6571-6577 (1994).

Kaipainen et al., "Expression of the Fms-like Tyrosine Kinase 4 Gene Becomes Restricted to Lymphatic Endothelium During Development," *PNAS*, 92:3566-3570 (1995).

Kim et al., "The Vascular Endothelial Growth Factor Proteins: Identification of Biologically Relevant Regions by Neutralizing Monoclonal Antibodies," *Growth Factors*, 7:53-64 (1992).

Montesano et al., "Basic Fibroblast Growth Factor Induces Angiogenesis in Vitro," *PNAS*, 83:7297-7301 (1986).

Oefner et al., "Crystal Structure of Human Platelet-derived Growth Factor BB," *EMBO J.*, 11:3931-3926 (1992).

Oelrichs et al., "*NYK/FLK*-1: A Putative Receptor Protein Tyrosine Kinase Isolated from E10 Embryonic Neuroepithelium is Expressed in Endothelial Cells of the Developing Embryo," *Oncogene*, 8:11-18 (1993).

Ostman et al., "Identification of Three Amino Acids is the Platelet-derived Growth Factor (PDGF) B-chain that are Important for Binding to the PDGR β-Receptor," *J. Biol. Chem.*, 266:10073-10077 (1991).

Olofsson et al., "Vascular Endothelial Growth Factor B, a Novel Growth Factor for Endothelial Cells" *PNAS*, 93:2576-2581 (1996).

Patil et al., "DNA-based Therapeutics and DNA Delivery Systems: A Comprehensive Review," *AAPS Journal*, 17:E61-E77 (2005).

Paulsson et al., "The Balbiani Ring 3 Gene in *Chironomus tentans* has a Diverged Repetitive Structure Split by Many Introns," *J. Mol. Biol.*, 211:331-349 (1990).

Plate et al., "Angiogenesis in Malignant Gliomas," *GLIA*, 15(3):339-347 (1995).

Potgens et al., "Covalent Dimerization of Vascular Permeability Factor/Vascular Endothelial Growth Factor is Essential for its Biological Activity," *J. Biol. Chem.*, 269:32879-32885 (1994).

Rastinejad et al., "Regulation of the Activity of a New Inhibitor of Angiogenesis by a Cancer Suppressor Gene," *Cell*, 56:345-355 (1989).

Sambrook et al., *Molecular Cloning: A Laboratory Manual*, 2nd Ed, Cold Spring Harbor Laboratory, Cold Spring Harbor, New York (1989).

Sanger et al., "DNA Sequencing with Chain-terminating Inhibitors," *PNAS*, 74:5463-5467 (1977).

Strawn et al., "Flk-1 as a Target for Tumor Growth Inhibition," *Cancer Res.*, 56:3540-3545 (1996).

Tischer et al., "Vascular Endothelial Growth Factor: A New Member of the Platelet-derived Growth Factor Gene Family," *Biochem. Biophys. Res. Comm.*, 163:1198-1206 (1989).

\* cited by examiner

FIG. 1

```
        10                  30                  50
         .         .         .         .         .
ggaagatatgaccacctcctgattattttgcagcggggaaactttgaaatattttcatt 70                  90                 110
         .         .         .         .         .
gctttctcccatactaagattgtgtgtgaggcagtgagggagtccctgacttactcaag 130                 150                 170
         .         .         .         .         .
tcatttcattggatttttaattacaactgatcatgtgattgttttttccatgtaaagttt 190                 210                 230
         .         .         .         .         .
ggggcttcaaactttgcttctctggagaatgccttttgcaaacacttttcagtagctgcctgg 250                 270                 290
         .         .         .         .         .
aaacaactgcttagtcatcgtagacattaaaatattcaaaatgtatggagaatggga
                                          M Y G E W G
```

FIG. 1(I)

```
         310                330                350
atgggaatatcctcatgatgttccatgtgtacttggtgcagggcttcaggagcgaacat
 M  G  N  I  L  M  M  F  H  V  V  Y  L  V  Q  G  F  R  S  E  H 370                390                410
ggaccagtgaaggattttctttgagcgatcatcccgtccatgttgaacgatctga
 G  P  V  K  D  F  F  S  F  E  R  S  S  R  S  M  L  R  R  S  E 430                450                470
caacagatccgagcagcttctagtttggaggagttgctgcaaatcgcgcactctgaggac
 Q  Q  I  R  A  A  S  S  L  E  E  L  L  Q  I  A  H  S  E  D
```

FIG. 1(II)

```
                                490                        510                        530
tggaagctgtggcgatgcgccgtgttgaagctcaaaagtcttgccagtatggactcacgctca
 W  K  L  W  R  C  R  L  K  L  K  S  L  A  S  M  D  S  R  S 550                        570                        590
gcatcccatcgctccaccagatttgcggcaactttctatgacactgaaacactaaaagtt
 A  S  H  R  S  T  R  F  A  A  T  F  Y  D  T  E  T  L  K  V 610                        630                        650
atagatgaagaatggcagagaccaatgcagccctagagagacatgcgtagaagtcgcc
 I  D  E  E  W  Q  R  T  Q  C  S  P  R  R  E  T  C  V  R  V  A 670                        690                        710
agtgagctggggggaagacaacaaacacattcttcaagcccccctgtgtaatgtcttccgg
 S  E  L  G  G  R  T  T  N  T  F  F  K  P  P  C  V  N  V  F  R
```

FIG. 1(III)

```
                        730                 750                 770
tgtggaggctgctgcaacgaagaagagggtgtgatgtgtatgaacacaagaacttcctactatc
 C  G  G  C  C  N  E  E  G  V  M  C  M  N  T  S  Y  I 790                 810                 830
tccaaacagctctttgagatatcagtgcctctgacatcagtgccgagttagtgcctgtt
 S  K  Q  L  F  E  I  S  V  P  L  T  S  V  P  E  L  V  P  V 850                 870                 890
aaaattgccaaccatacgggttgtaagtgcttgccacgggcccccgccatccttactca
 K  I  A  N  H  T  G  C  K  C  L  P  T  G  P  R  H  P  Y  S 910                 930                 950
attatcagaagatccattcagaccccagaagaagatgaatgtcctcattccaagaaactc
 I  I  R  R  S  I  Q  T  P  R  R  D  E  C  P  H  S  K  K  L 970                 990                 1010
tgtcctattgacatgctgtgggataacaccaaatgtaaatgtgttttgcaagacgagact
 C  P  I  D  M  L  W  D  N  T  K  C  K  C  V  L  Q  D  E  T
```

FIG. 1(IV)

```
                       1030                       1050                       1070
                        .                          .                          .
ccactgcctgggacagaagaccactcttacctccaggaacccactctctgtgaccgcac
 P   L   P   G   T   R   D   H   S   Y   L   Q   E   P   T   L   C   G   P   H 1090                       1110                       1130
                        .                          .                          .
atgacgtttgatgaagatcgctgtgagtgcgtctgtaaagcaccatgtccggagatctc
 M   T   F   D   E   D   R   C   E   C   V   C   K   A   P   C   P   G   D   L 1150                       1170                       1190
                        .                          .                          .
attcagcacccggaaaactgcagttgctttgagtgcaaagaaagtctggagagctgtgc
 I   Q   H   P   E   N   C   S   C   F   E   C   K   E   S   L   E   S   C   C 1210                       1230                       1250
                        .                          .                          .
caaaagcacaagattttcacccagacacctgcagtgaggacagatgtccttttcac
 Q   K   H   K   I   F   H   P   D   T   C   S   E   D   R   C   P   F   H 1270                       1290                       1310
                        .                          .                          .
accagaacatgtgcaagtagaaagccagcctgtggaaagcactggcgctttccaaggag
 T   R   T   C   A   S   R   K   P   A   C   G   K   H   W   R   F   P   K   E
```

FIG. 1(v)

```
            1330                  1350                  1370
              .                     .                     .
acaagggcccagggactctacagccaggagaacccttgattcaacttccttcaagtccc
 T  R  A  Q  G  L  Y  S  Q  E  N  P 1390                  1410                  1430
              .                     .                     .
cccatctctgtcattttaaacagctcactgctttgtcaagttgctgtcactgttgcccac 1450                  1470                  1490
              .                     .                     .
tacccctgccccccctcccgcctccagtgttagaaaagttgatttgacctagtgt 1510                  1530                  1550
              .                     .                     .
catggtaaagccacatttccatgcaatgggctaggtgattcccagtcactgacaaa 1570                  1590                  1610
              .                     .                     .
tgacttgtagcttcagatgtctttgcgccatcagcactcagaaaggaagggtctgagga
```

```
1630                    1650                    1670
gcccccttgtgttttgatgaataagaaaaaggttgcctgaaacagagtagtaggtgccactcga 1690                    1710                    1730
ttggttcctcggcctggcaaagtccaaggggcaatgctcatgagttattgtgctctttct 1750                    1770                    1790
tatgcggaatttcatttgtatgatcagcactgatcaattccacttgtactttt 1810                    1830                    1850
aggtttactgaagcactgcctgatgtttatgtaaatgtatttaaggaaataaacac 1870                    1890
tgtttatgcagccccacaaaaaaaaaaaaaaaa
```

```
1   GGCACGAGGTTTTTTTTTTTTTCATCTCTCCCACCCCTAAGATTGTGAAA   60
    ----+----+----+----+----+----+----+----+----+----+
    CCGTGCTCCAAAAAAAAAAAAAGTAGAGAGGGTGGGGATTCTAACACGTTT

G  T  R  F  F  F  F  F  I  S  L  S  P  P  L  R  L  C  K  -
     A  R  G  F  F  F  F  F  S  G  L  S  P  H  P  *  D  C  A  K
      H  E  V  F  F  F  F  F  H  L  S  L  P  T  P  K  I  V  Q  K

61  AAAAGGCGTACCCTTGCCTAATTGAAATAATTTCATTGGATTTGATCAGAACTGATTATTT  120
    ----+----+----+----+----+----+----+----+----+----+
    TTTTCGCATGGAACGGATTAACTTTATTAAAGTAACCTAAACTAGTCTTGACTAATAAA

K  S  V  P  C  L  I  E  I  I  S  L  D  F  D  Q  N  *  L  F  -
     K  A  Y  L  A  *  L  K  *  F  H  W  I  L  I  R  T  D  Y  L  -
      K  R  T  L  P  N  *  N  N  F  I  G  F  *  S  E  L  I  I  W  -

121 GGTTTCTGTGTGAAGTTTGAGGTTTCAAACTTTCCTTCTCTGGAGAATGCCTTTTGAAAC  180
    ----+----+----+----+----+----+----+----+----+----+
    CCAAAAGACACACTTCAAACTCCAAAGTTTGAAAGGAAGAGACCTCTTACGGAAAACTTTG
```

FIG. 2(I)

```
       G  F  L   C  E  V  L   R  F  Q  T  F  L  L  E  N  A  F  *  N
        V  F  C   V  K  P  *   G  F  K  L  S  F  W  R  M  P  F  E  T
         F  S  V   *  S  F  E   V  S  N  F  P  S  G  E  C  L  L  K  Q
     AATTTCTAGCTGCCTGAGTGTCAAGTAATCAGTGGATATTGAAATATTCAA
181  --------+---------+---------+---------+---------+  240
     TTAAAGATCGACGGACTCACAGTTCATTAGTCACCTATAACTTTATAAGTT

N  F  L  *   L  P  D  V  N  C  L  V   I  S  G  Y  *   N  I  Q
        I  F  S  S   C  L  M  S  T  A  *  *    S  V  D  I  E  I  F  K
         F  S  L  A   A  *  C  Q  L  L  S  N   Q  W  I  L  K  Y  S  K
     AATGTACAGAGAGTGGTAGTGGGTAGTGAATGTTTCATGATGTGTACGTTCCAGTGGTGCA
241  --------+---------+---------+---------+---------+  300
     TTACATGTCTCTCACCATCACCCATCACTTACAAAGTACTACACATGCAGGTCACCACGT

```
     GGGCTTCCAGTAATGAACATGAACCAGTGAGCCATCATTCAGTCTTCAGTCCACATTGGAACGATC
301  ------+---------+---------+---------+---------+---------+---------+  360
     CCCGAGGTCATTACTTGTACTGGTCACTCGGTAGTAAGTCAGAAGTCAGGTGTAACCTTGCTAG

G  L  Q  *  T  W  T  S  E  A  I  I  S  V  H  I  G  I  I
       G  S  S  N  E  H  G  P  V  K  R  S  Q  S  T  L  E  R  S
         A  P  V  M  M  D  Q  *  S  D  H  S  P  E  W  N  D  L

TGAACAGCAGATCAGGGCTCCTGGTTTGAGTTCTAGTTTGCTAGTTTCTAGTTCTAGTTCGAATTACTCACTCTGA
361  ------+---------+---------+---------+---------+---------+---------+  420
     ACTTGTCGTCTAGTCCCGAGGAGATCAAACCTCGAAGATCAAACGATCAAGCTTAATGAGTGAGACT

*  T  A  D  Q  G  C  E  *  F  G  G  T  L  S  N  Y  S  L  *
       E  Q  Q  I  R  A  A  S  L  E  E  L  L  R  I  T  H  S  E
         N  S  R  S  G  L  L  L  V  W  R  N  Y  F  E  L  L  T  L  R

GCACTCGGAAGCTGTCCGACATGCAGGCTCGAGGCTCAAAGTTTTACCAGTATGGACTCTCG
```

FIG. 2(III)

```
        L  E  A  V  E  M  Q  A  E  A  Q  K  F  Y  Q  Y  G  L  S
        D  W  K  L  W  R  C  R  L  R  K  S  F  T  S  M  D  S  R
        T  G  S  C  G  D  A  G  *  G  S  K  V  L  P  V  W  T  L  A
421 ----+---------+---------+---------+---------+---------+---------+ 480
    CCTGACCTTCGACACCTCTAGTCCGAGTCCGAGTTTCAAAATGGTCATACCTGAGAGC

L  S  I  P  S  V  H  *  V  C  G  N  F  L  *  H  *  N  T  K
        S  A  S  H  R  S  T  R  F  A  A  T  F  Y  D  I  E  T  L  K
        Q  H  P  I  G  P  L  G  L  R  Q  L  S  M  T  L  K  H  *  K
481 ----+---------+---------+---------+---------+---------+---------+ 540
    CTCAGCATCCATCGGTCCAACTTCTATGACATTGAAACACTAAA
    GAGTCGTAGGGTAGCCAGGTGATCAAACGCCGTTGAAGATACTGTAACTTTGTGATTT

S  Y  R  *  R  M  A  K  N  S  V  Q  P  *  R  N  V  R  G  G
        V  I  D  E  E  W  Q  R  T  Q  C  S  P  R  E  T  C  V  E  V
        L  *  M  K  N  G  K  E  L  S  A  A  L  E  K  R  A  W  R  W
541 ----+---------+---------+---------+---------+---------+---------+ 600
    AGTTATAGATGAAGAATGGCAAAGAACTCAGTGCAGCCCTAGAGAAACGTGCGTGGAGGT
    TCAATATCTACTTCTTACCGTTTCTTGAGTCACGTCGGGATCTCTTTGCACGCACCTCCA
```

FIG. 2(iv)

```
        G  Q  *  A  G  E  E  Y  Q  H  I  L  L  O  A  P  L  C  E  R  V
           A  S  E  L  G  K  S  T  N  T  F  F  K  P  P  C  V  N  F
     GGCCAGTGAGCTGGGAAGAGTACCAACACATTCTTCAAGCCCCCTGTGTGAACGTGTT
601  ------+---------+---------+---------+---------+---------+  660
     CCGGTCACTCGACCCTTCTCATGGTTGTGTAAGAAGTTCGGGGGACACACTTGCACAA
           P  V  S  W  G  R  V  P  T  H  S  S  P  L  V  *  T  C  S

P  M  W  L  L  O  *  R  E  L  Y  V  Y  E  H  Q  H  L  V
           R  C  G  G  C  N  E  E  S  F  M  C  M  N  T  S  T  S  Y
     CCGATGTGGTGGtTGTTGCAATGAAGAGTCCTTTATGTGTATGAACACCAGCACCTCGTA
661  ------+---------+---------+---------+---------+---------+  720
     GGCTACACCACCAACAACGTTACTTCTCGAAATACACATACTTGTGGTCGTGGAGCAT
           D  V  V  V  A  M  K  R  A  L  C  V  *  T  P  A  P  R  T

H  F  Q  T  A  L  *  D  I  S  A  F  D  I  S  T  *  L  B  A
           L  S  K  Q  L  F  E  I  S  V  P  L  T  S  V  P  E  L  V  P
     CATTTCCAAACAGCTCTCTTTGAGAATATCAGTGCCTTTGACATCAGTACCTGAATTAGTGCC
721  ------+---------+---------+---------+---------+---------+  780
     GTAAAGGTTTGTCGAGAGAAACTCTATAGTCACGGAAACTGTAGTCATGGACTTAATCACGG
           F  P  N  S  S  L  R  Y  Q  C  L  *  H  Q  Y  L  N  *  C  L
```

FIG. 2(v)

```
      TGTTAAAGTTGCCAATCATACAGGTTGTAAGTGCTTGCCAACAGCCCCCGCCATCCATA
781   ---------+---------+---------+---------+---------+---------+  840
      ACAATTTCAACGGTTAGTATGTCCAACATTCACGAACGGTTGTCGGGGGCGGTAGGTAT

C  *  S  C  Q  S  Y  R  L  *  V  L  A  N  S  P  P  S  I  -
        V  K  V  A  N  H  T  G  C  K  C  L  P  T  A  P  R  H  P  Y
         L  K  L  P  I  I  Q  V  V  S  A  C  Q  Q  P  P  A  I  H  T

CTCAATTATCAGAAGATCCATCCAGATCCCTGAAGAAGATCGCTGTTCCCATTCCAAGAA
841   ---------+---------+---------+---------+---------+---------+  900
      GAGTTAATAGTCTTCTAGGTAGGTCTAGGGACTTCTTCTAGCGACAAGGGTAAGGTTCTT

L  N  Y  Q  K  I  H  P  D  D  P  *  R  R  S  L  F  P  F  Q  E  -
        S  I  I  R  R  S  I  Q  I  P  E  E  D  R  C  S  H  S  K  K  -
         Q  L  S  E  D  P  S  R  S  L  K  K  I  A  V  P  I  P  R  N  -

ACTCTCTCCTATTCACATGCTATGGGATACCAACAAATGTAAATGTGTTTTGCAGGAGGA
```

FIG. 2(vi)

FIG. 2(vii)

```
      TCTTAATCCAGCACCCAAAACTGCAGTTGCTTGAGTGCAAAGAAAAGTCTGAAGACCTG
1082  ----+----+----+----+----+----+----+----+----+----+----+----  1140
      AGATTAGGTCGTGGGTTTTGACGTCAACGAACTCACGTTTCTTTCAGACTTCTGGAC

S N P A P Q K L Q L L *  V Q R K S G D L
                L I Q H P K N C S   F E C K E K S L E T C
                  * S T P K T A V A   L K R R V W R P A

CTGCCCGAAGCAACAGCTATTTCACCCAGACCTGTGCGAGGACACAGCCCCCTTT
1141  ----+----+----+----+----+----+----+----+----+----+----+----  1200
      GACGGGCTTCGTTGTCGATAAAGTGGGTCTGGACACGCTCCTGTGTCGGGGGAA

L P E A Q A I S P R E L Q L L *  G Q M P L
              C Q K H K L F H P D T C S E D R C P F
                A R S T S Y F T Q T P A A V R T D A P

TCATATACCAGACCATGTGCAAGTGGCAAAACAGCATGTGCAAAGCATTGCCGCTTTCCAAA
1201  ----+----+----+----+----+----+----+----+----+----+----+----  1260
      AGTATATGGTCTGGTACACGTTCACCGTTTTGTCGTACACGTTTCGTAACGGCGAAAGGTTT

S Y Q T M C K W Q N S M C K A L P L S K
                H T R P C A S G K T A C A K H C R F P M
                  I P D H V Q V A K Q H V Q S I A A F Q R
```

FIG. 2(VIII)

```
1261  GGAGAAAAGGGCTGCCCAGGGCCCCAGCCCCAGAAGGAGAATCCTTGAATTCAGCGTTCCAAG
      ----+----+----+----+----+----+----+----+----+----+----+----+  1320
      CCTCTTTTCCCGACGGGTCCCGGGGTCGGGGTCTTCCTCTTAGGAACTTAAGTCGCAAGGTTC

G  E  K  G  C  P  G  A  P  Q  P  K  E  S  L  I  Q  R  S  K
         E  K  R  A  A  Q  G  P  H  S  R  K  N  P  *  F  S  V  P  S
          R  K  G  L  P  R  G  P  T  A  E  R  I  L  D  S  A  F  Q  V

1321  TTCCCATCCCTGTCATTTTAAACAGCATGCTCTGCCAAGTGCTGTCACTGTTTT
      ----+----+----+----+----+----+----+----+----+----+----+----+  1380
      AAGGGTAGGGACAGTAAAATTTGTCGTACGAGACGGTTCACGACAGTGACAAAA

F  P  I  P  V  I  F  N  S  M  L  C  Q  V  A  V  T  V  F
         S  P  S  L  S  F  L  T  A  C  C  F  A  K  L  L  S  L  F  F
          P  H  P  C  H  F  *  Q  H  A  A  L  P  S  C  C  H  C  F  F

TTCCAGCTGTTAAAAAAAAAAAATCCATTTTACACAGCACCACCAGTGAATCCAGACCAACC
      ----+----+----+----+----+----+----+----+----+----+----+----+
```

FIG. 2(IX)

```
1381 -----+---------+---------+---------+---------+---------+ 1440
     AAGGGTCCACAATTTTTTTAGGTAAATGTGTCGTGGTGTCACTTAGTCGTTGG
     F  P  G  V  K  K  K  I  E  F  T  Q  H  H  S  E  S  R  P  T  -
      S  Q  V  L  K  K  K  S  I  L  H  S  T  T  V  N  P  D  Q  P  -
       P  R  C  *  K  K  N  P  F  Y  T  A  P  Q  *  I  Q  T  N  L  -

TTCCATTCACACCAGCTAAGGAGTCCCTGGTTCATTGATGGATGTCTTCTAGCTGCAGAT
1441 -----+---------+---------+---------+---------+---------+ 1500
     AAGGTAAGTGTGGTCGATTCCTCAGGGACCAAGTAACTACCTACAGAAGATCGACGTCTA
     F  H  S  H  Q  L  R  S  P  W  F  I  D  G  C  L  L  A  A  D  -
      S  I  H  T  S  *  G  V  P  G  S  L  M  D  V  F  *  L  Q  M  -
       P  F  T  P  A  K  E  S  L  V  H  *  W  M  S  S  S  C  R  C  -

GCCCTCTGCGGCACCAAGGAATGGAGGAGGGGACCCATGTAATCCTTTTGTTTAGTTTTG
1501 -----+---------+---------+---------+---------+---------+ 1560
     CGGAGACGCCGTGGTTCCTTACCTCCTCCCCTGGGTACATTAGGAAAACAAATCAAAAC
     A  S  A  H  Q  G  M  E  R  R  G  P  M  *  S  F  C  L  V  L  -
      P  L  R  T  K  E  W  R  G  G  D  P  C  N  P  F  V  *  F  C  -
       L  C  A  P  R  N  G  E  E  G  T  H  V  I  L  L  F  S  F  V  -
```

FIG. 2(x)

```
                                                              F  L  F  F  G  E  *  E  R  C  A  G  H  G  M  A  G  V  I  *
                                                               F  C  F  L  V  N  E  K  G  V  L  V  M  E  W  Q  V  S  Y  D
                                                                F  V  F  F  W  *  M  R  K  V  C  W  S  W  N  G  R  C  H  M  T
      TTTTGTTTTTTGGTGAATGAGAAAGGTGTCTGGTCATGGAATGGCAGGTGTCATATGA
1561  ---------+---------+---------+---------+---------+---------+ 1620
      AAAAACAAAAAACCACTTACTCTTTCCACAGACCAGTACCTTACCGTCCACAGTATACT

L  I  T  Q  S  R  *  G  K  L  *  S  L  S  P  L  L  I  A  T
                                                               *  L  L  R  A  D  E  E  N  C  G  L  *  V  L  C  *  S  Q  L
                                                                D  Y  S  E  Q  M  R  K  T  V  V  S  R  S  F  A  N  R  N  S
      CTTGATTACTCAGAGCAGATGAGGAAAACTGTAGTCTCTGAGTCCTTTGCTAATCGCAACT
1621  ---------+---------+---------+---------+---------+---------+ 1680
      GACTAATGAGTCTCGTCTACTCCTTTTGACATCAGAGACTCAGGAAACGATTAGCGTTGA

L  V  N  Y  S  D  S  F  L  C  R  I  *  F  V  *  S  V  L  T
                                                               *  L  *  I  I  L  I  L  F  Y  A  E  F  D  S  Y  D  Q  Y  *  L
                                                                C  E  L  F  *  F  F  M  Q  N  L  I  R  M  I  S  T  D  F
      CTTGTGAATTATTCTGATTCTTTTTTATGCAGAATTTGATTCGTATGATCAGTACTGACT
1681  ---------+---------+---------+---------+---------+---------+ 1740
      GAACACTTAATAAGACTAAGAAAAAATACGTCTTAAACTAAGCATACTAGTCATGACTGA
```

```
1741 TTCTGATTACTGTCCAGCTTATAGTCTTCCAGTTTAATGAACTACCATCTGATGTTTCAT 1800
     ----+---------+---------+---------+---------+---------+----
     AAGACTAATGACAGGTCGAATATCAGAAGGTCAAATTACTTGATGGTAGACTACAAAGTA

F * L L S S L * S S S L M N Y H L M F H  -
      S D Y C P A Y S L P V * T T I * C F I  -
      L I T V Q L I V F Q F N E L P S D V S Y  -

1801 ATTTAAGTGTATTTAAAGAAAATAAACACCATTATTCAAGCCATATAAAAAAAAAAAAA 1860
     ----+---------+---------+---------+---------+---------+----
     TAAATTCACATAAATTTCTTTTATTTGTGGTAATAAGTTCGGTATATTTTTTTTTTTTT

I * V Y L K K I N T I I Q A I * K K K  -
      F K C I * R K * T P L F K P Y K K K K K  -
      L S V F K E N K H H Y S S H I K K K K K  -

AAAA
```

| | | | | | |
|---|---|---|---|---|---|
| FIGF | (103) | TLKVIDEEWQ | RTQCSPRETC | VEVASELGKT | T..NTFFKPP CVNVFRCGGC |
| VEGF-C | (49) | ILKSIDNEWR | KTQCMPREVC | IDVGKEFGVA | T..NTFFKPP CVSVYRCGGC |
| VEGF | (39) | EVVKFMDVYQ | RSYCHPIETL | VDIFQEYPDE | I..EYIFKPS CVPLMRCGGC |
| PlGF | (39) | EVVPFQEVWG | RSYCRALERL | VDVVSEYPSE | V..EHMFSPS CVSLLRCTGC |
| PDGF-B | (84) | GSLTIAEPAM | IAECKTRTEV | FEISRRLIDR | TNANFLVWPP CVEVQRCSGC |
| PDGF-A | (83) | RRKRSIEEAV | PAVCKTRTVI | YEIPRSQVDP | TSANFLIWPP CVEVKRCTGC |
| | | | | | |
| FIGF | (151) | CNEEGVMCMN | TSTSYISKQL | FEIS.VPLTS | VPELVPVKIA NHTGCKCLPT |
| VEGF-C | (97) | CNSEGLQCMN | TSTSYLSKTL | FEIT.VPLSQ | GPKPVTISFA NHTSCRCMSK |
| VEGF | (87) | CNDEGLECVP | TEESNITMQI | MRIK..P.HQ | GQHIGEMSFL QHNKCECRPK |
| PlGF | (87) | CGDENLHCVP | VETANVTMQL | LKIR..S.GD | RPSYVELTFS QHVRCECRPL |
| PDGF-B | (134) | CNNRNVQCRP | TQVQLRPVQV | RKIEIVRKKP | IFKKATVTLE DHLACKCETV |
| PDGF-A | (133) | CNTSSVKCQP | SRVHHRSVKV | AKVEYVRKKP | KLKEVQVRLE EHLECACATT |

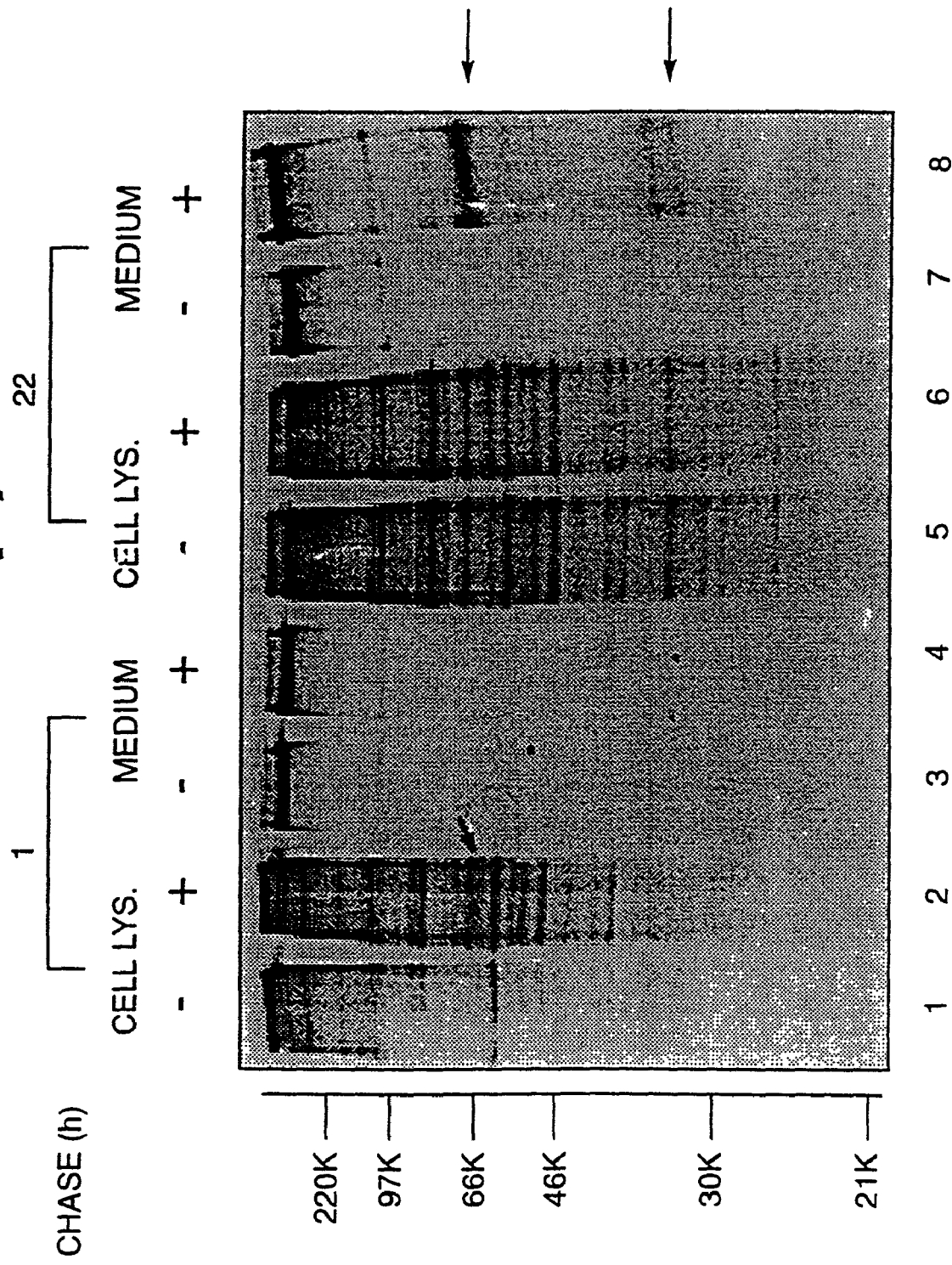

C-FOS INDUCED GROWTH FACTOR (FIGF) AND DNA ENCODING SAME

CROSS-REFERENCE TO RELATED APPLICATION

This application is a continuation of U.S. application Ser. No. 09/043,476, filed Mar. 18, 1998, now abandoned, which is a national stage application of PCT/IB96/01113, filed Sep. 30, 1996, which claims priority to foreign applications UK 9519928.7, filed Sep. 29, 1995, and UK 9612368.2, filed Jun. 13, 1996, each of which is incorporated herein in its entirety by reference.

BACKGROUND OF THE INVENTION

The present invention relates to the nucleotide sequences of Fos regulated genes, the proteins encoded by the sequences, uses of the sequences and encoded proteins, and transgenic animals comprising one or more of the sequences. The present invention also relates to antibody molecules having affinity for the encoded proteins and uses of the antibody molecules, and antisense nucleotide molecules and uses of the antisense nucleotide molecules.

The transcription factor AP-1 is involved in a number cellular processes, including cell proliferation, differentiation, and neuronal function (see Angel and Karin (1991) *Biochim. Biophys. Acta* 1072:129-57). AP-1 is considered to exert its effect by binding to a DNA recognition sequence, known as the AP-1 element, found in the promoter and enhancer regions of genes. The AP-1 element has the consensus sequence in TGA G/C TCA.

A number of genes have been found which contain AP-1 elements in their regulatory regions including c-Jun (Angel et al. (1988) *Cell* 55:875-885), MCP-1 (Rollins et al. (1988) *Proc. Natl. Acad. Sci. USA* 85:3738-3742), Stromelysin (Kerr et al. (1988) *Science* 242:1424-1427), Type I collagenase (Schonthal et al. (1988) *Cell* 54:325-334), and Interleukin II (Farrar et al. (1989) *Crit. Rev. Ther. Drug Carrier Syst.* 5:229-261). AP-1 is composed of dimeric complexes formed between Jun (c-Jun, Jun-B, and Jun D) and Fos (c-Fos, Fos B, Fra-1, and Fra-2) proteins. The Fos component of AP-1 has been found to be the limiting component of AP-1 activity in cycling cells (see Kovary and Bravo (1991) *Mol. Cell. Biol.* 11:2451-2459; Kovary and Bravo (1991) *Mol. Cell. Biol.* 11:4466-4472).

c-Fos is a nuclear proto-oncogene which has been implicated in a number of important cellular events, including cell proliferation (Holt et al. (1986) *Proc. Natl. Acad. Sci. USA* 831:4794-4798; Riabowol et al. (1988) *Mol. Cell. Biol.* 8:1670-1676), differentiation (Distel et al. (1987) *Cell* 49: 835-844; Lord et al. (1993) *MoL Cell. Biol.* 13:841-851), and tumorigenesis (Cantor et al. (1993) *Proc. Natl. Acad. Sci. USA* 90:10932-10936; Miller et al. (1984) *Cell* 36:51-60; Ruther et al. (1989) *Oncogene* 4:861-865). c-Fos encodes a 62 kDa protein which forms heterodimers with c-Jun, forming an AP-1 transcription factor which binds to DNA at an AP-1 element and stimulates transcription. Fos gene products can also repress gene expression. Sassone et al. (1988) *Nature* 334:314-319 showed c-Fos inhibits its own promoter, and Gius et al. (Gius et al. (1990) *Mol. Cell. Biol.* 10:4243-4255) and Hay et al. (1989) *Genes Dev.* 3:293-303 showed c-Fos inhibits early response genes Egr-1 and c-myc. AP-1 factors have also been shown to inhibit expression of the MHC class I and PEPCK genes (see Gurney et al. (1992) *J. Biol. Chem.* 267:18133-18139 and Howcroft et al., 1993).

It can therefore be seen that Fos regulated genes are extremely important for the correct expression of genes which lead to changes in the cell phenotype. The importance of Fos genes was clearly demonstrated by generating mice deficient in c-Fos (see Hu et al. (1994) *EMBO J.* 13: 3094-3103). The c-Fos deficient mice were viable, but displayed a range of tissue-specific developmental defects, including osteopetrosis, delayed gametogenesis and lymphophenia, and behavioral abnormalities.

The c-Fos deficient mice were used to generate fibroblast cell lines and the expression of two genes was found to be abnormally low. The two genes were Stromelysin and Type I collagenase. Both genes were previously identified as having AP-1 sites in their regulatory sequences (see Kerr et al. (1988) *Science* 242:1424-1427 and Schonthal et al. (1988) *Cell* 54:325-334). Stromelysin and Type I collagenase have been implicated in embryonic tissue development (Brenner et al. (1989) *Nature* 337:661-663), injured tissue remodelling (Hasty et al. (1990) *Arthritis Rheum.* 33:388-397; Woessner and Gurja (1991) *J. Rheumatol. Suppl.* 27:99-101), and in tumor progression and metastasis (Liotta and Stetler (1990) *Semin. Cancer Biol.* 1:99-106).

Superti-Furga et al. (1991) *Proc. Natl. Acad. Sci. USA* 88:5114-5118 showed that c-Fos activity can be controlled hormonally by fusing the mouse c-Fos protein to the ligand binding domain of the human estrogen receptor. The fusion protein was found to stimulate AP-1 dependent transcription in a strictly hormone-dependent manner. Using the fusion protein an AP-1 regulated gene, Fit-1, was found. Fit-1 was found to encode a secreted or membrane bound protein depending on the splicing pattern.

The present invention relates to the nucleotide sequences encoding two novel Fos regulated genes. The present invention provides a nucleotide molecule encoding a protein encoded by a Fos regulated gene or a fragment thereof, wherein said protein or fragment thereof is encoded by a nucleotide sequence shown in FIG. 1 (SEQ ID NO:1) or 2 (SEQ ID NO:3), or a fragment thereof, including allelic variants and species variants of the nucleotide sequences.

The term "nucleotide molecule" used herein refers to nucleotides of any length, either ribonucleotides or deoxyribonucleotides. The term encompasses both double and single stranded molecules. It also includes known types of modifications, for example labels which are known in the art, methylation, "caps", substitution of one or more of the naturally occurring nucleotides with an analog, internucleotide modifications such as, for example those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, proteins (including nucleases, toxins, antibodies, signal peptides, poly-L-lysine, etc.), those containing intercalators (e.g., acridine, psoralen, etc.), those containing chelators (e.g., metals, radioactive metals, boron, oxidative metals, etc.), those containing alkylators, and those containing modified linkages (e.g., alpha anomeric nucleic acids, etc.).

The nucleotide molecule of the present invention may encode the protein of a Fos regulated gene or a fragment thereof. The term "fragment" used in relation to the proteins refers to fragments which are of sufficient length to be unique to the presently claimed protein (e.g., 10, 15, 20, or 25 consecutive amino acids in length). Preferably, the protein fragments are capable of eliciting at least part of an activity of the full protein. Particularly preferred fragments comprise a conserved region of a gene which has been found to be homologous with a number of other genes. Such conserved regions are considered to have a specific function.

The nucleotide sequences shown in FIGS. 1 (SEQ ID NO:1) and 2 (SEQ ID NO:3) will, as with most naturally occurring nucleotide sequences, have a number of other forms, such as allelic variants and species variants. Such variants and any other naturally occurring forms of the nucleotide sequences of the present invention are also considered to form a part of the present invention. Such variants should have at least 60%, preferably 80%, and most preferably 90% sequence homology with the sequence shown in FIG. 1 (SEQ ID NO:1) or 2 (SEQ ID NO:3) or fragments thereof.

The present invention also relates to the nucleotide molecule of the present invention wherein the protein or a fragment thereof encoded by the sequence shown in FIG. 1 (SEQ ID NO:1) or 2 (SEQ ID NO:3) or a fragment thereof is altered. Preferred altered proteins or fragments thereof, are those that still retain their activity and preferably have a homology of at least 80%, more preferably 90%, and most preferably 95% to the protein or a fragment thereof encoded by the sequence shown in FIG. 1 (SEQ ID NO:2) or 2 (SEQ ID NO:4) or a fragment thereof. Preferably such altered proteins or fragments thereof differ by only 1 to 10 amino acids. It is further preferred that the amino acid changes are conservative. Note that FIG. 2 sets forth alternate reading frames (SEQ ID NOS: 17, 53, and 69) for the nucleotide sequence therein (SEQ ID NO: 3), which encode the corresponding predicted polypeptides (polypeptides SEQ ID NOS: 18-52 for SEQ ID NO: 17, polypeptides SEQ ID NOS: 54-68 for SEQ ID NO: 53, and polypeptides SEQ ID NOS: 70-90 for SEQ ID NO: 69) set forth in the figure.

Conservative changes are those that replace one amino acid with one from the family of amino acids which are related in their side chains. For example, it is reasonable to expect that an isolated replacement of a leucine with an isoleucine or valine, an aspartate with a glutamate, a threonine with a serine, or a similar conservative replacement of an amino acid with a structurally related amino acid will not have a major effect on the biological activity of the protein.

However, it is sometimes desirable to alter amino acids in order to alter the biological activity of the protein. For example, mutations which abolish or enhance one or more of the functions of the protein can be particularly useful. Such mutations can generally be made by altering any conserved sequences of protein. Mutations which increase the number of amino acids which are capable of forming disulphide bonds with other amino acids in the protein are particularly preferred in order to increase the stability of the protein. Mutations which decrease the number of amino acids which are capable of forming disulphide bonds with other amino acids in the protein may also be made if it is desired to decrease the stability of the protein. It is preferred that such altered proteins or fragments thereof have a homology of at least 80%, more preferably 90%, and most preferably 95% to the protein or a fragment thereof encoded by the sequence shown in FIG. 1 (SEQ ID NO:2) or 2 (SEQ ID NO:4) or a fragment thereof. Preferably such altered proteins or fragments thereof differ by only 1 to 10 amino acids.

The nucleotide molecule of the present invention can be obtained by methods well known in the art. For example, the sequences may be obtained by genomic cloning or cDNA cloning from suitable cell lines or from DNA or CDNA derived directly from the tissues of an organism, such as a mouse. Suitable cell lines include any fibroblast cell lines such as the 3T3 cell line, described by Hu et al. (1994) *EMBO J.* 13: 3094-3103. Positive clones may be screened using appropriate probes for the nucleotide molecule desired. PCR cloning may also be used. The probes and primers can be easily generated given that the sequences encoding the protein or a fragment thereof encoded by the nucleotide molecule of the present invention are given herein.

Numerous standard techniques known in the field of molecular biology may be used to prepare the desired nucleotide molecules or the probes and primers for identifying the positive clones. The nucleotide molecules probes or primers may be synthesized completely using standard oligonucleotide synthesis methods, such as the phosphoramidite method.

Numerous techniques may be used to alter the DNA sequence obtained by the synthesis or cloning procedures, and such techniques are well known to those skilled in the art. For example, site directed metagenesis, oligonucleotide directed mutagenesis, and PCR techniques may be used to alter the DNA sequence. Such techniques are well known to those skilled in the art and are described in the vast body of literature known to those skilled in the art, for example Sambrook et al. (1989) *Molecular Cloning: A Laboratory Manual* (Cold Spring Harbor Laboratory Press, Cold Spring Harbor, N.Y.).

The present invention further provides the protein encoded by the nucleotide molecule of the present invention. Preferably, the protein encoded by the nucleotide molecule of the present invention has the amino acid sequence shown in FIG. 1 (SEQ ID NO:2) or 2 (SEQ ID NO:4), or a fragment thereof.

The term "protein" as used herein refers to a polymer of amino acids and does not refer to a specific length of the product; thus, peptides, oligopeptides, and proteins are included within the term protein. The term also does not refer to or exclude post-expression modifications of the protein, for example, glycosylations, acetylations, and phosphorylations. Included in the definition are proteins containing one or more analogs of an amino acid (including for example, unnatural amino acids), proteins with substituted linkages, as well as other modifications known in the art, both naturally occurring and synthesized.

The protein of the present invention can be obtained from cells that naturally produce the protein such as fibroblast cells using standard purification techniques. However, it is preferred that a suitable host cell and vector system is used for the expression of the nucleotide molecule of the present invention. The nucleotide molecule of the present invention can be expressed in a variety of different expression systems, for example, those used with mammalian cells, baculoviruses, bacteria, and eukaryotic microorganisms such as yeasts.

All the above-mentioned expression systems are known in the art, and expressing nucleotide sequences is now a standard technique known to all skilled in the art. Preferably, eukaryotic, e.g., mammalian, host cell expression systems are used. In particular, suitable mammalian host cells include Chinese hamster ovary (CHO) cells, HeLa cells, baby hamster kidney (BHK) cells, cells of hepatic origin such as HepG2 cells, and myeloma or hybridoma cell lines.

The present invention further provides a vector for the expression of the nucleotide molecule of the present invention, comprising a promoter and the nucleotide molecule of the present invention. A mammalian promoter can be any DNA sequence capable of binding mammalian RNA polymerase and initiating the downstream transcription of a coding sequence into MRNA. Particularly useful promoters are those derived from mammalian viral genes, such as the SV40 early promoter, adenovirus major late promoter, and the herpes simplex virus promoter. Additionally, sequences from non-viral genes can also be used as promoters, such as from the murine metallothionein gene.

The nucleotide molecule of the present invention may be expressed intracellularly in mammalian cells. A promoter sequence may be directly linked with the nucleotide molecule of the present invention, in which case the first amino acid at the N-terminus of the encoded protein will be a methionine encoded by the start ATG codon.

Alternatively, the protein encoded by the nucleotide molecule of the present invention can be secreted from the cell by linking a nucleotide sequence encoding a leader sequence to the nucleotide molecule of the present invention. The encoded fusion protein will comprise a leader sequence fragment and the protein encoded by the nucleotide molecule of the present invention. The leader sequence will lead to the secretion of the fusion protein out of the cell. Preferably, there are processing sites between the leader sequence and the protein encoded by the nucleotide molecule of the present invention allowing the leader sequence to be cleaved off enzymatically or chemically. An example of such a leader sequence is the adenovirus triparite leader.

The vector of the present invention is preferably a nucleic acid vector comprising DNA. The vector may be of linear or circular configuration and can be adapted for episomal or integrated existence in the host cell, as set out in the extensive body of literature known to those skilled in the art. The vectors may be delivered to cells using viral or non-viral delivery systems. The choice of delivery system will determine whether the DNA molecule is to be incorporated into the cell genome or remain episomal.

The vector of the present invention can comprise further control elements such as polyadenylation signals, transcription termination signals, enhancers, locus control regions (LCRs), etc.

The present invention further provides a host cell transformed with the vector of the present invention. Transformation refers to the insertion of an exogenous polynucleotide into a host cell, irrespective of the method used for the insertion, for example, direct uptake, transduction, f-mating, or electroporation. The exogenous polynucleotide may be maintained as a non-integrated vector (episome), or may be integrated into the host genome. Preferably, the host cell is a eukaryotic cell, more preferably a mammalian cell, such as Chinese hamster ovary (CHO) cells, HeLa cells, baby hamster kidney (BHK) cells, cells of hepatic origin such as HepG2 cells, and myeloma or hybridoma cell lines.

The present invention further provides a method for producing the protein encoded by the nucleotide molecule of the present invention, comprising transfecting a host cell with the vector of the present invention, culturing the transfected host cell under suitable conditions in order to lead to the expression of the DNA molecule and the production of the desired protein. The protein may then be harvested from the transfected cells or from the cell growth media, depending on whether the protein is secreted, using standard techniques.

The present invention further provides the nucleotide molecule of the present invention for use in therapy.

The present invention further provides the use of the nucleotide molecule of the present invention in the manufacture of a composition for the treatment of developmental disorders.

The present invention further provides the use of the nucleotide molecule of the present invention in the treatment of developmental disorders.

Fos regulated genes are known to be involved in development and cell differentiation. Accordingly, the discovery of genes regulated by Fos has implications in the control of development and cell differentiation.

The nucleotide sequences shown in FIG. 1 (SEQ ID NO:1) and FIG. 2 (SEQ ID NO:3) have been found to have a similar sequence to genes of a family of growth factors characterized by the Platelet Growth Factor (PDGF) family signature. The most clearly related sequence is that of the Vascular Endothelial Growth Factor (VEGF). VEGF forms a homodimer which is a growth factor active in angiogenesis and endothelial cell growth (see Keck et al. (1989) *Science* 246:1309-1311 and Leung et al. (1989) *Science* 246:1306-1309). VEGF has also been used to stimulate angiogenesis and thereby produce a therapeutic effect (see Takeshita et al. (1994) *J. Clin. Invest.* 93:662-670).

The protein encoded by the nucleotide sequence (SEQ ID NO:1) in FIG. 1 is a mouse protein and the protein encoded by the nucleotide sequence (SEQ ID NO:3) in FIG. 2 is the human homologue of the mouse protein encoded by the sequence given in FIG. 1. Both the proteins are herein referred to as c-Fos Induced Growth Factor (FIGF).

The use of the nucleotide molecule of the present invention in therapy can therefore be seen to be an important application of the sequences of the Fos regulated genes of the present invention.

The nucleotide sequences shown in FIG. 1 (SEQ ID NO:1) and FIG. 2 (SEQ ID NO:3) are of particular interest in lung disorders as it is has been found that the nucleotide sequences are mainly expressed in the lungs. Particular lung disorders which may be treatable using the nucleotide molecule encoding the protein or fragments thereof which are encoded by the sequence shown in FIG. 1 (SEQ ID NO:1) or FIG. 2 (SEQ ID NO:3), include pneumonia and pneumoconiosis. The nucleotide molecule may also be used following pneumonectomy in order to aid in lung re-growth.

The nucleotide sequence in FIG. 2 (SEQ ID NO:3) has been mapped to human chromosome Xp22, near the locus that maps for the pathology spondyloepiphyseal dysplasia (SEDL). The genetic map of this region is described by Ferrero et al. (Ferrero et al. (1995) *Human Molecular Genetics* 4:1821-1827) and the mapping of the SEDL disease is described by Heuertz et al. (1993) *Genomics* 18:100-104. SEDL may therefore be treatable using the nucleotide molecule encoding the protein or fragments thereof, which are encoded by the nucleotide sequence given in FIG. 1 (SEQ ID NO:1) or in FIG. 2 (SEQ ID NO:3).

As previously discussed, Fos regulated genes have been found to be involved in tumor progression and metastasis. By inhibiting Fos regulated genes it is possible to inhibit or suppress tumor growth.

Previously Kim et al. (Kim et al. (1993) *Nature* 362:841-844) suppressed tumor growth by injecting monoclonal antibodies specific for VEGF. As stated previously, VEGF has a similar nucleotide sequence to the nucleotide sequences shown in FIG. 1 (SEQ ID NO:1) and FIG. 2 (SEQ ID NO:3). Accordingly, by inhibiting either the in vivo expression, translation, etc. of the native nucleotide molecules of the present invention, tumor growth may be inhibited or suppressed.

The actions of the Fos regulated genes corresponding to the nucleotide molecules of the present invention may be inhibited by a number of techniques. Preferred techniques include antisense-based techniques, ribozyme-based techniques, and antibody-based techniques.

Antibody molecules having specificity for the protein encoded by the nucleotide molecules of the present invention can be used to block the function of the protein and thereby inhibit or suppress tumor growth.

The present invention further provides antibody molecules having specificity for the protein of the present invention. The antibody molecules may be a complete polyclonal or monoclonal antibody or antigen-binding fragments, such as Fv, Fab, F(ab')$_2$ fragments and single chain Fv fragments thereof. The antibody molecule may be a recombinant antibody molecule such as a chimeric antibody molecule preferably having human constant regions and mouse variable regions, a humanized CDR-grafted antibody molecule or fragments thereof. Methods for producing such antibodies are well known to those skilled in the art and are described in EP-A-0120694 and EP-A-0125023.

The present invention further provides the antibody molecule of the present invention for use in therapy.

The present invention also provides the use of the antibody molecule of the present invention in the manufacture of a composition for the treatment of proliferative diseases such as cancer.

The present invention further provides the use of the antibody molecule of the present invention for the treatment of proliferative diseases such as cancer.

The present invention further provides an antisense nucleotide molecule or a fragment thereof, having the complementary sequence to the nucleotide molecule or a fragment thereof, of the present invention. The antisense nucleotide molecule of the present invention can be generated using the same standard techniques as for the nucleotide molecule of the present invention.

The present invention further provides an antisense vector for the expression of the antisense nucleotide molecule of the present invention comprising a promoter and the antisense nucleotide molecule. The antisense vector is identical to the nucleic acid vector of the present invention except that the vector contains the antisense nucleotide molecule of the present invention.

The present invention further provides the antisense vector of the present invention for use in therapy.

The present invention further provides the use of the antisense vector of the present invention in the manufacture of a composition for the treatment of cell proliferative diseases such as cancer.

The present invention further provides the use of the antisense vector of the present invention in the treatment of cell proliferative diseases such as cancer.

The present invention further provides a vector for the expression of a ribozyrne, comprising a promoter and a nucleotide sequence encoding a ribozyme capable of cleaving the RNA transcript of the nucleotide molecule of the present invention. The vector encoding the ribozyme is identical to the vectors previously described except that the vector encodes a ribozyme. The ribozyme being capable of cleaving the RNA transcript of the nucleotide molecule of the present invention. Techniques for producing such ribozymes are known to those skilled in the art and are discussed in Cantor et al. (Cantor et al. (1993) *Proc. Natl. Acad. Sci. USA* 90:10932-10936).

The present invention further provides the ribozyme-encoding vector of the present invention for use in therapy.

The present invention further provides the use of the ribozyme-encoding vector of the present invention in the manufacture of a composition for the treatment of cell proliferative diseases such as cancer.

The present invention further provides the use of the ribozyme-encoding vector of the present invention in the treatment of cell proliferative diseases such as cancer.

A further object to the present invention is the use of the protein of the present invention in identifying the receptor or receptors of the protein or of a protein complex comprising the protein. Methods for identifying receptors are well known to those skilled in the art and have been widely described in the literature. However, basically there are three major ways of identifying receptors:

i. Test all known receptors that bind to similar molecules. This is particularly useful for the protein encoded by the DNA sequences shown in FIG. 1 and FIG. 2, as VEGF has been found to have a similar sequence.

ii. Perform a binding purification step. For example, the protein of the present invention or a protein complex comprising the protein of the present invention can be immobilized on to a solid support and numerous possible receptor molecules, especially membrane proteins, are then passed over the solid support. A binding purification procedure is described in Schuster et al. (1995) *Brain Res.* 670:14-28.

iii. By screening expression libraries in order to find cells lacking the receptor or receptors and then utilizing the receptor cloning method described by Seed and Aruffo (1987) *Proc. Natl. Acad. Sci. USA* 84:3365-3369.

Other methods are also known to those skilled in the art and can be used in order to find the receptor or receptors.

On identifying the receptor or receptors it will be possible to design drugs that block or enhance the activity of the receptor or receptors and produce antibody molecules that block the receptor or receptors. Once the DNA sequence of the receptor or receptors are known, a number of gene therapies may be designed for correcting errors in the receptor or receptors, or for blocking expression of the receptor or receptors.

The present invention further provides the use of the protein of the present invention in an assay for identifying antagonists or agonists of the protein which may be used as drugs in the treatment of cancer and developmental disorders respectively. Assays for identifying such potential drugs are frequently used and are well known to those skilled in the art. An example of such an assay is clearly described in Tsunoda et al. (1994) *Anti-cancer Res.* 14:2637.

The present invention further provides the use of the nucleotide molecule, antisense nucleotide molecule, protein, or antibody molecule of the present invention, or any combination thereof, in diagnosing a pathological state or a predisposition to a disease.

The nucleotide molecule or antisense nucleotide molecule of the present invention may be used in determining the presence of the gene corresponding to the nucleotide molecule or in determining the amount of RNA transcribed from the gene.

The protein of the present invention may be used in an assay for determining the amount of protein encoded by the gene corresponding to the nucleotide molecule of the present invention.

The antibody molecule of the present invention may be used in an assay for determining the amount of protein encoded by the gene corresponding to the nucleotide molecule of the present invention. An example of an assay for determining the amount of protein using the antibody molecule of the present invention is a competitive binding assay.

By determining the presence of the gene corresponding to the nucleotide molecule of the present invention or the transcribed RNA or the protein encoded by the gene, it is possible to diagnose a pathological state or a predisposition to a disease caused by the presence of the gene or the overexpression of the gene.

The present invention further provides the use of the nucleotide molecule of a present invention in the generation of transgenic animals. In particular, the invention provides the use of such nucleotide molecules for the generation of non-human transgenic animals, especially transgenic mice.

Transgenic animals can be generated which are suitable as models for research. For example, transgenic animals which overexpress the nucleotide molecule of the present invention could be used in order to determine what effects overexpression will have. Alternatively, transgenic animals can be generated where the native nucleotide molecule of the present invention is "knocked out". The effect of "knocking out" the nucleotide molecule could then be investigated.

Methods for generating such transgenic animals are well known to those skilled in the art and can be easily performed given that the nucleotide molecules to be overexpressed or "knocked out" are disclosed herein.

The transgenic animals of the present invention could also be subsequently bred with either Fos overexpression mice or Fos "knocked out" mice, in order to determine the effects of altered Fos control.

The present invention also provides a nucleotide molecule comprising all or part of the sequence shown in any one of FIG. 1 (SEQ ID NO:1) or 2 (SEQ ID NO:3). The nucleotide molecule comprising all or part of the sequence shown in any one of FIG. 1 (SEQ ID NO:1) or 2 (SEQ ID NO:3) may encode a protein or may be non-coding. Preferably, the nucleotide molecule additionally encodes the control sequences of the Fos gene corresponding to the nucleotide sequence shown in any one of FIG. 1 (SEQ ID NO:1) or 2 (SEQ ID NO:3). It is further preferred that the nucleotide molecule encodes a sequence which confers Fos regulation to a gene. It is particularly preferred that the nucleotide molecule comprises the sequence TGACTCA.

The present invention is now illustrated in the appended examples with reference to the following figures.

FIG. 1

FIG. 1 discloses a DNA sequence (SEQ ID NO:1) of Fos regulated gene F0401, showing the encoded protein sequence (SEQ ID NO:2) and the regions homologous to VEGF (underlined).

FIG. 2

FIG. 2 discloses a DNA sequence of Fos regulated gene HF175 (human homologue of F0401), showing the deduced protein sequences (SEQ ID NOS: 18-52, SEQ ID NOS: 54-68, and SEQ ID NOS: 70-90) encoded by the three different reading frames (SEQ ID NOS: 17, 53, and 69, respectively) of the same nucleotide sequence (SEQ ID NO:3), wherein the boxed, amino acid sequence (SEQ ID NO:4) is the correct amino acid sequence for human FIGF as encoded by the correct reading frame. FIG. 2 also shows the complementary sequence of nucleotide sequence SEQ ID NO: 3—this sequence corresponds to SEQ ID NO: 91 in the Sequence Listing.

FIG. 3

FIG. 3 shows a comparative overlapping alignment of two polypeptide segments from human FIGF (SEQ ID NOs:5 and 11) with two conserved domains of each of VEGF-C (SEQ ID NOs:6 and 12), VEGF (SEQ ID NOs:7 and 13), PlGF (SEQ ID NOs:8 and 14), PDGF-B (SEQ ID NOs:9 and 15), and PDGF-A (SEQ ID NOs:10 and 16), respectively. The number in parentheses is the number of the first residue in the polypeptide segment or domain. Dots indicate the cysteine residues which are characteristic of these growth factors (i.e., VEGF-C, VEGF, PlGF, PDGF-B, and PDGF-A).

FIG. 4

FIG. 4A is an SDS-PAGE gel showing the presence of the FIGF protein (by immunoprecipitation) in cell lysates and culture medium from cells transfected with vector alone (−) or vector encoding FIGF (+) at 1 hour (lanes 1-4) and 22 hours (lanes 5-8) after transfection. COS-7 cells transfected with the vector alone (−) or with a vector containing the FIGF coding sequence under the control of a CMV promoter (+) were metabolically labeled for 1 hour with [$^{35}$S]Methionine and [$^{35}$S]Cysteine each at a concentration of 100 µCi/ml. After 1 hour or 22 hours chase, conditioned media and cell lysates were immunoprecipitated separately with anti-FIGF polyclonal antibodies. [The FIGF protein was expressed in *E. coli* under the control of the T5 promoter. The cDNA fragment, from the coding region of FIGF, was generated by PCR from the Methionine residue at position +40 and cloned into the pQE-31 vector (Qiagen) to obtain a fusion protein with a N-terminal Histidine tag. The protein was expressed in TG1 bacteria (pREP+) by induction for 4 hours at 37° C. in the presence of 2 mM isopropyl-β-D-thigalactopyranoside. The recombinant protein was exclusively localized in inclusion bodies, and was purified on a column of Ni-NTA-Resin, under denaturing conditions according to the manufacturer's protocols (Qiagen). Antibodies were raised by injecting rabbits with 200 µg of recombinant FIGF in form of denaturated protein in complete Freund's adjuvant. Serum was prepared after 4 injections in incomplete Freund's adjuvant at 3-week intervals]. The immunocomplexes were collected by protein-A Sepharose beads (Pharmacia) and separated on 12% SDS-PAGE in the presence of 3% β-mercaptoethanol. Arrows indicate specific bands present only in FIGF transfected cells.

FIG. 4B is a graph showing the mitogenic activity measured as [3H]-thymindine incorporation (cpm×10$^3$) versus volume (µl) of conditioned medium in c-fos (−/−) fibroblasts transfected with vector encoding FIGF versus vector alone (mock). Cells were incubated with conditioned medium of COS-7 cells transfected with the FIGF expression vector or with the vector alone. One day after transfection the cells were split and kept in 2% serum. Conditioned media were collected after 120 hours.

FIG. 4C is a graph showing the mitogenic activity measured as [3H]-thymidine incorporation in c-fos (−/−) fibroblasts. Cells were incubated with conditioned media obtained from c-fos (−/−) stable clones, named FH-10.2, FH-10.5, FH-9.3, FH-9.6, FH-10.9, and c-fos (−/−) cells (mock), constitutively expressing exogenous FIGF under the control of the CMV promoter. Conditioned media were collected from cells cultured for 48 hours in 0.5% serum.

FIG. 4D is a graph showing the mitogenic activity measured as [3H]-thymidine incorporation in c-fos (−/−) fibroblasts as a function of concentration of FIGF in µg/ml. Cells were incubated with partially renatured recombinant FIGF. Under the same conditions, incubation with PDGF-BB (Sigma), used as a positive control, induces about 30% higher thymidine incorporation, while VEGF (Sigma) does not induce incorporation above the background. The data shown are the mean of six experiments performed with two different FIGF preparations.

FIG. 4E is a graph showing the mitogenic activity measured as [3H]-thymidine incorporation on mouse embryo fibroblasts as a function of the concentration of FIGF in µg/ml. Cells were incubated with partially renatured recombinant FIGF. MEF cells were obtained from 13-15 day embryos of B6D2F1 mice. The embryos were sacrificed, rinsed, and trypsinized for 30 min at 37° C. The MEF cells were grown 24 hours in medium containing 0.5% serum before addition of the growth factors. Under the same conditions, incubation with PDGF-BB (Sigma), used as a positive control, induces about 30% higher thymidine incorporation, while VEGF (Sigma) does not induce incorporation above the background. The data shown are the mean of six experiments performed with two different FIGF preparations. The background values were subtracted in each experiment.

FIG. 5

FIG. 5A is a Northern blot analysis of total RNA obtained from: c-fos (−/−) fibroblasts (lanes 1-3); a stable cell line, obtained from c-fos (−/−) cells, expressing exogenous c-fos (lanes 4-6); c-fos (+/+) fibroblasts (lanes 7-9). Cellular RNA was extracted by the guanidine thiocyanate method after incubation of cells for 48 hours in 0.5% serum (time 0). The serum concentration was increased to 10%, and total RNA was collected at 2 or 4 hours as indicated. Lanes 10 and 11 show FIGF expression in c-fos (−/−) fibroblasts transiently transfected with the vector alone (mock) or containing the c-fos under the FBJ-LTR constitutive promoter (c-fos). The RNAs of the transiently transfected cells were collected 30 hours after culturing the cells in medium containing 0.5% serum. Each lane was loaded with 10 µg of total cellular RNA.

FIG. 5B contains two pairs of Northern blots, reflecting the expression of PDGF and VEGF, respectively, as a function of time (0, 2 h, and 4 h), from RNA extracts of c-fos (−/−) cells (lanes 1-3) and from a stable cell line obtained from c-fos (−/−) cells expressing exogenous c-fos (lanes 4-6), relative to control blots expressing GAPDH as a control protein. Cellular RNAs were extracted as indicated in FIG. 5A. Glyceraldehyde-phosphate-dehydrogenase (GAPDH) was used as a control for RNA loading.

FIG. 6

FIG. 6 is a Northern analysis of RNA poly A+ extracted from different mouse tissues.

FIG. 7

FIGS. 7A to 7H are photos showing the morphology of cells stably transfected by an expression vector as a function of the protein encoded by the expression vector. FIG. 7A is a photo showing the morphology of c-fos deficient cells. The cells were stably transfected with the vector alone.

Figure 7C:
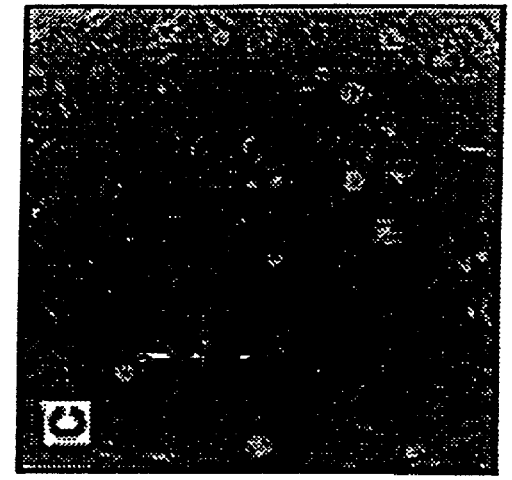
FIG. 7C is a photo showing the morphology of cells stably transfected with an expression vector containing the FIGF cDNA in the antisense orientation under the control of the CMV promoter.
Figure 7B:
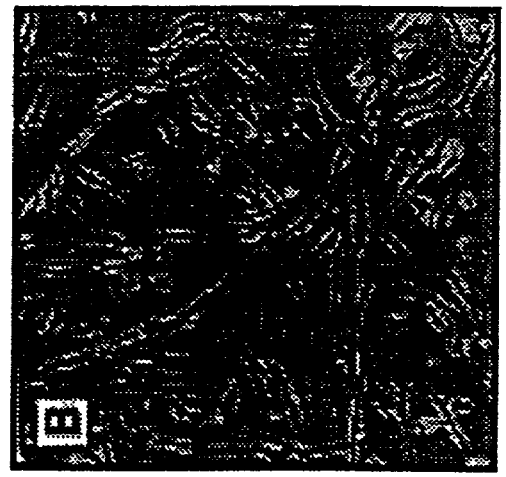
FIG. 7B is a photo showing the morphology of a cell clone derived from c-fos deficient cells, stably transfected with the expression vector containing FIGF under the control of the CMV promoter.
Figure 7A:
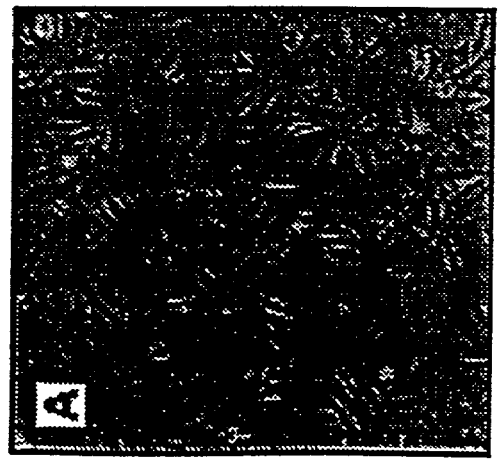
FIG. 7D is a photo showing the morphology of cells stably transfected with the expression vector containing c-fos under the control of the FBJ-LTR promoter.
FIG. 7E is a photo showing the morphology of a cell clone derived from the same cells as in D (expressing c-fos constitutively) transfected with an expression vector containing FIGF under the control of the CMV promoter.
FIG. 7F is a photo showing the morphology of a cell clone derived from the same cells as in D (expressing c-fos constitutively) transfected with an expression vector containing the FIGF cDNA in the antisense orientation under the control of the CMV promoter.
FIG. 7G is a photo showing the morphology of c-fos (−/−) fibroblasts cultured for 120 hours in medium containing 0.5% serum.
Figure 7D:
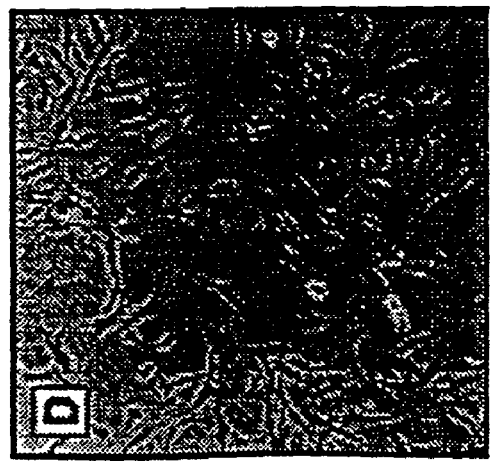
Figure 7E:
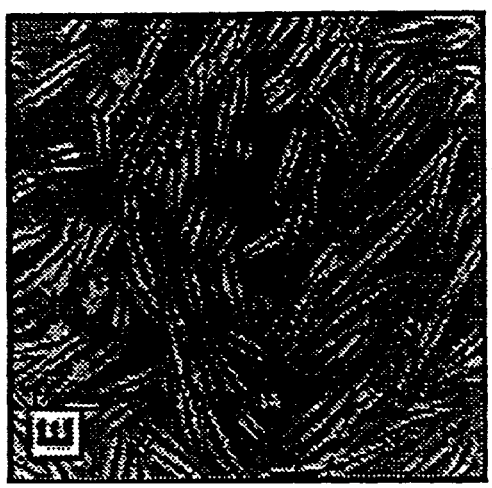
Figure 7F:
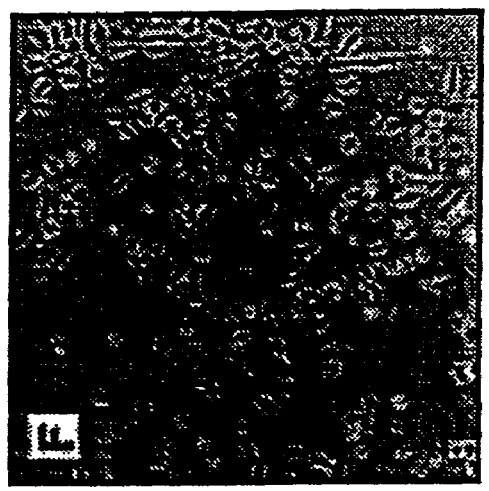
Figure 7G:
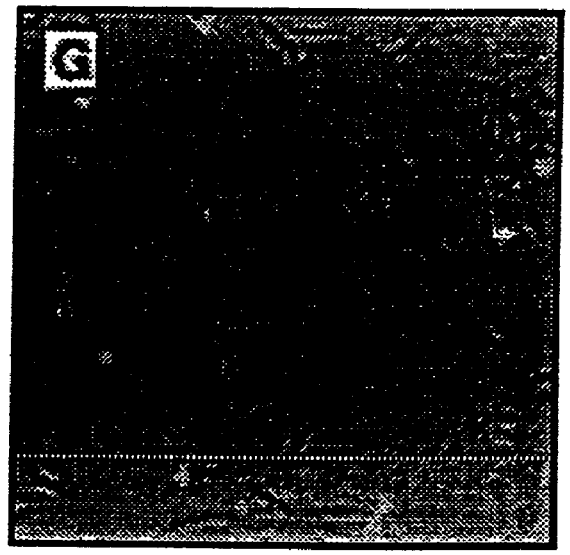
Figure 7H:
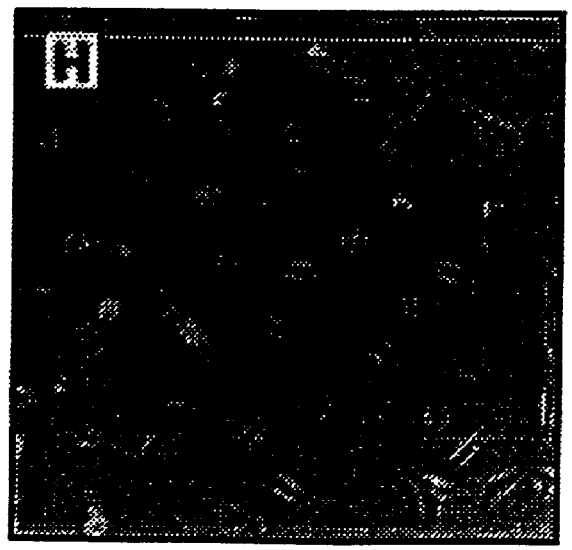

FIG. 7H is a photo showing the morphology of cells as in 7G but treated for 120 hours with partially renatured recombinant FIGF. Ten independent clones obtained from 3 independent transfections were analyzed. All showed morphological changes similar to those observed in the figure.

EXAMPLES

Cell Culture and Clone Isolations

Mouse fibroblast wild-type cells with respect to c-Fos expression (+/+) and c-Fos-deficient (−/−) 3T3 cell lines and stably transfected cell line that constitutively express exogenous c-Fos were generated as described (Hu et al. (1994) *EMBO J.* 13: 3094-3103). All cell lines were grown at 37° C. with 5% in Dulbecco's modified Eagle's medium (DMEM) supplemented with 10% fetal calf serum (FCS), glutamine, and penicillin-streptomycin. Cells were cultured until reaching about 70% confluence, serum starved for 48 hours in DMEM containing 0.5% FCS, and stimulated with DMEM containing 10% FCS for 0, 2, and 4 hours prior to RNA isolation. Total RNA was isolated using the quanidine-isothiocyanate method. MRNA differential display was performed as described by Laing et al. and modified by Bauer et al. (Bauer et al. (1993) *NAR* 21: 4272-4280). Briefly, from the extracted RNA chromosomal DNA contamination was removed from 50 µg of the total RNA isolated by DNase I treatment. 0.2 µg of RNA, extracted at 2 or 4 hours after serum induction, was used for reverse transcription in a 40 µl reaction volume using $dT_{12}$ mN primers and 300 U MMLV reverse transcriptase (Promega Corp., Madison, Wis.) with an incubation time of 60 min at 37° C. The PCR mixture for the cDNA amplification contained $dT_{12}$ mN primer, one of the 20 10mer deoxyoligonucleotide primers with arbitrary sequence (Kit A-Operon Biotechnology Inc., Alameda, Calif.), $^{33}$p-dATP (Amersham International p1c, Buckinghamshire, England), and 1U Taq polymerase (Promega Corp.). Samples were subjected to 40 cycles of amplification using a PTC-100 thermocycler (MJ Research Inc., Watertown, Mass.). The cycling parameters were as follows: 94° C. for 30 seconds, 42° C. for 90 seconds, 72° C. for 30 seconds, and an additional extension period at 72° C. for 10 min. 2 µl of the PCR mixture was adjusted with glycerol to 5% and loaded onto a 6% polyacrylamide gel without urea (Bauer et al. (1993) *NAR* 21: 4272-4280). The bands of cDNA differentially expressed were recovered from the gel and reamplified. Reamplified cDNA probes were run on a 1.5% agarose gel, purified, and cloned into the pGEM-T vector using the TA cloning system (Promega Corp.). Positive clones were selected using the blue-white phenotype.

Characterization and Sequencing of Novel Clones

Typically from one band we could obtain 1 to 3 different clones, which we utilized for the successive characterization by Northern blot analysis. The cDNA fragments were labeled with $^{32}$P-dCTP using a random primer labeling kit (Amersham International p1c). Hybridization signals were screened and quantitated by PhosphorImager using Image Quant software (Molecular Dynamics, Sunnyvale, Calif.). Plasmid DNA sequencing of cloned cDNA probes with either T7 or SP6 primer was carried out manually using the Sequenase V 2.0 Kit (US Biochemical Inc., Cleveland, Ohio). Briefly, the RNA extracted from the cells were subjected to amplification utilizing random primers and the bands of a cell type are identified by comparison and isolated. The fragments obtained were tested in Northern blot with RNA from the cell lines to confirm that the corresponding mRNA are up regulated in Fos expressing cells. Then we generated our own cDNA library in lambda ZAP vectors from mouse fibroblasts cell lines to obtain the full length clones utilizing a cDNA Synthesis and Cloning Kit (Stratagene). The screening was performed according to the manufacturer. Positive clones were first analyzed by restriction map, and the longest ones were subjected to DNA sequence.

Clone Analysis

The F0401 DNA sequence (SEQ. ID NO:1) is shown in FIG. 1 and the HF175 DNA sequence (SEQ ID NO:3) is shown in FIG. 2. A simple search analysis against the NIH and EMBL data banks revealed that F0401 and the human homologue FIGF are novel genes, and their sequences are similar to the genes of a family of growth factors characterized by the Platelet Growth Factor (PDGF) family signature. The consensus pattern of the family is: C-V-x(3)-R-C-x-G-C-C-N (SEQ ID NO: 92).

Members of this family form dimers with disulphide links and are potent mitagens. The most similar sequence to F0401 and HF175 is the Vascular Endothelial growth factor (VEGF) which forms an homodimer and is a growth factor active in angiogenesis and endothelial cell growth (Keck et al. (1989) *Science* 246:1309-1311; Leung et al. (1989) *Science* 246: 1306-1309). As VEGF is a growth factor, its overexpression can result in tumor angiogenesis (Plate et al. (1993) *Cancer Research* 53:5822-5827). Recent reports indicate possible therapeutic use based on VEGF inhibition in tumors (Kim et al. (1993) *Nature* 362:841-844) and on VEGF treatment to stimulate angiogenesis (Takeshita et al. (1994) *J. Clin. Invest.* 93:662-670).

The following experiments were performed using F0401.

The FIGF predicted protein sequence (SEQ ID NO:4) has a hydrophobic sequence at the N-terminus which could code for a signal peptide. This long N-terminus region does not show significant homology to known proteins. However, there is a positively charged domain in this region which may allow binding of the protein to the cell membrane or to the extracellular matrix.

Figure 4B:
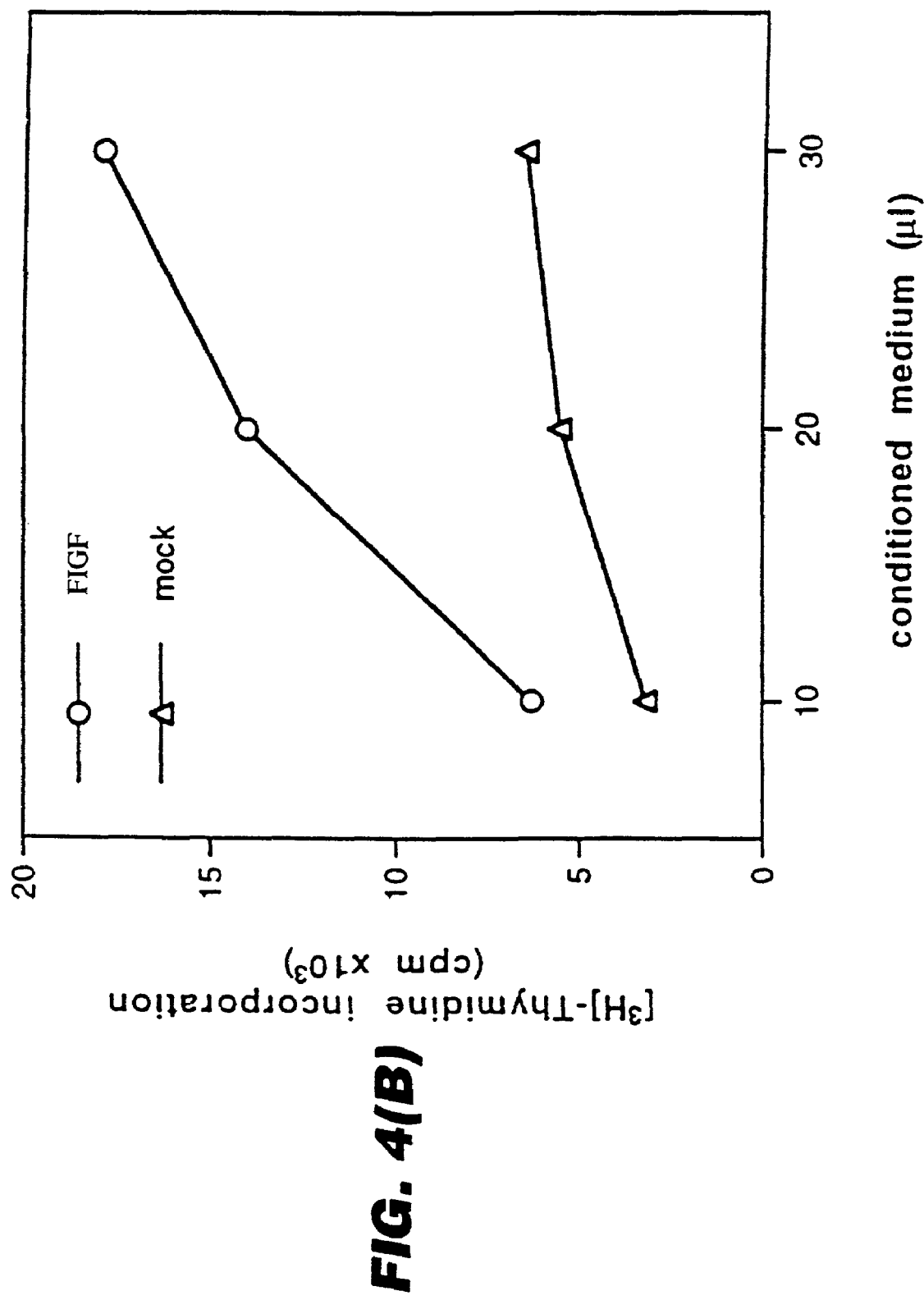

To verify if FIGF is a secreted protein, we transfected COS-7 cells with an expression vector containing the FIGF cDNA under the control of the cytomegalovirus (CMV) immediate early gene promoter. Polyclonal antibodies, raised against recombinant FIGF (as described previously), immunoprecipitated a specific band that is observed in both the cell lysates and the conditioned media of the FIGF transfected COS-7 cells (FIG. 4A). After 1 hour labeling followed by 1 hour chase, a specific band was mainly present in the cell lysate while, after a chase longer than four hours, the protein accumulated in the cell supernatant. Under non-denaturing conditions, FIGF aggregated into a multimeric form. Addition of β-mercaptoethanol resulted in partial denaturation of the protein which migrated mostly as a 66 kDa band and only a minor fraction of the protein can be found as a monomer of the expected 33 kDa of molecular mass (FIG. 4A). These results show that FIGF is a secreted protein and can form dimers. Dimerization of FIGF could be predicted since the FIGF central domain is highly conserved and contains the cysteine residues involved in the dimerization of both PDGF and VEGF.

Figure 4C:
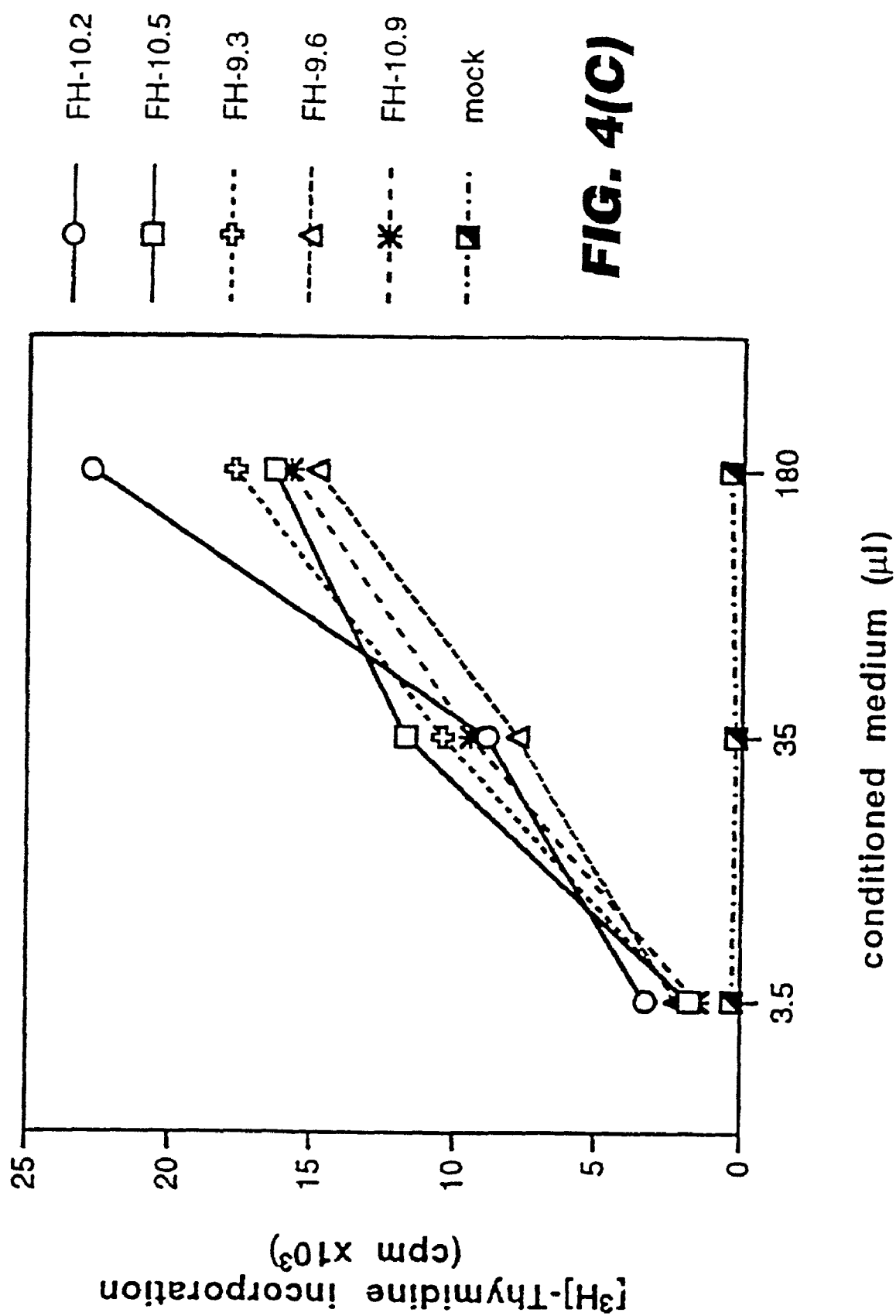

It was further investigated whether the conditioned medium of FIGF producing cells could promote cell growth in vitro, assayed as [3H]-thymidine incorporation (Vaziri et al. (1995) *MoL Cell. BioL* 15:1244-1253). Conditioned medium was obtained either from transiently transfected COS-7 cells or from stable clones, derived from c-fos(−/−) fibroblasts, expressing FIGF under the control of the CMV promoter. The mitogenic activity of the medium containing FIGF was tested on c-fos (−/−) fibroblasts. Conditioned medium from both transfected COS-7 (FIG. 4B) or stable fibroblast clones overexpressing FIGF (FIG. 4C) induces DNA synthesis in c-fos (−/−) fibroblasts.

Figure 4D:
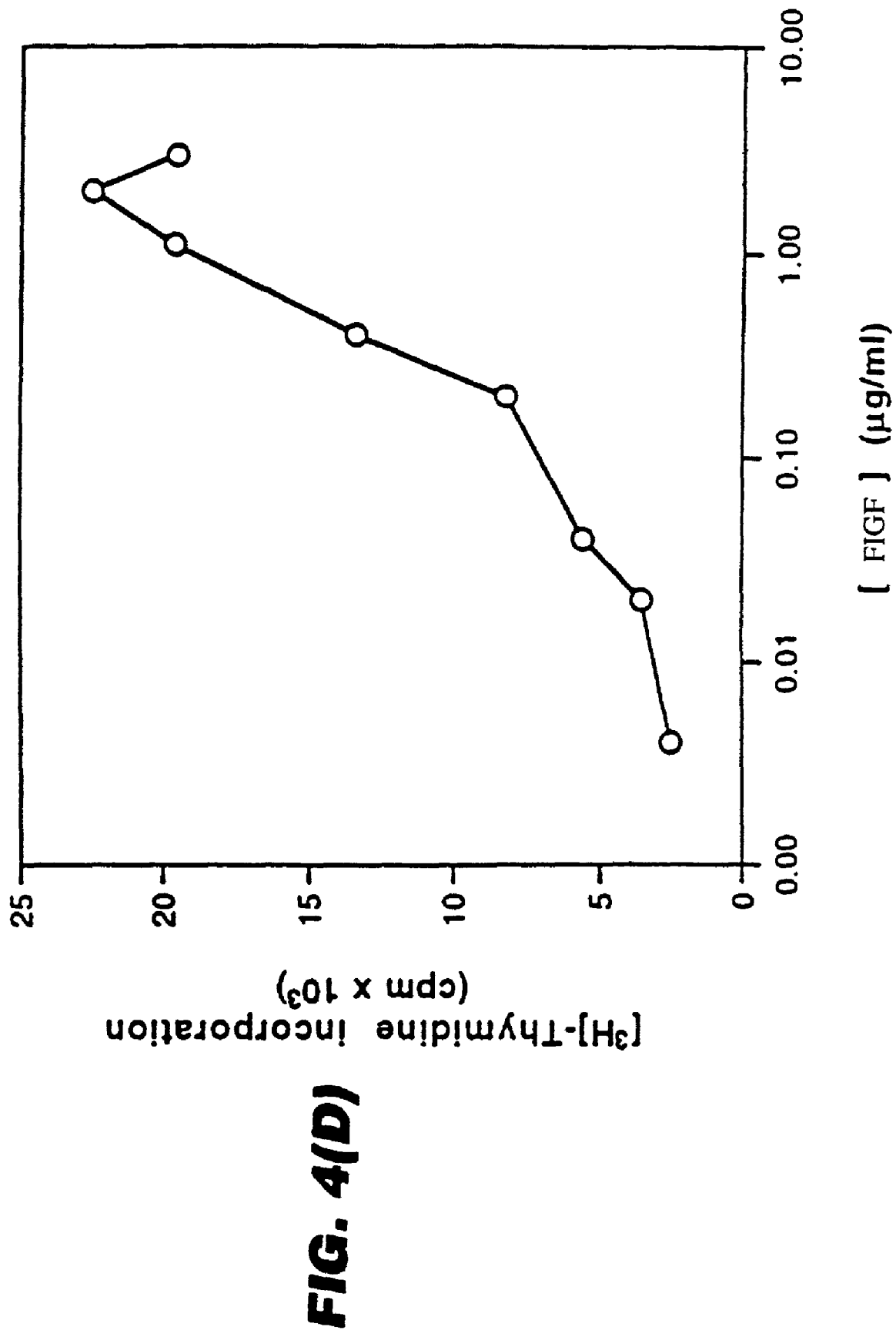

As in mammalian cells FIGF expression could induce the activation of other growth factors, which in turn would be responsible for the [3H]-thymidine incorporation measured, we tested the mitogenic activity of a recombinant FIGF protein expressed in *E. coli* (as described previously). In order to obtain a biologically active recombinant protein, the purified FIGF protein from *E. coli* was partially renatured in the presence of a mixture of reduced and oxidized glutathione. The purified recombinant protein was adjusted to 0.4 mg/ml and completely reduced in the presence of 8 M Urea, 2% β-mercaptoethanol for 1 hour at 370° C. The reduced protein was dialized against a solution containing 50 mM Tris-Cl pH 8.0, 1 M Urea, 5 mM reduced glutathione, and 0.5 mM oxidized glutathione for 2 days, and against a solution containing 20 mM Tris-Cl pH 7.5, 0.7 M NaCl for 1 day, as described by Hoppe et al., *Biochemistry*, 28, pp. 2956-2960 (1989); Hoppe et al, *Eur. J. Biochem.*, 187, pp. 207-214 (1990). The partially refolded recombinant FIGF induced DNA synthesis on c-fos (−/−) fibroblasts in a dose-dependent manner (FIG. 4D). As expected, c-fos (−/−) cells are also responsive to PDGF-BB, while the treatment with VEGF did not induce [3H]-thymidine incorporation in these cells. The highest activity of DNA synthesis was obtained with 2 μg of purified FIGF. The apparently low specific activity of the recombinant FIGF observed is most probably due to the low efficiency of FIGF correct refolding since FIGF contains 29 cysteine residues out of 358 amino acids.

Figure 4E:
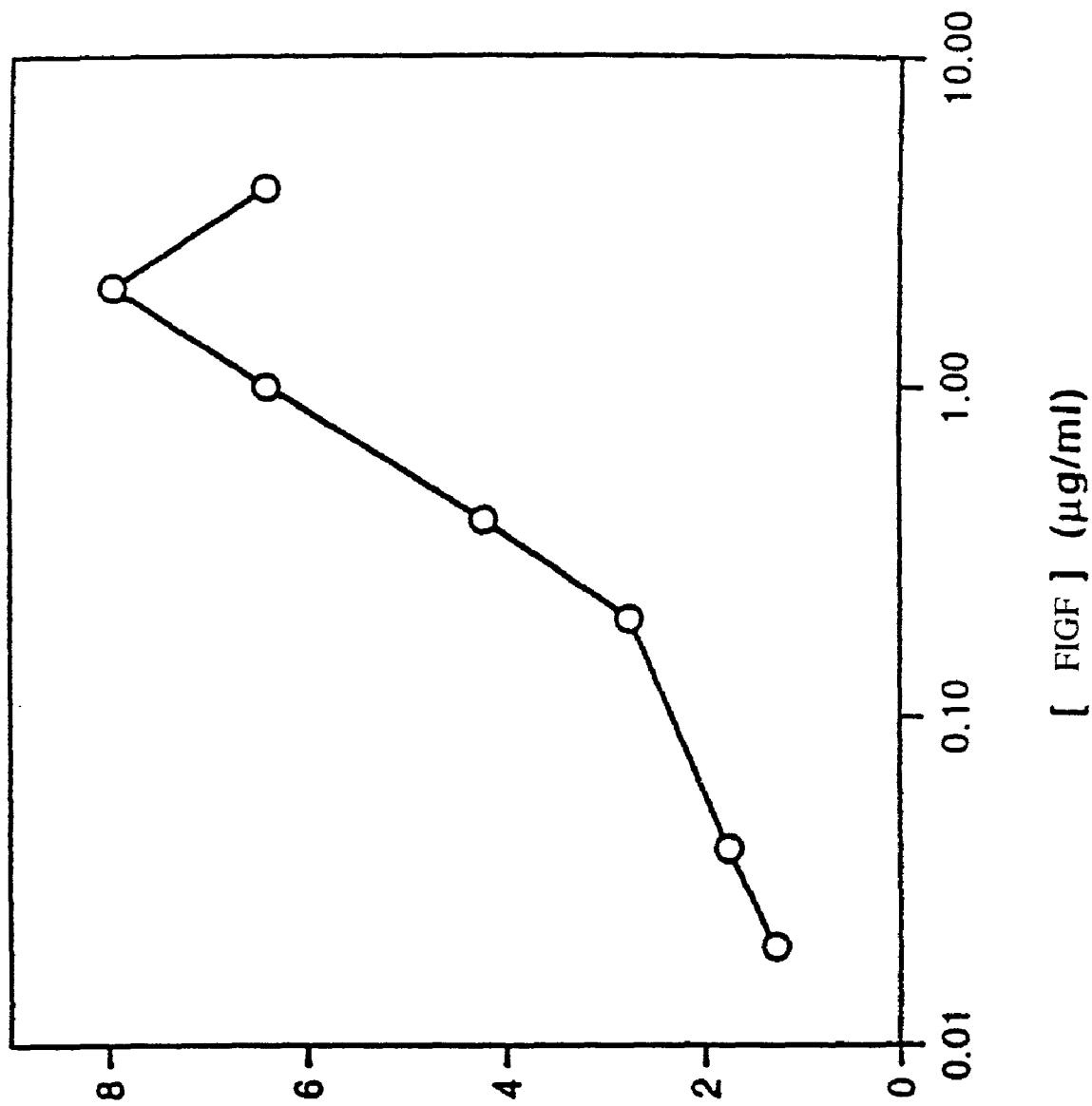

We also tested the mitogenic activity of the recombinant FIGF on mouse embryo fibroblasts (MEF). FIGF induced DNA synthesis on mouse embryo fibroblasts in a dose-dependent dependent manner (FIG. 4E). The FIGF cDNA was isolated by differential screening of RNA from cells differing only for the expression of c-fos.

Figure 5A:
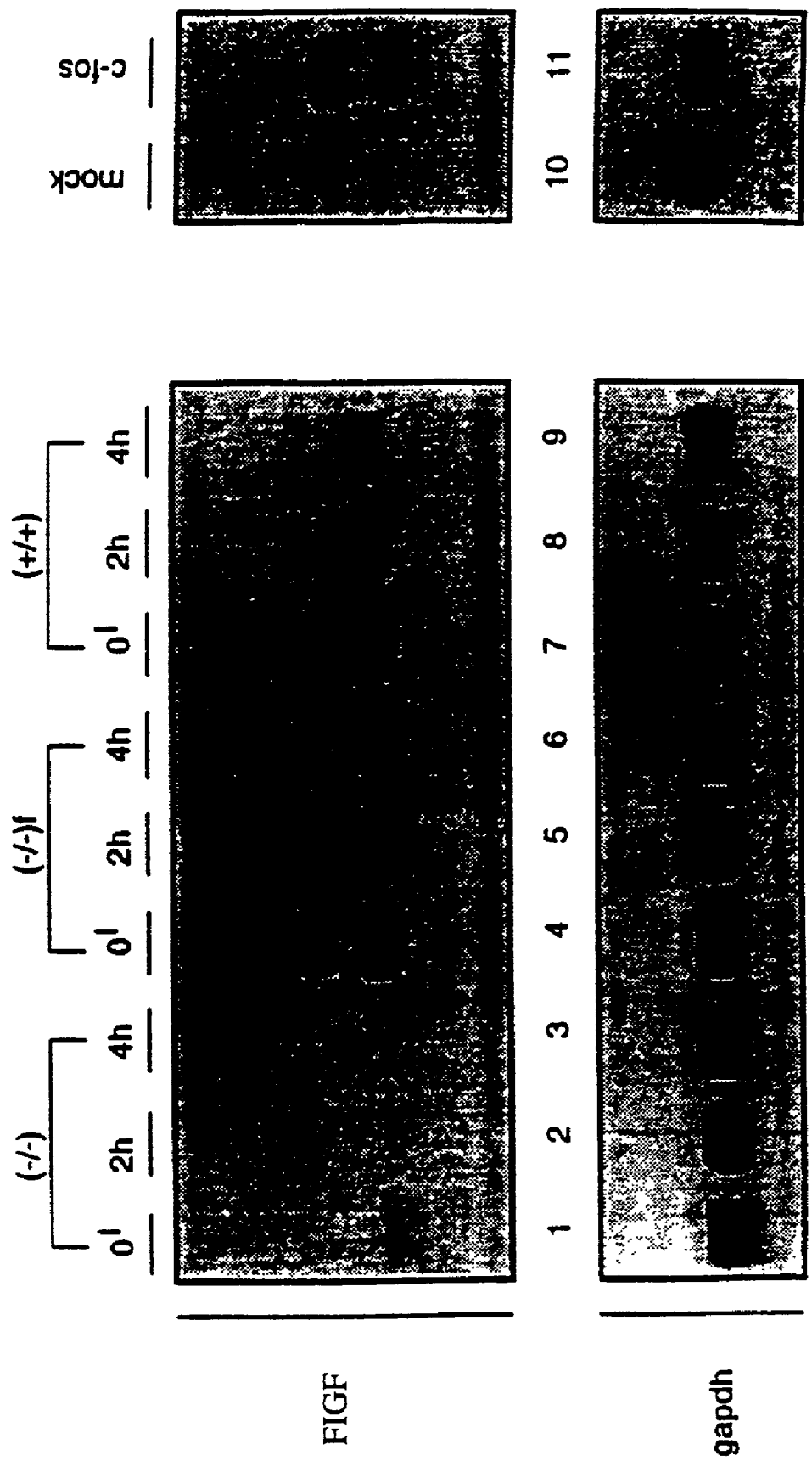

Analysis of FIGF gene expression by Northern blot reveals that the FIGF messenger is barely detectable in c-fos (−/−) fibroblasts, while its expression is high in wild type c-fos (+/+) fibroblasts (FIG. 5A, compare lanes 1-3 with lanes 7-9). FIGF expression is completely restored in stable clones, derived from c-fos (−/−) cells, expressing exogenous c-fos under the control of the FBJ-LTR constitutive promoter (Hu et al. (1994) *EMBO J.* 13: 3094-3103) (FIG. 5A, compare lanes 1-3 with lanes 4-6). The transient transfection of exogenous c-fos results in FIGF induction in c-fos (−/−) cells, although, due to the lower number of transfected cells, the induction observed is less pronounced (FIG. 5A, lanes 10 and 11). Thus, FIGF expression is dependent on c-fos. Moreover, FIGF is not induced by the constitutive AP-1 yeast homologue GCN4. In mammalian cells, GCN4 is able to activate most AP-1 target genes, but it is non-oncogenic. In wild type fibroblasts, c-Fos is the major Fos protein associated with c-Jun or Jun B within the first hour after serum induction. Afterwards c-Fos is not detectable any longer, and it is substituted by FraJ1 and FraJ2 in the AP-1 complex. In c-fos expressing cells, FIGF is highly expressed when cells are kept in low serum conditions and decreases to undetectable levels within six hours after serum induction (FIG. 5A). This pattern of FIGF expression can be observed both in wild type cells and in cells constitutively expressing c-fos (FIG. 5A). Thus, we observe a discrepancy between the expected peak of c-fos expression and the appearance of FIGF, whose messenger accumulates in the quiescent phase. The FIGF pattern of regulation suggests that, besides the expression of c-fos, additional regulatory controls are required for its activation.

Figure 5B:
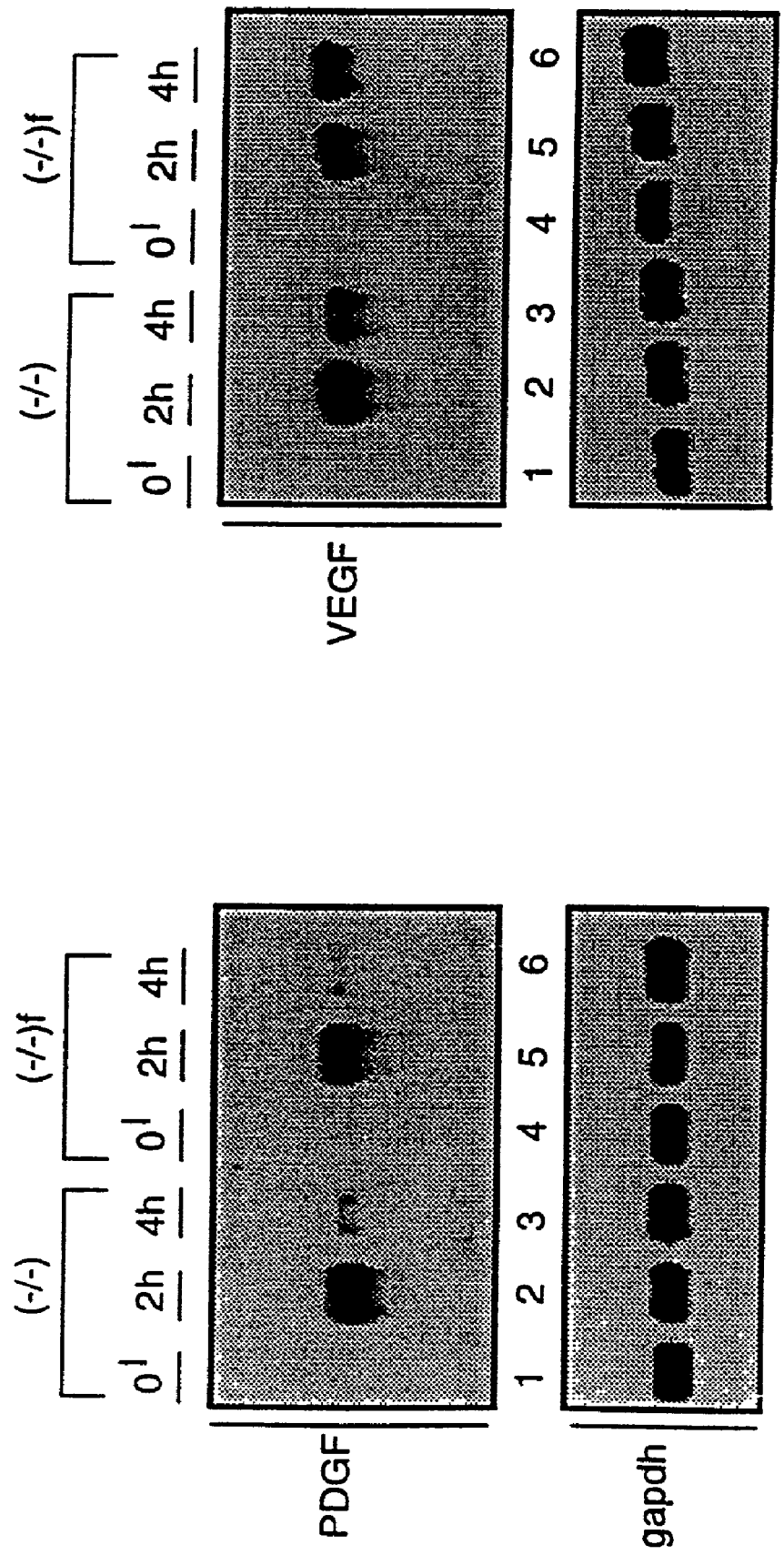

Although FIGF belongs to the PDGF/VEGF family of growth factors, its expression is most similar to the expression of the growth arrest specific (gas) genes. Interestingly, one of them, gas6, acts as a growth factor. Both PDGF and VEGF growth factors are involved in tumor formation (Kim et al. (1993) *Nature* 362:841-844). Moreover, PDGF is the main serum mitogen which induces the transcription activation of c-fos. In order to compare the pattern of expression of these growth factors with respect to FIGF, we measured the PDGF and VEGF messenger levels in fibroblasts differing for the expression of c-fos. As can be observed in FIG. 5B, the regulation of both PDGF and VEGF messengers is distinct from that of FIGF. These growth factors are rapidly induced following serum induction, and their expression is independent of c-fos.

Tumor progression is characterized by morphological changes of the tumor that leads the mutated cells to lose their adhesion to the original neighbors and escape from the tissue of origin. c-fos has been implicated in tumor progression, and its overexpression induces a transformed cell morphology in fibroblasts and epithelial cells. As FIGF is a c-fos-dependent growth factor, it was analyzed whether its over-expression could induce fibroblast morphological transformation. As can be observed in FIG. 7, the constitutive expression of FIGF in fibroblasts induces a transformed phenotype. Stable clones derived from c-fos (−/−) cells, constitutively expressing FIGF, acquire a spindle-shaped morphology, become more refractive, and detach from the plate (FIG. 7, B versus A). On the contrary, stable clones expressing the FIGF antisense messenger acquire a flat and less rifrangent phenotype (FIG. 7C), which is most similar to the phenotype of c-fos (−/−) cells kept in low serum conditions (FIG. 7G). The overexpression of c-fos alters c-fos (−/−) cell morphology similarly to that observed with the over-expression of FIGF, although the phenotye is less pronounced (FIG. 7D). The over-expression of both c-fos and FIGF leads to an extreme phenotype in fibroblasts: cells become longer, disorganized, and lose contacts (FIG. 7E). The expression of the FIGF antisense messenger in cells constitutively expressing c-fos induces a reversion of the transformed phenotype (FIG. 7F). Thus, cells expressing c-fos but depleted of FIGF lose most of the transformed phenotype, suggesting that the morphology observed in cells constitutively expressing c-fos is due to FIGF. Similar morphological alterations are also obtained by cell treatment with purified recombinant FIGF. c-fos fibroblasts, kept in medium containing 0.5% serum for 120 hours, stop growing, become flat, large, and less rifrangent (FIG. 7G). Cell treatment with recombinant FIGF induces the rifrangent, elongated, and non-adherent phenotype (FIG. 7H).

Tumors obtained from cells defective for c-fos cannot undergo malignant progression even if they are carrying the activated v-H-Ras. Thus, the expression of c-fos is essential for the activation of target genes responsible for the malignant phenotype. FIGF is a c-fos-dependent autocrine growth factor able to induce cell division entry and, when it is over-expressed, a transformed phenotype in fibroblasts. The data suggest that the role of c-fos in the activation of the malignant phenotype is due to the activation of FIGF.

Figure 6:
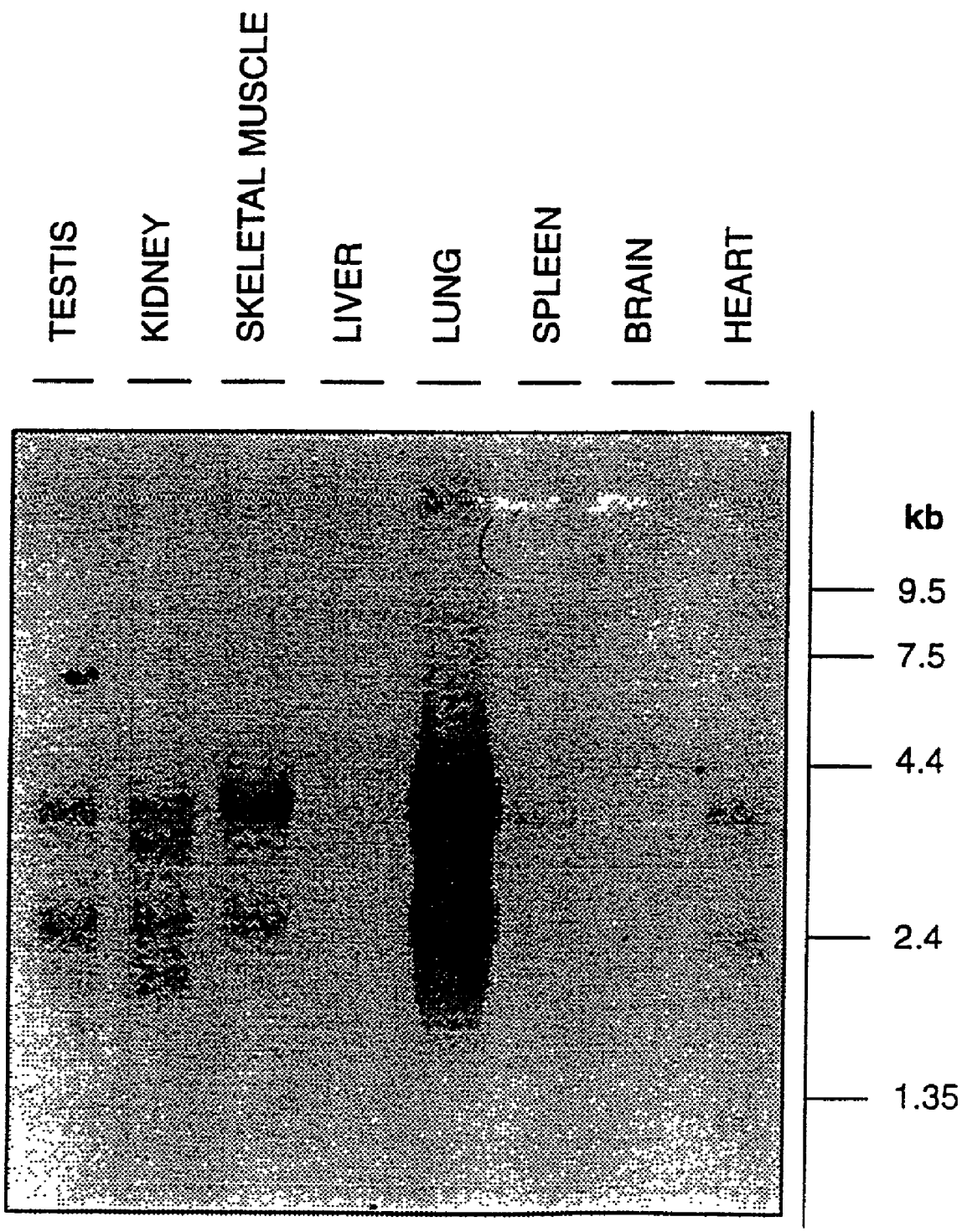

Further experiments on FIGF using a probe specific for FIGF in Northern analysis of RNA derived from mouse tissues show that the FIGF gene is only expressed in cells expressing Fos and poorly in cells that lack the Fos oncogene (FIG. 5). The RNA blot used in the Northern assay was obtained from Clontec. The analysis of its expression in the mouse tissues shows that FIGF is mainly expressed in lung (FIG. 6) and is already present at day 7 of the mouse embryonal life (not shown).

FIGF is therefore a molecule related to the growth factor VEGF, positively regulated by the oncogene Fos. It could be implicated in tumors and in development.

REFERENCES

1. Angel et al. (1988) *Cell* 55:875-885
2. Angel and Karin (1991) *Biochim. Biophys. Acta* 1072:129-57
3. Bauer et al. (1993) *NAR* 21:4272-4280
4. Bergens et al. (1994) *EMBO J.* 13:1176-1188
5. Brenner et al. (1989) *Nature* 337:661-663
6. Cantor et al. (1993) *Proc. Natl. Acad. Sci. USA* 90:10932-10936
7. Curren et al. (1983) *Mol. Cell. BioL* 3:914-921
8. Distel et al. (1987) *Cell* 49:835-844
9. Farrar et al. (1989) *Crit. Rev. Ther. Drug Carrier Syst.* 5:229-261
10. Ferrero et al. (1995) *Human Molecular Genetics* 4:1821-1827
11. Gius et al. (1990) *MoL Cell. Biol.* 10:4243-4255
12. Gurney et al. (1992)*J. Biol. Chem.* 267:18133-18139
13. Hasty et al. (1990) *Arthritis Rheum.* 33:388-397
14. Hay et al. (1989) *Genes Dev.* 3:293-303
15. Heuertz et al. (1993) *Genomics* 18:100-104
16. Holt et al. (1986) *Proc. Natl. Acad. Sci. USA* 831:4794-4798
17. Hu et al. (1994) *EMBO J.* 13:3094-3103
18. Keck et al. (1989) *Science* 246:1309-1311
19. Kerr et al. (1988) *Science* 242:1424-1427
20. Kim et al. (1993) *Nature* 362:841-844
21. Kovary and Bravo (1991) *Mol. Cell. Biol.* 11:2451-2459
22. Kovary and Bravo (1991) *Mol. Cell. Biol.* 11:4466-4472
23. Leung et al. (1989) *Science* 246:1306-1309
24. Liang et al. (1993) *NAR* 21:3269-3275
25. Liotta and Stetler (1990) *Semin. Cancer Biol.* 1:99-106
26. Lord et al. (1993) *Mol. Cell. Biol.* 13:841-851
27. Miller et al. (1984) *Cell* 36:51-60
28. Plate et al. (1993) *Cancer Research* 53:5822-5827
29. Riabowol et al. (1988) *Mol. Cell. Biol.* 8:1670-1676
30. Rollins et al. (1988) *Proc. Natl. Acad. Sci. USA* 85:3738-3742
31. Ruther et al. (1989) *Oncogene* 4:861-865
32. Sambrook et al. (1989) *Molecular Cloning: A Laboratory Manual.* Cold Spring Harbor Laboratory Press, Cold Spring Harbor, N.Y.
33. Sassone et al. (1988) *Nature* 334:314-319
34. Schonthal et al. (1988) *Cell* 54:325-334
35. Schuster et al. (1995) *Brain Res.* 670:14-28
36. Seed and Aruffo (1987) *Proc. Natl. Acad. Sci. USA* 84:3365-3369
37. Superti-Furga et al. (1991) *Proc. Natl. Acad. Sci. USA* 88:5114-5118
38. Takeshita et al. (1994). *J. Clin. Invest.* 93:662-670
39. Tsunoda et al. (1994) *Anti-cancer Res.* 14:2637
40. Vaziri et al. (1995) *Mol. Cell. Biol.* 15:1244-1253
41. Woessner and Gurja (1991) *J. Rheumatol. Suppl.* 27:99-101
42. EP-A-0120693
43. EP-A-0125023

SEQUENCE LISTING

<160> NUMBER OF SEQ ID NOS: 92

<210> SEQ ID NO 1
<211> LENGTH: 1890

```
<212> TYPE: DNA
<213> ORGANISM: Mus Musculus
<220> FEATURE:
<221> NAME/KEY: CDS
<222> LOCATION: (283)..(1359)

<400> SEQUENCE: 1
ggaagatatg accacctcct gattattttt gcagcgggaa actttgaaat atttttcatt      60
gctttctccc atactaagat tgtgtgtgag gcagtgaggg agtcccttga cttactcaag     120
tcatttcatt ggattttaat tacaactgat catgtgattg ttttttttcca tgtaaagttt     180 ggggcttcaa actttgcttc tggagaatgc cttttgcaac acttttcagt agctgcctgg     240
aaacaactgc ttagtcatcg gtagacattt aaaatattca aa atg tat gga gaa        294
                                              Met Tyr Gly Glu
                                                1 tgg gga atg ggg aat atc ctc atg atg ttc cat gtg tac ttg gtg cag       342
Trp Gly Met Gly Asn Ile Leu Met Met Phe His Val Tyr Leu Val Gln
  5              10                  15                  20 ggc ttc agg agc gaa cat gga cca gtg aag gat ttt tct ttt gag cga       390
Gly Phe Arg Ser Glu His Gly Pro Val Lys Asp Phe Ser Phe Glu Arg
             25                  30                  35 tca tcc cgg tcc atg ttg gaa cga tct gaa caa cag atc cga gca gct       438
Ser Ser Arg Ser Met Leu Glu Arg Ser Glu Gln Gln Ile Arg Ala Ala
         40                  45                  50 tct agt ttg gag gag ttg ctg caa atc gcg cac tct gag gac tgg aag       486
Ser Ser Leu Glu Glu Leu Leu Gln Ile Ala His Ser Glu Asp Trp Lys
     55                  60                  65 ctg tgg cga tgc cgg ttg aag ctc aaa agt ctt gcc agt atg gac tca       534
Leu Trp Arg Cys Arg Leu Lys Leu Lys Ser Leu Ala Ser Met Asp Ser
 70                  75                  80 cgc tca gca tcc cat cgc tcc acc aga ttt gcg gca act ttc tat gac       582
Arg Ser Ala Ser His Arg Ser Thr Arg Phe Ala Ala Thr Phe Tyr Asp
 85                  90                  95                 100 act gaa aca cta aaa gtt ata gat gaa gaa tgg cag agg acc caa tgc       630
Thr Glu Thr Leu Lys Val Ile Asp Glu Glu Trp Gln Arg Thr Gln Cys
                105                 110                 115 agc cct aga gag aca tgc gta gaa gtc gcc agt gag ctg ggg aag aca       678
Ser Pro Arg Glu Thr Cys Val Glu Val Ala Ser Glu Leu Gly Lys Thr
            120                 125                 130 acc aac aca ttc ttc aag ccc ccc tgt gta aat gtc ttc cgg tgt gga       726
Thr Asn Thr Phe Phe Lys Pro Pro Cys Val Asn Val Phe Arg Cys Gly
        135                 140                 145 ggc tgc tgc aac gaa gag ggt gtg atg tgt atg aac aca agc acc tcc       774
Gly Cys Cys Asn Glu Glu Gly Val Met Cys Met Asn Thr Ser Thr Ser
    150                 155                 160 tac atc tcc aaa cag ctc ttt gag ata tca gtg cct ctg aca tca gtg       822
Tyr Ile Ser Lys Gln Leu Phe Glu Ile Ser Val Pro Leu Thr Ser Val
165                 170                 175                 180 ccc gag tta gtg cct gtt aaa att gcc aac cat acg ggt tgt aag tgc       870
Pro Glu Leu Val Pro Val Lys Ile Ala Asn His Thr Gly Cys Lys Cys
                185                 190                 195 ttg ccc acg ggc ccc cgc cat cct tac tca att atc aga aga tcc att       918
Leu Pro Thr Gly Pro Arg His Pro Tyr Ser Ile Ile Arg Arg Ser Ile
            200                 205                 210 cag acc cca gaa gaa gat gaa tgt cct cat tcc aag aaa ctc tgt cct       966
Gln Thr Pro Glu Glu Asp Glu Cys Pro His Ser Lys Lys Leu Cys Pro
        215                 220                 225 att gac atg ctg tgg gat aac acc aaa tgt aaa tgt gtt ttg caa gac      1014
Ile Asp Met Leu Trp Asp Asn Thr Lys Cys Lys Cys Val Leu Gln Asp
    230                 235                 240
```

```
gag act cca ctg cct ggg aca gaa gac cac tct tac ctc cag gaa ccc      1062
Glu Thr Pro Leu Pro Gly Thr Glu Asp His Ser Tyr Leu Gln Glu Pro
245                 250                 255                 260 act ctc tgt gga ccg cac atg acg ttt gat gaa gat cgc tgt gag tgc      1110
Thr Leu Cys Gly Pro His Met Thr Phe Asp Glu Asp Arg Cys Glu Cys
                265                 270                 275 gtc tgt aaa gca cca tgt ccg gga gat ctc att cag cac ccg gaa aac      1158
Val Cys Lys Ala Pro Cys Pro Gly Asp Leu Ile Gln His Pro Glu Asn
            280                 285                 290 tgc agt tgc ttt gag tgc aaa gaa agt ctg gag agc tgc tgc caa aag      1206
Cys Ser Cys Phe Glu Cys Lys Glu Ser Leu Glu Ser Cys Cys Gln Lys
        295                 300                 305 cac aag att ttt cac cca gac acc tgc agc tgt gag gac aga tgt cct      1254
His Lys Ile Phe His Pro Asp Thr Cys Ser Cys Glu Asp Arg Cys Pro
    310                 315                 320 ttt cac acc aga aca tgt gca agt aga aag cca gcc tgt gga aag cac      1302
Phe His Thr Arg Thr Cys Ala Ser Arg Lys Pro Ala Cys Gly Lys His
325                 330                 335                 340 tgg cgc ttt cca aag gag aca agg gcc cag gga ctc tac agc cag gag      1350
Trp Arg Phe Pro Lys Glu Thr Arg Ala Gln Gly Leu Tyr Ser Gln Glu
                345                 350                 355 aac cct tga ttcaacttcc tttcaagtcc ccccatctct gtcattttaa              1399
Asn Pro acagctcact gctttgtcaa gttgctgtca ctgttgccca ctaccctgc cccccccct      1459 ccccgcctcc aggtgttaga aaagttgatt tgacctagtg tcatggtaaa gccacatttc    1519
catgcaatgg cggctaggtg attccccagt tcactgacaa atgacttgta gcttcagatg    1579
tctttgcgcc atcagcactc agaaaggaag gggtctgagg agccccttgt tttgatgaat    1639
aagaaaaggt tgcctgaaac agagtagtag gtgccactcg attggttcct cgggctggca    1699
aagtccaagg gcaatgctca tgagttattg tgcttctttc ttatgcggaa tttcatttgt    1759
atgatcagca ctgatcaatt cccattccac ttgtactttt taggtttact gaagcactgc    1819
ctgatgtttt atatgtaaat gtatttaaag gaaataaaca ctgttatgca gcccacaaaa    1879
aaaaaaaaaa a                                                         1890
```

<210> SEQ ID NO 2
<211> LENGTH: 358
<212> TYPE: PRT
<213> ORGANISM: Mus Musculus

<400> SEQUENCE: 2

```
Met Tyr Gly Glu Trp Gly Met Gly Asn Ile Leu Met Met Phe His Val
1               5                   10                  15

Tyr Leu Val Gln Gly Phe Arg Ser Glu His Gly Pro Val Lys Asp Phe
            20                  25                  30

Ser Phe Glu Arg Ser Ser Arg Ser Met Leu Glu Arg Ser Glu Gln Gln
        35                  40                  45

Ile Arg Ala Ala Ser Leu Glu Glu Leu Leu Gln Ile Ala His Ser
    50                  55                  60

Glu Asp Trp Lys Leu Trp Arg Cys Arg Leu Lys Leu Lys Ser Leu Ala
65                  70                  75                  80

Ser Met Asp Ser Arg Ser Ala Ser His Arg Ser Thr Arg Phe Ala Ala
                85                  90                  95

Thr Phe Tyr Asp Thr Glu Thr Leu Lys Val Ile Asp Glu Glu Trp Gln
            100                 105                 110

Arg Thr Gln Cys Ser Pro Arg Glu Thr Cys Val Glu Val Ala Ser Glu
        115                 120                 125
```

```
Leu Gly Lys Thr Thr Asn Thr Phe Phe Lys Pro Pro Cys Val Asn Val
    130                 135                 140

Phe Arg Cys Gly Gly Cys Cys Asn Glu Glu Gly Val Met Cys Met Asn
145                 150                 155                 160

Thr Ser Thr Ser Tyr Ile Ser Lys Gln Leu Phe Glu Ile Ser Val Pro
                165                 170                 175

Leu Thr Ser Val Pro Glu Leu Val Pro Val Lys Ile Ala Asn His Thr
            180                 185                 190

Gly Cys Lys Cys Leu Pro Thr Gly Pro Arg His Pro Tyr Ser Ile Ile
        195                 200                 205

Arg Arg Ser Ile Gln Thr Pro Glu Glu Asp Glu Cys Pro His Ser Lys
    210                 215                 220

Lys Leu Cys Pro Ile Asp Met Leu Trp Asp Asn Thr Cys Lys Cys
225                 230                 235                 240

Val Leu Gln Asp Glu Thr Pro Leu Pro Gly Thr Glu Asp His Ser Tyr
                245                 250                 255

Leu Gln Glu Pro Thr Leu Cys Gly Pro His Met Thr Phe Asp Glu Asp
            260                 265                 270

Arg Cys Glu Cys Val Cys Lys Ala Pro Cys Pro Gly Asp Leu Ile Gln
        275                 280                 285

His Pro Glu Asn Cys Ser Cys Phe Glu Cys Lys Glu Ser Leu Glu Ser
    290                 295                 300

Cys Cys Gln Lys His Lys Ile Phe His Pro Thr Cys Ser Cys Glu
305                 310                 315                 320

Asp Arg Cys Pro Phe His Thr Arg Thr Cys Ala Ser Arg Lys Pro Ala
                325                 330                 335

Cys Gly Lys His Trp Arg Phe Pro Lys Glu Thr Arg Ala Gln Gly Leu
            340                 345                 350

Tyr Ser Gln Glu Asn Pro
        355

<210> SEQ ID NO 3
<211> LENGTH: 1864
<212> TYPE: DNA
<213> ORGANISM: Homo sapiens
<220> FEATURE:
<221> NAME/KEY: CDS
<222> LOCATION: (218)..(1306)

<400> SEQUENCE: 3
ggcacgaggt ttttttttt tttttcatc tctctctccc caccccctaag attgtgcaaa    60 aaaagcgtac cttgcctaat tgaaataatt tcattggatt ttgatcagaa ctgattattt   120
ggttttctgt gtgaagtttt gaggtttcaa actttccttc tggagaatgc cttttgaaac   180
aattttctct agctgcctga tgtcaactgc ttagtaa tca gtg gat att gaa ata    235
                                         Ser Val Asp Ile Glu Ile
                                           1               5 ttc aaa atg tac aga gag tgg gta gtg gtg aat gtt ttc atg atg ttg    283
Phe Lys Met Tyr Arg Glu Trp Val Val Val Asn Val Phe Met Met Leu
         10                  15                  20 tac gtc cag ctg gtg cag ggc tcc agt aat gaa cat gga cca gtg aag    331
Tyr Val Gln Leu Val Gln Gly Ser Ser Asn Glu His Gly Pro Val Lys
     25                  30                  35 cga tca tct cag tcc aca ttg gaa cga tct gaa cag cag atc agg gct    379
Arg Ser Ser Gln Ser Thr Leu Glu Arg Ser Glu Gln Gln Ile Arg Ala
 40                  45                  50 gct tct agt ttg gag gaa cta ctt cga att act cac tct gag gac tgg    427
```

```
                Ala Ser Ser Leu Glu Glu Leu Leu Arg Ile Thr His Ser Glu Asp Trp
                55              60                  65              70 aag ctg tgg aga tgc agg ctg agg ctc aaa agt ttt acc agt atg gac                475
Lys Leu Trp Arg Cys Arg Leu Arg Leu Lys Ser Phe Thr Ser Met Asp
                75                  80                  85 tct cgc tca gca tcc cat cgg tcc act agg ttt gcg gca act ttc tat                523
Ser Arg Ser Ala Ser His Arg Ser Thr Arg Phe Ala Ala Thr Phe Tyr
                90                  95                  100 gac att gaa aca cta aaa gtt ata gat gaa gaa tgg caa aga act cag                571
Asp Ile Glu Thr Leu Lys Val Ile Asp Glu Glu Trp Gln Arg Thr Gln
            105                 110                 115 tgc agc cct aga gaa acg tgc gtg gag gtg gcc agt gag ctg ggg aag                619
Cys Ser Pro Arg Glu Thr Cys Val Glu Val Ala Ser Glu Leu Gly Lys
        120                 125                 130 agt acc aac aca ttc ttc aag ccc cct tgt gtg aac gtg ttc cga tgt                667
Ser Thr Asn Thr Phe Phe Lys Pro Pro Cys Val Asn Val Phe Arg Cys
135                 140                 145                 150 ggt ggt tgt tgc aat gaa gag agc ttt atg tgt atg aac acc agc acc                715
Gly Gly Cys Cys Asn Glu Glu Ser Phe Met Cys Met Asn Thr Ser Thr
                155                 160                 165 tcg tac att tcc aaa cag ctc ttt gag ata tca gtg cct ttg aca tca                763
Ser Tyr Ile Ser Lys Gln Leu Phe Glu Ile Ser Val Pro Leu Thr Ser
            170                 175                 180 gta cct gaa tta gtg cct gtt aaa gtt gcc aat cat aca ggt tgt aag                811
Val Pro Glu Leu Val Pro Val Lys Val Ala Asn His Thr Gly Cys Lys
        185                 190                 195 tgc ttg cca aca gcc ccc cgc cat cca tac tca att atc aga aga tcc                859
Cys Leu Pro Thr Ala Pro Arg His Pro Tyr Ser Ile Ile Arg Arg Ser
200                 205                 210 atc cag atc cct gaa gaa gat cgc tgt tcc cat tcc aag aaa ctc tgt                907
Ile Gln Ile Pro Glu Glu Asp Arg Cys Ser His Ser Lys Lys Leu Cys
215                 220                 225                 230 cct att gac atg cta tgg gat agc aac aaa tgt aaa tgt gtt ttg cag                955
Pro Ile Asp Met Leu Trp Asp Ser Asn Lys Cys Lys Cys Val Leu Gln
                235                 240                 245 gag gaa aat cca ctt gct gga aca gaa gac cac tct cat ctc cag gaa                1003
Glu Glu Asn Pro Leu Ala Gly Thr Glu Asp His Ser His Leu Gln Glu
            250                 255                 260 cca gct ctc tgt ggg cca cac atg atg ttt gac gaa gat cgt tgc gag                1051
Pro Ala Leu Cys Gly Pro His Met Met Phe Asp Glu Asp Arg Cys Glu
        265                 270                 275 tgt gtc tgt aaa aca cca tgt ccc aaa gat cta atc cag cac ccc aaa                1099
Cys Val Cys Lys Thr Pro Cys Pro Lys Asp Leu Ile Gln His Pro Lys
    280                 285                 290 aac tgc agt tgc ttt gag tgc aaa gaa agt ctg gag acc tgc tgc cag                1147
Asn Cys Ser Cys Phe Glu Cys Lys Glu Ser Leu Glu Thr Cys Cys Gln
295                 300                 305                 310 aag cac aag cta ttt cac cca gac acc tgc agc tgt gag gac aga tgc                1195
Lys His Lys Leu Phe His Pro Asp Thr Cys Ser Cys Glu Asp Arg Cys
                315                 320                 325 ccc ttt cat acc aga cca tgt gca agt ggc aaa aca gca tgt gca aag                1243
Pro Phe His Thr Arg Pro Cys Ala Ser Gly Lys Thr Ala Cys Ala Lys
            330                 335                 340 cat tgc cgc ttt cca aag gag aaa agg gct gcc cag ggg ccc cac agc                1291
His Cys Arg Phe Pro Lys Glu Lys Arg Ala Ala Gln Gly Pro His Ser
        345                 350                 355 cga aag aat cct tga ttcagcgttc caagttcccc atccctgtca ttttttaacag              1346
Arg Lys Asn Pro
    360 catgctgctt tgccaagttg ctgtcactgt ttttttccca ggtgttaaaa aaaaaatcca              1406
```

```
ttttacacag caccacagtg aatccagacc aaccttccat tcacaccagc taaggagtcc    1466
ctggttcatt gatggatgtc ttctagctgc agatgcctct gcgcaccaag gaatggagag    1526
gaggggaccc atgtaatcct tttgtttagt tttgtttttg tttttggtg aatgagaaag     1586 gtgtgctggt catggaatgg caggtgtcat atgactgatt actcagagca gatgaggaaa    1646
actgtagtct ctgagtcctt tgctaatcgc aactcttgtg aattattctg attcttttt     1706 atgcagaatt tgattcgtat gatcagtact gactttctga ttactgtcca gcttatagtc    1766
ttccagttta atgaactacc atctgatgtt tcatatttaa gtgtatttaa agaaaataaa    1826
caccattatt caagccatat aaaaaaaaaa aaaaaaaa                            1864
```

<210> SEQ ID NO 4
<211> LENGTH: 362
<212> TYPE: PRT
<213> ORGANISM: Homo sapiens

<400> SEQUENCE: 4

```
Ser Val Asp Ile Glu Ile Phe Lys Met Tyr Arg Glu Trp Val Val
1               5                   10                  15

Asn Val Phe Met Met Leu Tyr Val Gln Leu Val Gln Gly Ser Ser Asn
            20                  25                  30

Glu His Gly Pro Val Lys Arg Ser Ser Gln Ser Thr Leu Glu Arg Ser
        35                  40                      45

Glu Gln Gln Ile Arg Ala Ala Ser Ser Leu Glu Glu Leu Leu Arg Ile
    50                  55                  60

Thr His Ser Glu Asp Trp Lys Leu Trp Arg Cys Arg Leu Arg Leu Lys
65              70                  75                  80

Ser Phe Thr Ser Met Asp Ser Arg Ser Ala Ser His Arg Ser Thr Arg
                85                  90                  95

Phe Ala Ala Thr Phe Tyr Asp Ile Glu Thr Leu Lys Val Ile Asp Glu
            100                 105                 110

Glu Trp Gln Arg Thr Gln Cys Ser Pro Arg Glu Thr Cys Val Glu Val
        115                 120                 125

Ala Ser Glu Leu Gly Lys Ser Thr Asn Thr Phe Phe Lys Pro Pro Cys
    130                 135                 140

Val Asn Val Phe Arg Cys Gly Gly Cys Cys Asn Glu Glu Ser Phe Met
145                 150                 155                 160

Cys Met Asn Thr Ser Thr Ser Tyr Ile Ser Lys Gln Leu Phe Glu Ile
                165                 170                 175

Ser Val Pro Leu Thr Ser Val Pro Glu Leu Val Pro Val Lys Val Ala
            180                 185                 190

Asn His Thr Gly Cys Lys Cys Leu Pro Thr Ala Pro Arg His Pro Tyr
        195                 200                 205

Ser Ile Ile Arg Arg Ser Ile Gln Ile Pro Glu Glu Asp Arg Cys Ser
    210                 215                 220

His Ser Lys Lys Leu Cys Pro Ile Asp Met Leu Trp Asp Ser Asn Lys
225                 230                 235                 240

Cys Lys Cys Val Leu Gln Glu Glu Asn Pro Leu Ala Gly Thr Glu Asp
                245                 250                 255

His Ser His Leu Gln Glu Pro Ala Leu Cys Gly Pro His Met Met Phe
            260                 265                 270

Asp Glu Asp Arg Cys Glu Cys Val Cys Lys Thr Pro Cys Pro Lys Asp
        275                 280                 285

Leu Ile Gln His Pro Lys Asn Cys Ser Cys Phe Glu Cys Lys Glu Ser
```

```
                290                   295                   300
Leu Glu Thr Cys Cys Gln Lys His Lys Leu Phe His Pro Asp Thr Cys
305                 310                 315                 320

Ser Cys Glu Asp Arg Cys Pro Phe His Thr Arg Pro Cys Ala Ser Gly
                325                 330                 335

Lys Thr Ala Cys Ala Lys His Cys Arg Phe Pro Lys Glu Lys Arg Ala
                340                 345                 350

Ala Gln Gly Pro His Ser Arg Lys Asn Pro
            355                 360

<210> SEQ ID NO 5
<211> LENGTH: 48
<212> TYPE: PRT
<213> ORGANISM: Homo sapiens
<220> FEATURE:
<221> NAME/KEY: PEPTIDE
<222> LOCATION: (1)..(48)
<223> OTHER INFORMATION: Segment of FIGF

<400> SEQUENCE: 5

Thr Leu Lys Val Ile Asp Glu Glu Trp Gln Arg Thr Gln Cys Ser Pro
1               5                   10                  15

Arg Glu Thr Cys Val Glu Val Ala Ser Glu Leu Gly Lys Thr Thr Asn
                20                  25                  30

Thr Phe Phe Lys Pro Pro Cys Val Asn Val Phe Arg Cys Gly Gly Cys
            35                  40                  45

<210> SEQ ID NO 6
<211> LENGTH: 48
<212> TYPE: PRT
<213> ORGANISM: Unknown
<220> FEATURE:
<223> OTHER INFORMATION: Mammalian
<220> FEATURE:
<221> NAME/KEY: PEPTIDE
<222> LOCATION: (1)..(48)
<223> OTHER INFORMATION: Segment of VEGF-C

<400> SEQUENCE: 6

Ile Leu Lys Ser Ile Asp Asn Glu Trp Arg Lys Thr Gln Cys Met Pro
1               5                   10                  15

Arg Glu Val Cys Ile Asp Val Gly Lys Glu Phe Gly Val Ala Thr Asn
                20                  25                  30

Thr Phe Phe Lys Pro Pro Cys Val Ser Val Tyr Arg Cys Gly Gly Cys
            35                  40                  45

<210> SEQ ID NO 7
<211> LENGTH: 48
<212> TYPE: PRT
<213> ORGANISM: Unknown
<220> FEATURE:
<223> OTHER INFORMATION: Mammalian
<220> FEATURE:
<221> NAME/KEY: PEPTIDE
<222> LOCATION: (1)..(48)
<223> OTHER INFORMATION: Segment of VEGF

<400> SEQUENCE: 7

Glu Val Val Lys Phe Met Asp Val Tyr Gln Arg Ser Tyr Cys His Pro
1               5                   10                  15

Ile Glu Thr Leu Val Asp Ile Phe Gln Glu Tyr Pro Asp Glu Ile Glu
                20                  25                  30

Tyr Ile Phe Lys Pro Ser Cys Val Pro Leu Met Arg Cys Gly Gly Cys
            35                  40                  45
```

<210> SEQ ID NO 8
<211> LENGTH: 48
<212> TYPE: PRT
<213> ORGANISM: Unknown
<220> FEATURE:
<223> OTHER INFORMATION: Mammalian
<220> FEATURE:
<221> NAME/KEY: PEPTIDE
<222> LOCATION: (1)..(48)
<223> OTHER INFORMATION: Segment of PIGF

<400> SEQUENCE: 8

Glu Val Val Pro Phe Gln Glu Val Trp Gly Arg Ser Tyr Cys Arg Ala
1               5                   10                  15

Leu Glu Arg Leu Val Asp Val Val Ser Glu Tyr Pro Ser Glu Val Glu
            20                  25                  30

His Met Phe Ser Pro Ser Cys Val Ser Leu Leu Arg Cys Thr Gly Cys
        35                  40                  45

<210> SEQ ID NO 9
<211> LENGTH: 50
<212> TYPE: PRT
<213> ORGANISM: Unknown
<220> FEATURE:
<223> OTHER INFORMATION: Mammalian
<220> FEATURE:
<221> NAME/KEY: PEPTIDE
<222> LOCATION: (1)..(50)
<223> OTHER INFORMATION: Segment of PDGF-B

<400> SEQUENCE: 9

Gly Ser Leu Thr Ile Ala Glu Pro Ala Met Ile Ala Glu Cys Lys Thr
1               5                   10                  15

Arg Thr Glu Val Phe Glu Ile Ser Arg Arg Leu Ile Asp Arg Thr Asn
            20                  25                  30

Ala Asn Phe Leu Val Trp Pro Pro Cys Val Glu Val Gln Arg Cys Ser
        35                  40                  45

Gly Cys
    50

<210> SEQ ID NO 10
<211> LENGTH: 50
<212> TYPE: PRT
<213> ORGANISM: Unknown
<220> FEATURE:
<223> OTHER INFORMATION: Mammalian
<220> FEATURE:
<221> NAME/KEY: PEPTIDE
<222> LOCATION: (1)..(50)
<223> OTHER INFORMATION: Segment of PDGF-A

<400> SEQUENCE: 10

Arg Arg Lys Arg Ser Ile Glu Glu Ala Val Pro Ala Val Cys Lys Thr
1               5                   10                  15

Arg Thr Val Ile Tyr Glu Ile Pro Arg Ser Gln Val Asp Pro Thr Ser
            20                  25                  30

Ala Asn Phe Leu Ile Trp Pro Pro Cys Val Glu Val Lys Arg Cys Thr
        35                  40                  45

Gly Cys
    50

<210> SEQ ID NO 11
<211> LENGTH: 49
<212> TYPE: PRT

```
<213> ORGANISM: Homo sapiens
<220> FEATURE:
<221> NAME/KEY: PEPTIDE
<222> LOCATION: (1)..(49)
<223> OTHER INFORMATION: Segment of FIGF

<400> SEQUENCE: 11

Cys Asn Glu Glu Gly Val Met Cys Met Asn Thr Ser Thr Ser Tyr Ile
 1               5                  10                  15

Ser Lys Gln Leu Phe Glu Ile Ser Val Pro Leu Thr Ser Val Pro Glu
             20                  25                  30

Leu Val Pro Val Lys Ile Ala Asn His Thr Gly Cys Lys Cys Leu Pro
         35                  40                  45

Thr

<210> SEQ ID NO 12
<211> LENGTH: 49
<212> TYPE: PRT
<213> ORGANISM: Unknown
<220> FEATURE:
<223> OTHER INFORMATION: Mammalian
<220> FEATURE:
<221> NAME/KEY: PEPTIDE
<222> LOCATION: (1)..(49)
<223> OTHER INFORMATION: Segment of VEGF-C

<400> SEQUENCE: 12

Cys Asn Ser Glu Gly Leu Gln Cys Met Asn Thr Ser Thr Ser Tyr Leu
 1               5                  10                  15

Ser Lys Thr Leu Phe Glu Ile Thr Val Pro Leu Ser Gln Gly Pro Lys
             20                  25                  30

Pro Val Thr Ile Ser Phe Ala Asn His Thr Ser Cys Arg Cys Met Ser
         35                  40                  45

Lys

<210> SEQ ID NO 13
<211> LENGTH: 47
<212> TYPE: PRT
<213> ORGANISM: Unknown
<220> FEATURE:
<223> OTHER INFORMATION: Mammalian
<220> FEATURE:
<221> NAME/KEY: PEPTIDE
<222> LOCATION: (1)..(47)
<223> OTHER INFORMATION: Segment of VEGF

<400> SEQUENCE: 13

Cys Asn Asp Glu Gly Leu Glu Cys Val Pro Thr Glu Glu Ser Asn Ile
 1               5                  10                  15

Thr Met Gln Ile Met Arg Ile Lys Pro His Gln Gly Gln His Ile Gly
             20                  25                  30

Glu Met Ser Phe Leu Gln His Asn Lys Cys Glu Cys Arg Pro Lys
         35                  40                  45

<210> SEQ ID NO 14
<211> LENGTH: 47
<212> TYPE: PRT
<213> ORGANISM: Unknown
<220> FEATURE:
<223> OTHER INFORMATION: Mammalian
<220> FEATURE:
<221> NAME/KEY: PEPTIDE
<222> LOCATION: (1)..(47)
<223> OTHER INFORMATION: Segment of PlGF

<400> SEQUENCE: 14
```

Cys Gly Asp Glu Asn Leu His Cys Val Pro Val Glu Thr Ala Asn Val
1               5                   10                  15

Thr Met Gln Leu Leu Lys Ile Arg Ser Gly Asp Arg Pro Ser Tyr Val
            20                  25                  30

Glu Leu Thr Phe Ser Gln His Val Arg Cys Glu Cys Arg Pro Leu
        35                  40                  45

<210> SEQ ID NO 15
<211> LENGTH: 50
<212> TYPE: PRT
<213> ORGANISM: Unknown
<220> FEATURE:
<223> OTHER INFORMATION: Mammalian
<220> FEATURE:
<221> NAME/KEY: PEPTIDE
<222> LOCATION: (1)..(50)
<223> OTHER INFORMATION: Segment of PDGF-B

<400> SEQUENCE: 15

Cys Asn Asn Arg Asn Val Gln Cys Arg Pro Thr Gln Val Gln Leu Arg
1               5                   10                  15

Pro Val Gln Val Arg Lys Ile Glu Ile Val Arg Lys Lys Pro Ile Phe
            20                  25                  30

Lys Lys Ala Thr Val Thr Leu Glu Asp His Leu Ala Cys Lys Cys Glu
        35                  40                  45

Thr Val
    50

<210> SEQ ID NO 16
<211> LENGTH: 50
<212> TYPE: PRT
<213> ORGANISM: Unknown
<220> FEATURE:
<223> OTHER INFORMATION: Mammalian
<220> FEATURE:
<221> NAME/KEY: PEPTIDE
<222> LOCATION: (1)..(50)
<223> OTHER INFORMATION: Segment of PDGF-A

<400> SEQUENCE: 16

Cys Asn Thr Ser Ser Val Lys Cys Gln Pro Ser Arg Val His His Arg
1               5                   10                  15

Ser Val Lys Val Ala Lys Val Glu Tyr Val Arg Lys Lys Pro Lys Leu
            20                  25                  30

Lys Glu Val Gln Val Arg Leu Glu Glu His Leu Glu Cys Ala Cys Ala
        35                  40                  45

Thr Thr
    50

<210> SEQ ID NO 17
<211> LENGTH: 1864
<212> TYPE: DNA
<213> ORGANISM: Homo sapiens
<220> FEATURE:
<221> NAME/KEY: CDS
<222> LOCATION: (1)..(1860)
<223> OTHER INFORMATION: Alternate reading frame

<400> SEQUENCE: 17 ggc acg agg ttt ttt ttt ttt ttt ttc atc tct ctc tcc cca ccc cta        48
Gly Thr Arg Phe Phe Phe Phe Phe Phe Ile Ser Leu Ser Pro Pro Leu
1               5                   10                  15 aga ttg tgc aaa aaa agc gta cct tgc cta att gaa ata att tca ttg        96
Arg Leu Cys Lys Lys Ser Val Pro Cys Leu Ile Glu Ile Ile Ser Leu

```
                  20                      25                      30
gat ttt gat cag aac tga tta ttt ggt ttt ctg tgt gaa gtt ttg agg     144
Asp Phe Asp Gln Asn     Leu Phe Gly Phe Leu Cys Glu Val Leu Arg
             35                      40                      45 ttt caa act ttc ctt ctg gag aat gcc ttt tga aac aat ttt ctc tag     192
Phe Gln Thr Phe Leu Leu Glu Asn Ala Phe     Asn Asn Phe Leu
             50                      55                      60 ctg cct gat gtc aac tgc tta gta atc agt gga tat tga aat att caa     240
Leu Pro Asp Val Asn Cys Leu Val Ile Ser Gly Tyr     Asn Ile Gln
             65                      70                      75 aat gta cag aga gtg ggt agt ggt gaa tgt ttt cat gat gtt gta cgt     288
Asn Val Gln Arg Val Gly Ser Gly Glu Cys Phe His Asp Val Val Arg
             80                      85                      90 cca gct ggt gca ggg ctc cag taa tga aca tgg acc agt gaa gcg atc     336
Pro Ala Gly Ala Gly Leu Gln         Thr Trp Thr Ser Glu Ala Ile
             95                     100                     105 atc tca gtc cac att gga acg atc tga aca gca gat cag ggc tgc ttc     384
Ile Ser Val His Ile Gly Thr Ile     Thr Ala Asp Gln Gly Cys Phe
            110                     115                     120 tag ttt gga gga act act tcg aat tac tca ctc tga gga ctg gaa gct     432
    Phe Gly Gly Thr Thr Ser Asn Tyr Ser Leu     Gly Leu Glu Ala
            125                     130                     135 gtg gag atg cag gct gag gct caa aag ttt tac cag tat gga ctc tcg     480
Val Glu Met Gln Ala Glu Ala Gln Lys Phe Tyr Gln Tyr Gly Leu Ser
            140                     145                     150 ctc agc atc cca tcg gtc cac tag gtt tgc ggc aac ttt cta tga cat     528
Leu Ser Ile Pro Ser Val His     Val Cys Gly Asn Phe Leu     His
            155                     160                     165 tga aac act aaa agt tat aga tga aga atg gca aag aac tca gtg cag     576
    Asn Thr Lys Ser Tyr Arg     Arg Met Ala Lys Asn Ser Val Gln
            170                     175 ccc tag aga aac gtg cgt gga ggt ggc cag tga gct ggg gaa gag tac     624
Pro     Arg Asn Val Arg Gly Gly Gly Gln     Ala Gly Glu Glu Tyr
180                     185                     190 caa cac att ctt caa gcc ccc ttg tgt gaa cgt gtt ccg atg tgg tgg     672
Gln His Ile Leu Gln Ala Pro Leu Cys Glu Arg Val Pro Met Trp Trp
            195                     200                     205 ttg ttg caa tga aga gag ctt tat gtg tat gaa cac cag cac ctc gta     720
Leu Leu Gln     Arg Glu Leu Tyr Val Tyr Glu His Gln His Leu Val
210                     215                     220 cat ttc caa aca gct ctt tga gat atc agt gcc ttt gac atc agt acc     768
His Phe Gln Thr Ala Leu     Asp Ile Ser Ala Phe Asp Ile Ser Thr
225                     230                     235 tga att agt gcc tgt taa agt tgc caa tca tac agg ttg taa gtg ctt     816
    Ile Ser Ala Cys     Ser Cys Gln Ser Tyr Arg Leu     Val Leu
        240                     245                     250 gcc aac agc ccc ccg cca tcc ata ctc aat tat cag aag atc cat cca     864
Ala Asn Ser Pro Pro Pro Ser Ile Leu Asn Tyr Gln Lys Ile His Pro
            255                     260                     265 gat ccc tga aga aga tcg ctg ttc cca ttc aa gaa act ctg tcc tat     912
Asp Pro     Arg Arg Ser Leu Phe Pro Phe Gln Glu Thr Leu Ser Tyr
270                     275                     280 tga cat gct atg gga tag caa caa atg taa atg tgt ttt gca gga gga     960
    His Ala Met Gly     Gln Gln Met     Met Cys Phe Ala Gly Gly
            285                     290                     295 aaa tcc act tgc tgg aac aga aga cca ctc tca tct cca gga acc agc    1008
Lys Ser Thr Cys Trp Asn Arg Arg Pro Leu Ser Ser Pro Gly Thr Ser
            300                     305                     310 tct ctg tgg gcc aca cat gat gtt tga cga aga tcg ttg cga gtg tgt    1056
Ser Leu Trp Ala Thr His Asp Val     Arg Arg Ser Leu Arg Val Cys
```

```
                 315                 320                 325
ctg taa aac acc atg tcc caa aga tct aat cca gca ccc caa aaa ctg    1104
Leu     Asn Thr Met Ser Gln Arg Ser Asn Pro Ala Pro Gln Lys Leu
            330                 335                 340 cag ttg ctt tga gtg caa aga aag tct gga gac ctg ctg cca gaa gca    1152
Gln Leu Leu     Val Gln Arg Lys Ser Gly Asp Leu Leu Pro Glu Ala
        345                 350                 355 caa gct att tca ccc aga cac ctg cag ctg tga gga cag atg ccc ctt    1200
Gln Ala Ile Ser Pro Arg His Leu Gln Leu     Gly Gln Met Pro Leu
        360                 365                 370 tca tac cag acc atg tgc aag tgg caa aac agc atg tgc aaa gca ttg    1248
Ser Tyr Gln Thr Met Cys Lys Trp Gln Asn Ser Met Cys Lys Ala Leu
        375                 380                 385 ccg ctt tcc aaa gga gaa aag ggc tgc cca ggg gcc cca cag ccg aaa    1296
Pro Leu Ser Lys Gly Glu Lys Gly Cys Pro Gly Ala Pro Gln Pro Lys
        390                 395                 400 gaa tcc ttg att cag cgt tcc aag ttc ccc atc cct gtc att ttt aac    1344
Glu Ser Leu Ile Gln Arg Ser Lys Phe Pro Ile Pro Val Ile Phe Asn
405                 410                 415                 420 agc atg ctg ctt tgc caa gtt gct gtc act gtt ttt tca cca ggt gtt    1392
Ser Met Leu Leu Cys Gln Val Ala Val Thr Val Phe Phe Pro Gly Val
                425                 430                 435 aaa aaa aaa atc cat ttt aca cag cac cac agt gaa tcc aga cca acc    1440
Lys Lys Lys Ile His Phe Thr Gln His His Ser Glu Ser Arg Pro Thr
            440                 445                 450 ttc cat tca cac cag cta agg agt ccc tgg ttc att gat gga tgt ctt    1488
Phe His Ser His Gln Leu Arg Ser Pro Trp Phe Ile Asp Gly Cys Leu
        455                 460                 465 cta gct gca gat gcc tct gcg cac caa gga atg gag agg agg gga ccc    1536
Leu Ala Ala Asp Ala Ser Ala His Gln Gly Met Glu Arg Arg Gly Pro
470                 475                 480 atg taa tcc ttt tgt tta gtt ttg ttt ttg ttt ttt ggt gaa tga gaa    1584
Met     Ser Phe Cys Leu Val Leu Phe Leu Phe Phe Gly Glu     Glu
485                 490                 495 agg tgt gct ggt cat gga atg gca ggt gtc ata tga ctg att act cag    1632
Arg Cys Ala Gly His Gly Met Ala Gly Val Ile     Leu Ile Thr Gln
        500                 505                 510 agc aga tga gga aaa ctg tag tct ctg agt cct ttg cta atc gca act    1680
Ser Arg     Gly Lys Leu     Ser Leu Ser Pro Leu Leu Ile Ala Thr
        515                 520                 525 ctt gtg aat tat tct gat tct ttt tta tgc aga att tga ttc gta tga    1728
Leu Val Asn Tyr Ser Asp Ser Phe Leu Cys Arg Ile     Phe Val
        530                 535                 540 tca gta ctg act ttc tga tta ctg tcc agc tta tag tct tcc agt tta    1776
Ser Val Leu Thr Phe     Leu Leu Ser Ser Leu     Ser Ser Ser Leu
        545                 550                 555 atg aac tac cat ctg atg ttt cat att taa gtg tat tta aag aaa ata    1824
Met Asn Tyr His Leu Met Phe His Ile     Val Tyr Leu Lys Lys Ile
        560                 565                 570 aac acc att att caa gcc ata taa aaa aaa aaa aaaa                   1864
Asn Thr Ile Ile Gln Ala Ile     Lys Lys Lys Lys
        575                 580

<210> SEQ ID NO 18
<211> LENGTH: 37
<212> TYPE: PRT
<213> ORGANISM: Homo sapiens

<400> SEQUENCE: 18

Gly Thr Arg Phe Phe Phe Phe Phe Ile Ser Leu Ser Pro Pro Leu
1               5                   10                  15
```

-continued

Arg Leu Cys Lys Lys Ser Val Pro Cys Leu Ile Glu Ile Ile Ser Leu
            20                  25                  30

Asp Phe Asp Gln Asn
        35

<210> SEQ ID NO 19
<211> LENGTH: 20
<212> TYPE: PRT
<213> ORGANISM: Homo sapiens

<400> SEQUENCE: 19

Leu Phe Gly Phe Leu Cys Glu Val Leu Arg Phe Gln Thr Phe Leu Leu
1               5                   10                  15

Glu Asn Ala Phe
            20

<210> SEQ ID NO 20
<211> LENGTH: 4
<212> TYPE: PRT
<213> ORGANISM: Homo sapiens

<400> SEQUENCE: 20

Asn Asn Phe Leu
1

<210> SEQ ID NO 21
<211> LENGTH: 12
<212> TYPE: PRT
<213> ORGANISM: Homo sapiens

<400> SEQUENCE: 21

Leu Pro Asp Val Asn Cys Leu Val Ile Ser Gly Tyr
1               5                   10

<210> SEQ ID NO 22
<211> LENGTH: 26
<212> TYPE: PRT
<213> ORGANISM: Homo sapiens

<400> SEQUENCE: 22

Asn Ile Gln Asn Val Gln Arg Val Gly Ser Gly Glu Cys Phe His Asp
1               5                   10                  15

Val Val Arg Pro Ala Gly Ala Gly Leu Gln
            20                  25

<210> SEQ ID NO 23
<211> LENGTH: 15
<212> TYPE: PRT
<213> ORGANISM: Homo sapiens

<400> SEQUENCE: 23

Thr Trp Thr Ser Glu Ala Ile Ile Ser Val His Ile Gly Thr Ile
1               5                   10                  15

<210> SEQ ID NO 24
<211> LENGTH: 7
<212> TYPE: PRT
<213> ORGANISM: Homo sapiens

<400> SEQUENCE: 24

Thr Ala Asp Gln Gly Cys Phe
1               5

```
<210> SEQ ID NO 25
<211> LENGTH: 10
<212> TYPE: PRT
<213> ORGANISM: Homo sapiens

<400> SEQUENCE: 25

Phe Gly Gly Thr Thr Ser Asn Tyr Ser Leu
1               5                   10

<210> SEQ ID NO 26
<211> LENGTH: 27
<212> TYPE: PRT
<213> ORGANISM: Homo sapiens

<400> SEQUENCE: 26

Gly Leu Glu Ala Val Glu Met Gln Ala Glu Ala Gln Lys Phe Tyr Gln
1               5                   10                  15

Tyr Gly Leu Ser Leu Ser Ile Pro Ser Val His
            20                  25

<210> SEQ ID NO 27
<211> LENGTH: 6
<212> TYPE: PRT
<213> ORGANISM: Homo sapiens

<400> SEQUENCE: 27

Val Cys Gly Asn Phe Leu
1               5

<210> SEQ ID NO 28
<211> LENGTH: 6
<212> TYPE: PRT
<213> ORGANISM: Homo sapiens

<400> SEQUENCE: 28

Asn Thr Lys Ser Tyr Arg
1               5

<210> SEQ ID NO 29
<211> LENGTH: 9
<212> TYPE: PRT
<213> ORGANISM: Homo sapiens

<400> SEQUENCE: 29

Arg Met Ala Lys Asn Ser Val Gln Pro
1               5

<210> SEQ ID NO 30
<211> LENGTH: 8
<212> TYPE: PRT
<213> ORGANISM: Homo sapiens

<400> SEQUENCE: 30

Arg Asn Val Arg Gly Gly Gly Gln
1               5

<210> SEQ ID NO 31
<211> LENGTH: 24
<212> TYPE: PRT
<213> ORGANISM: Homo sapiens

<400> SEQUENCE: 31

Ala Gly Glu Glu Tyr Gln His Ile Leu Gln Ala Pro Leu Cys Glu Arg
1               5                   10                  15

Val Pro Met Trp Trp Leu Leu Gln
```

<210> SEQ ID NO 32
<211> LENGTH: 18
<212> TYPE: PRT
<213> ORGANISM: Homo sapiens

<400> SEQUENCE: 32

Arg Glu Leu Tyr Val Tyr Glu His Gln His Leu Val His Phe Gln Thr
1               5                   10                  15

Ala Leu

<210> SEQ ID NO 33
<211> LENGTH: 9
<212> TYPE: PRT
<213> ORGANISM: Homo sapiens

<400> SEQUENCE: 33

Asp Ile Ser Ala Phe Asp Ile Ser Thr
1               5

<210> SEQ ID NO 34
<211> LENGTH: 4
<212> TYPE: PRT
<213> ORGANISM: Homo sapiens

<400> SEQUENCE: 34

Ile Ser Ala Cys
1

<210> SEQ ID NO 35
<211> LENGTH: 7
<212> TYPE: PRT
<213> ORGANISM: Homo sapiens

<400> SEQUENCE: 35

Ser Cys Gln Ser Tyr Arg Leu
1               5

<210> SEQ ID NO 36
<211> LENGTH: 20
<212> TYPE: PRT
<213> ORGANISM: Homo sapiens

<400> SEQUENCE: 36

Val Leu Ala Asn Ser Pro Pro Ser Ile Leu Asn Tyr Gln Lys Ile
1               5                   10                  15

His Pro Asp Pro
            20

<210> SEQ ID NO 37
<211> LENGTH: 13
<212> TYPE: PRT
<213> ORGANISM: Homo sapiens

<400> SEQUENCE: 37

Arg Arg Ser Leu Phe Pro Phe Gln Glu Thr Leu Ser Tyr
1               5                   10

<210> SEQ ID NO 38
<211> LENGTH: 4
<212> TYPE: PRT
<213> ORGANISM: Homo sapiens

<400> SEQUENCE: 38

```
His Ala Met Gly
1

<210> SEQ ID NO 39
<211> LENGTH: 30
<212> TYPE: PRT
<213> ORGANISM: Homo sapiens

<400> SEQUENCE: 39

Met Cys Phe Ala Gly Gly Lys Ser Thr Cys Trp Asn Arg Pro Leu
1               5                   10                  15

Ser Ser Pro Gly Thr Ser Ser Leu Trp Ala Thr His Asp Val
            20                  25                  30

<210> SEQ ID NO 40
<211> LENGTH: 8
<212> TYPE: PRT
<213> ORGANISM: Homo sapiens

<400> SEQUENCE: 40

Arg Arg Ser Leu Arg Val Cys Leu
1               5

<210> SEQ ID NO 41
<211> LENGTH: 17
<212> TYPE: PRT
<213> ORGANISM: Homo sapiens

<400> SEQUENCE: 41

Asn Thr Met Ser Gln Arg Ser Asn Pro Ala Pro Gln Lys Leu Gln Leu
1               5                   10                  15

Leu

<210> SEQ ID NO 42
<211> LENGTH: 22
<212> TYPE: PRT
<213> ORGANISM: Homo sapiens

<400> SEQUENCE: 42

Val Gln Arg Lys Ser Gly Asp Leu Leu Pro Glu Ala Gln Ala Ile Ser
1               5                   10                  15

Pro Arg His Leu Gln Leu
            20

<210> SEQ ID NO 43
<211> LENGTH: 118
<212> TYPE: PRT
<213> ORGANISM: Homo sapiens

<400> SEQUENCE: 43

Gly Gln Met Pro Leu Ser Tyr Gln Thr Met Cys Lys Trp Gln Asn Ser
1               5                   10                  15

Met Cys Lys Ala Leu Pro Leu Ser Lys Gly Glu Lys Gly Cys Pro Gly
            20                  25                  30

Ala Pro Gln Pro Lys Glu Ser Leu Ile Gln Arg Ser Lys Phe Pro Ile
        35                  40                  45

Pro Val Ile Phe Asn Ser Met Leu Leu Cys Gln Val Ala Val Thr Val
    50                  55                  60

Phe Phe Pro Gly Val Lys Lys Lys Ile His Phe Thr Gln His His Ser
65                  70                  75                  80

Glu Ser Arg Pro Thr Phe His Ser His Gln Leu Arg Ser Pro Trp Phe
```

```
                    85                  90                  95
Ile Asp Gly Cys Leu Leu Ala Ala Asp Ala Ser Ala His Gln Gly Met
            100                 105                 110

Glu Arg Arg Gly Pro Met
        115

<210> SEQ ID NO 44
<211> LENGTH: 12
<212> TYPE: PRT
<213> ORGANISM: Homo sapiens

<400> SEQUENCE: 44

Ser Phe Cys Leu Val Leu Phe Leu Phe Phe Gly Glu
1               5                   10

<210> SEQ ID NO 45
<211> LENGTH: 12
<212> TYPE: PRT
<213> ORGANISM: Homo sapiens

<400> SEQUENCE: 45

Glu Arg Cys Ala Gly His Gly Met Ala Gly Val Ile
1               5                   10

<210> SEQ ID NO 46
<211> LENGTH: 6
<212> TYPE: PRT
<213> ORGANISM: Homo sapiens

<400> SEQUENCE: 46

Leu Ile Thr Gln Ser Arg
1               5

<210> SEQ ID NO 47
<211> LENGTH: 21
<212> TYPE: PRT
<213> ORGANISM: Homo sapiens

<400> SEQUENCE: 47

Ser Leu Ser Pro Leu Leu Ile Ala Thr Leu Val Asn Tyr Ser Asp Ser
1               5                   10                  15

Phe Leu Cys Arg Ile
            20

<210> SEQ ID NO 48
<211> LENGTH: 5
<212> TYPE: PRT
<213> ORGANISM: Homo sapiens

<400> SEQUENCE: 48

Ser Val Leu Thr Phe
1               5

<210> SEQ ID NO 49
<211> LENGTH: 5
<212> TYPE: PRT
<213> ORGANISM: Homo sapiens

<400> SEQUENCE: 49

Leu Leu Ser Ser Leu
1               5

<210> SEQ ID NO 50
<211> LENGTH: 13
```

<210> SEQ ID NO 50
<211> LENGTH: 11
<212> TYPE: PRT
<213> ORGANISM: Homo sapiens

<400> SEQUENCE: 50

Ser Ser Ser Leu Met Asn Tyr His Leu Met Phe His Ile
1               5                   10

<210> SEQ ID NO 51
<211> LENGTH: 13
<212> TYPE: PRT
<213> ORGANISM: Homo sapiens

<400> SEQUENCE: 51

Val Tyr Leu Lys Lys Ile Asn Thr Ile Ile Gln Ala Ile
1               5                   10

<210> SEQ ID NO 52
<211> LENGTH: 4
<212> TYPE: PRT
<213> ORGANISM: Homo sapiens

<400> SEQUENCE: 52

Lys Lys Lys Lys
1

<210> SEQ ID NO 53
<211> LENGTH: 1864
<212> TYPE: DNA
<213> ORGANISM: Homo sapiens
<220> FEATURE:
<221> NAME/KEY: CDS
<222> LOCATION: (2)..(1861)
<223> OTHER INFORMATION: Alternate reading frame

<400> SEQUENCE: 53

| | | |
|---|---|---|
| g gca cga ggt ttt ttt ttt ttt ttt tca tct ctc tct ccc cac ccc taa<br>  Ala Arg Gly Phe Phe Phe Phe Phe Ser Ser Leu Ser Pro His Pro<br>       1               5                   10                  15 | | 49 |
| gat tgt gca aaa aaa gcg tac ctt gcc taa ttg aaa taa ttt cat tgg<br>Asp Cys Ala Lys Lys Ala Tyr Leu Ala     Leu Lys     Phe His Trp<br>               20                  25 | | 97 |
| att ttg atc aga act gat tat ttg gtt ttc tgt gtg aag ttt tga ggt<br>Ile Leu Ile Arg Thr Asp Tyr Leu Val Phe Cys Val Lys Phe     Gly<br>30                  35                  40 | | 145 |
| ttc aaa ctt tcc ttc tgg aga atg cct ttt gaa aca att ttc tct agc<br>Phe Lys Leu Ser Phe Trp Arg Met Pro Phe Glu Thr Ile Phe Ser Ser<br>45                  50                  55                  60 | | 193 |
| tgc ctg atg tca act gct tag taa tca gtg gat att gaa ata ttc aaa<br>Cys Leu Met Ser Thr Ala         Ser Val Asp Ile Glu Ile Phe Lys<br>               65                      70 | | 241 |
| atg tac aga gag tgg gta gtg gtg aat gtt ttc atg atg ttg tac gtc<br>Met Tyr Arg Glu Trp Val Val Val Asn Val Phe Met Met Leu Tyr Val<br>75                  80                  85                  90 | | 289 |
| cag ctg gtg cag ggc tcc agt aat gaa cat gga cca gtg aag cga tca<br>Gln Leu Val Gln Gly Ser Ser Asn Glu His Gly Pro Val Lys Arg Ser<br>               95                  100                 105 | | 337 |
| tct cag tcc aca ttg gaa cga tct gaa cag cag atc agg gct gct tct<br>Ser Gln Ser Thr Leu Glu Arg Ser Glu Gln Gln Ile Arg Ala Ala Ser<br>               110                 115                 120 | | 385 |
| agt ttg gag gaa cta ctt cga att act cac tct gag gac tgg aag ctg<br>Ser Leu Glu Glu Leu Leu Arg Ile Thr His Ser Glu Asp Trp Lys Leu<br>           125                 130                 135 | | 433 |
| tgg aga tgc agg ctg agg ctc aaa agt ttt acc agt atg gac tct cgc<br>Trp Arg Cys Arg Leu Arg Leu Lys Ser Phe Thr Ser Met Asp Ser Arg | | 481 |

```
              140                 145                 150
tca gca tcc cat cgg tcc act agg ttt gcg gca act ttc tat gac att    529
Ser Ala Ser His Arg Ser Thr Arg Phe Ala Ala Thr Phe Tyr Asp Ile
155                 160                 165                 170 gaa aca cta aaa gtt ata gat gaa gaa tgg caa aga act cag tgc agc    577
Glu Thr Leu Lys Val Ile Asp Glu Glu Trp Gln Arg Thr Gln Cys Ser
            175                 180                 185 cct aga gaa acg tgc gtg gag gtg gcc agt gag ctg ggg aag agt acc    625
Pro Arg Glu Thr Cys Val Glu Val Ala Ser Glu Leu Gly Lys Ser Thr
        190                 195                 200 aac aca ttc ttc aag ccc cct tgt gtg aac gtg ttc cga tgt ggt ggt    673
Asn Thr Phe Phe Lys Pro Pro Cys Val Asn Val Phe Arg Cys Gly Gly
            205                 210                 215 tgt tgc aat gaa gag agc ttt atg tgt atg aac acc agc acc tcg tac    721
Cys Cys Asn Glu Glu Ser Phe Met Cys Met Asn Thr Ser Thr Ser Tyr
    220                 225                 230 att tcc aaa cag ctc ttt gag ata tca gtg cct ttg aca tca gta cct    769
Ile Ser Lys Gln Leu Phe Glu Ile Ser Val Pro Leu Thr Ser Val Pro
235                 240                 245                 250 gaa tta gtg cct gtt aaa gtt gcc aat cat aca ggt tgt aag tgc ttg    817
Glu Leu Val Pro Val Lys Val Ala Asn His Thr Gly Cys Lys Cys Leu
                255                 260                 265 cca aca gcc ccc cgc cat cca tac tca att atc aga aga tcc atc cag    865
Pro Thr Ala Pro Arg His Pro Tyr Ser Ile Ile Arg Arg Ser Ile Gln
            270                 275                 280 atc cct gaa gaa gat cgc tgt tcc cat tcc aag aaa ctc tgt cct att    913
Ile Pro Glu Glu Asp Arg Cys Ser His Ser Lys Lys Leu Cys Pro Ile
        285                 290                 295 gac atg cta tgg gat agc aac aaa tgt aaa tgt gtt ttg cag gag gaa    961
Asp Met Leu Trp Asp Ser Asn Lys Cys Lys Cys Val Leu Gln Glu Glu
    300                 305                 310 aat cca ctt gct gga aca gaa gac cac tct cat ctc cag gaa cca gct    1009
Asn Pro Leu Ala Gly Thr Glu Asp His Ser His Leu Gln Glu Pro Ala
315                 320                 325                 330 ctc tgt ggg cca cac atg atg ttt gac gaa gat cgt tgc gag tgt gtc    1057
Leu Cys Gly Pro His Met Met Phe Asp Glu Asp Arg Cys Glu Cys Val
                335                 340                 345 tgt aaa aca cca tgt ccc aaa gat cta atc cag cac ccc aaa aac tgc    1105
Cys Lys Thr Pro Cys Pro Lys Asp Leu Ile Gln His Pro Lys Asn Cys
            350                 355                 360 agt tgc ttt gag tgc aaa gaa agt ctg gag acc tgc tgc cag aag cac    1153
Ser Cys Phe Glu Cys Lys Glu Ser Leu Glu Thr Cys Cys Gln Lys His
        365                 370                 375 aag cta ttt cac cca gac acc tgc agc tgt gag gac aga tgc ccc ttt    1201
Lys Leu Phe His Pro Asp Thr Cys Ser Cys Glu Asp Arg Cys Pro Phe
    380                 385                 390 cat acc aga cca tgt gca agt ggc aaa aca gca tgt gca aag cat tgc    1249
His Thr Arg Pro Cys Ala Ser Gly Lys Thr Ala Cys Ala Lys His Cys
395                 400                 405                 410 cgc ttt cca aag gag aaa agg gct gcc cag ggg ccc cac agc cga aag    1297
Arg Phe Pro Lys Glu Lys Arg Ala Ala Gln Gly Pro His Ser Arg Lys
                415                 420                 425 aat cct tga ttc agc gtt cca gtc cca tcc ctg tca ttt tta aca       1345
Asn Pro     Phe Ser Val Pro Ser Pro Ser Leu Ser Phe Leu Thr
                430                 435                 440 gca tgc tgc ttt gcc aag ttg ctg tca ctg ttt ttt tcc cag gtg tta    1393
Ala Cys Cys Phe Ala Lys Leu Leu Ser Leu Phe Phe Ser Gln Val Leu
            445                 450                 455 aaa aaa aaa tcc att tta cac agc acc aca gtg aat cca gac caa cct    1441
Lys Lys Lys Ser Ile Leu His Ser Thr Thr Val Asn Pro Asp Gln Pro
```

```
                   460                 465                 470
tcc att cac acc agc taa gga gtc cct ggt tca ttg atg gat gtc ttc      1489
Ser Ile His Thr Ser     Gly Val Pro Gly Ser Leu Met Asp Val Phe
475                 480                 485 tag ctg cag atg cct ctg cgc acc aag gaa tgg aga gga ggg gac cca      1537
    Leu Gln Met Pro Leu Arg Thr Lys Glu Trp Arg Gly Gly Asp Pro
        490                 495                 500 tgt aat cct ttt gtt tag ttt tgt ttt tgt ttt ttg gtg aat gag aaa      1585
Cys Asn Pro Phe Val     Phe Cys Phe Cys Phe Leu Val Asn Glu Lys
505                 510                 515 ggt gtg ctg gtc atg gaa tgg cag gtc tca tat gac tga tta ctc aga      1633
Gly Val Leu Val Met Glu Trp Gln Val Ser Tyr Asp     Leu Leu Arg
520                 525                 530 gca gat gag gaa aac tgt agt ctc tga gtc ctt tgc taa tcg caa ctc      1681
Ala Asp Glu Glu Asn Cys Ser Leu     Val Leu Cys     Ser Gln Leu
535                 540                 545 ttg tga att att ctg att ctt ttt tat gca gaa ttt gat tcg tat gat      1729
Leu     Ile Ile Leu Ile Leu Phe Tyr Ala Glu Phe Asp Ser Tyr Asp
            550                 555                 560 cag tac tga ctt tct gat tac tgt cca gct tat agt ctt cca gtt taa      1777
Gln Tyr     Leu Ser Asp Tyr Cys Pro Ala Tyr Ser Leu Pro Val
            565                 570                 575 tga act acc atc tga tgt ttc ata ttt aag tgt att taa aga aaa taa      1825
    Thr Thr Ile     Cys Phe Ile Phe Lys Cys Ile     Arg Lys
                    580                 585 aca cca tta ttc aag cca tat aaa aaa aaa aaa aaa                      1864
Thr Pro Leu Phe Lys Pro Tyr Lys Lys Lys Lys Lys
590                 595                 600

<210> SEQ ID NO 54
<211> LENGTH: 15
<212> TYPE: PRT
<213> ORGANISM: Homo sapiens

<400> SEQUENCE: 54

Ala Arg Gly Phe Phe Phe Phe Phe Ser Ser Leu Ser Pro His Pro
1               5                   10                  15

<210> SEQ ID NO 55
<211> LENGTH: 9
<212> TYPE: PRT
<213> ORGANISM: Homo sapiens

<400> SEQUENCE: 55

Asp Cys Ala Lys Lys Ala Tyr Leu Ala
1               5

<210> SEQ ID NO 56
<211> LENGTH: 17
<212> TYPE: PRT
<213> ORGANISM: Homo sapiens

<400> SEQUENCE: 56

Phe His Trp Ile Leu Ile Arg Thr Asp Tyr Leu Val Phe Cys Val Lys
1               5                   10                  15

Phe

<210> SEQ ID NO 57
<211> LENGTH: 23
<212> TYPE: PRT
<213> ORGANISM: Homo sapiens

<400> SEQUENCE: 57
```

Gly Phe Lys Leu Ser Phe Trp Arg Met Pro Phe Glu Thr Ile Phe Ser
1               5                   10                  15

Ser Cys Leu Met Ser Thr Ala
            20

<210> SEQ ID NO 58
<211> LENGTH: 362
<212> TYPE: PRT
<213> ORGANISM: Homo sapiens

<400> SEQUENCE: 58

Ser Val Asp Ile Glu Ile Phe Lys Met Tyr Arg Glu Trp Val Val
1               5                   10                  15

Asn Val Phe Met Met Leu Tyr Val Gln Leu Val Gln Gly Ser Ser Asn
                20                  25                  30

Glu His Gly Pro Val Lys Arg Ser Gln Ser Thr Leu Glu Arg Ser
            35                  40                  45

Glu Gln Gln Ile Arg Ala Ala Ser Ser Leu Glu Glu Leu Leu Arg Ile
        50                  55                  60

Thr His Ser Glu Asp Trp Lys Leu Trp Arg Cys Arg Leu Arg Leu Lys
65                  70                  75                  80

Ser Phe Thr Ser Met Asp Ser Arg Ser Ala Ser His Arg Ser Thr Arg
                85                  90                  95

Phe Ala Ala Thr Phe Tyr Asp Ile Glu Thr Leu Lys Val Ile Asp Glu
            100                 105                 110

Glu Trp Gln Arg Thr Gln Cys Ser Pro Arg Glu Thr Cys Val Glu Val
        115                 120                 125

Ala Ser Glu Leu Gly Lys Ser Thr Asn Thr Phe Phe Lys Pro Pro Cys
130                 135                 140

Val Asn Val Phe Arg Cys Gly Gly Cys Cys Asn Glu Glu Ser Phe Met
145                 150                 155                 160

Cys Met Asn Thr Ser Thr Ser Tyr Ile Ser Lys Gln Leu Phe Glu Ile
                165                 170                 175

Ser Val Pro Leu Thr Ser Val Pro Glu Leu Val Pro Val Lys Val Ala
            180                 185                 190

Asn His Thr Gly Cys Lys Cys Leu Pro Thr Ala Pro Arg His Pro Tyr
        195                 200                 205

Ser Ile Ile Arg Arg Ser Ile Gln Ile Pro Glu Glu Asp Arg Cys Ser
210                 215                 220

His Ser Lys Lys Leu Cys Pro Ile Asp Met Leu Trp Asp Ser Asn Lys
225                 230                 235                 240

Cys Lys Cys Val Leu Gln Glu Glu Asn Pro Leu Ala Gly Thr Glu Asp
                245                 250                 255

His Ser His Leu Gln Glu Pro Ala Leu Cys Gly Pro His Met Met Phe
            260                 265                 270

Asp Glu Asp Arg Cys Glu Cys Val Cys Lys Thr Pro Cys Pro Lys Asp
        275                 280                 285

Leu Ile Gln His Pro Lys Asn Cys Ser Cys Phe Glu Cys Lys Glu Ser
        290                 295                 300

Leu Glu Thr Cys Cys Gln Lys His Lys Leu Phe His Pro Asp Thr Cys
305                 310                 315                 320

Ser Cys Glu Asp Arg Cys Pro Phe His Thr Arg Pro Cys Ala Ser Gly
                325                 330                 335

Lys Thr Ala Cys Ala Lys His Cys Arg Phe Pro Lys Glu Lys Arg Ala
            340                 345                 350

```
Ala Gln Gly Pro His Ser Arg Lys Asn Pro
        355                 360
```

```
<210> SEQ ID NO 59
<211> LENGTH: 50
<212> TYPE: PRT
<213> ORGANISM: Homo sapiens

<400> SEQUENCE: 59
```

```
Phe Ser Val Pro Ser Ser Pro Ser Leu Ser Phe Leu Thr Ala Cys Cys
1               5                   10                  15

Phe Ala Lys Leu Leu Ser Leu Phe Phe Ser Gln Val Leu Lys Lys Lys
            20                  25                  30

Ser Ile Leu His Ser Thr Thr Val Asn Pro Asp Gln Pro Ser Ile His
        35                  40                  45

Thr Ser
    50
```

```
<210> SEQ ID NO 60
<211> LENGTH: 10
<212> TYPE: PRT
<213> ORGANISM: Homo sapiens

<400> SEQUENCE: 60
```

```
Gly Val Pro Gly Ser Leu Met Asp Val Phe
1               5                   10
```

```
<210> SEQ ID NO 61
<211> LENGTH: 20
<212> TYPE: PRT
<213> ORGANISM: Homo sapiens

<400> SEQUENCE: 61
```

```
Leu Gln Met Pro Leu Arg Thr Lys Glu Trp Arg Gly Gly Asp Pro Cys
1               5                   10                  15

Asn Pro Phe Val
            20
```

```
<210> SEQ ID NO 62
<211> LENGTH: 22
<212> TYPE: PRT
<213> ORGANISM: Homo sapiens

<400> SEQUENCE: 62
```

```
Phe Cys Phe Cys Phe Leu Val Asn Glu Lys Gly Val Leu Val Met Glu
1               5                   10                  15

Trp Gln Val Ser Tyr Asp
            20
```

```
<210> SEQ ID NO 63
<211> LENGTH: 11
<212> TYPE: PRT
<213> ORGANISM: Homo sapiens

<400> SEQUENCE: 63
```

```
Leu Leu Arg Ala Asp Glu Glu Asn Cys Ser Leu
1               5                   10
```

```
<210> SEQ ID NO 64
<211> LENGTH: 4
<212> TYPE: PRT
<213> ORGANISM: Homo sapiens
```

-continued

```
<400> SEQUENCE: 64

Ser Gln Leu Leu
1

<210> SEQ ID NO 65
<211> LENGTH: 16
<212> TYPE: PRT
<213> ORGANISM: Homo sapiens

<400> SEQUENCE: 65

Ile Ile Leu Ile Leu Phe Tyr Ala Glu Phe Asp Ser Tyr Asp Gln Tyr
1               5                   10                  15

<210> SEQ ID NO 66
<211> LENGTH: 12
<212> TYPE: PRT
<213> ORGANISM: Homo sapiens

<400> SEQUENCE: 66

Leu Ser Asp Tyr Cys Pro Ala Tyr Ser Leu Pro Val
1               5                   10

<210> SEQ ID NO 67
<211> LENGTH: 7
<212> TYPE: PRT
<213> ORGANISM: Homo sapiens

<400> SEQUENCE: 67

Cys Phe Ile Phe Lys Cys Ile
1               5

<210> SEQ ID NO 68
<211> LENGTH: 12
<212> TYPE: PRT
<213> ORGANISM: Homo sapiens

<400> SEQUENCE: 68

Thr Pro Leu Phe Lys Pro Tyr Lys Lys Lys Lys Lys
1               5                   10

<210> SEQ ID NO 69
<211> LENGTH: 1864
<212> TYPE: DNA
<213> ORGANISM: Homo sapiens
<220> FEATURE:
<221> NAME/KEY: CDS
<222> LOCATION: (3)..(1862)
<223> OTHER INFORMATION: Alternate reading frame

<400> SEQUENCE: 69 gg cac gag gtt ttt ttt ttt ttt ttt cat ctc tct ctc ccc acc cct        47
   His Glu Val Phe Phe Phe Phe Phe His Leu Ser Leu Pro Thr Pro
   1               5                   10                  15 aag att gtg caa aaa aag cgt acc ttg cct aat tga aat aat ttc att       95
Lys Ile Val Gln Lys Lys Arg Thr Leu Pro Asn     Asn Asn Phe Ile
                20                  25                      30 gga ttt tga tca gaa ctg att att tgg ttt tct gtg tca agt ttt gag      143
Gly Phe     Ser Glu Leu Ile Ile Trp Phe Ser Val     Ser Phe Glu
                35                  40 gtt tca aac ttt cct tct gga gaa tgc ctt ttg aaa caa ttt tct cta      191
Val Ser Asn Phe Pro Ser Gly Glu Cys Leu Leu Lys Gln Phe Ser Leu
45                  50                  55                  60 gct gcc tga tgt caa ctg ctt agt aat cag tgg ata ttg aaa tat tca      239
Ala Ala     Cys Gln Leu Leu Ser Asn Gln Trp Ile Leu Lys Tyr Ser
                65                  70                  75
```

| | | |
|---|---|---|
| aaa tgt aca gag agt ggg tag tgg tga atg ttt tca tga tgt tgt acg<br>Lys Cys Thr Glu Ser Gly     Trp     Met Phe Ser     Cys Cys Thr<br>                80                                      85 | | 287 |
| tcc agc tgg tgc agg gct cca gta atg aac atg gac cag tga agc gat<br>Ser Ser Trp Cys Arg Ala Pro Val Met Asn Met Asp Gln     Ser Asp<br>     90                      95                       100 | | 335 |
| cat ctc agt cca cat tgg aac gat ctg aac agc aga tca ggg ctg ctt<br>His Leu Ser Pro His Trp Asn Asp Leu Asn Ser Arg Ser Gly Leu Leu<br>      105                    110                    115 | | 383 |
| cta gtt tgg agg aac tac ttc gaa tta ctc act ctg agg act gga agc<br>Leu Val Trp Arg Asn Tyr Phe Glu Leu Leu Thr Leu Arg Thr Gly Ser<br>120                  125                   130                  135 | | 431 |
| tgt gga gat gca ggc tga ggc tca aaa gtt tta cca gta tgg act ctc<br>Cys Gly Asp Ala Gly     Gly Ser Lys Val Leu Pro Val Trp Thr Leu<br>              140                       145                   150 | | 479 |
| gct cag cat ccc atc ggt cca cta ggt ttg cgg caa ctt tct atg aca<br>Ala Gln His Pro Ile Gly Pro Leu Gly Leu Arg Gln Leu Ser Met Thr<br>                155                    160                   165 | | 527 |
| ttg aaa cac taa aag tta tag atg aag aat ggc aaa gaa ctc agt gca<br>Leu Lys His     Lys Leu     Met Lys Asn Gly Lys Glu Leu Ser Ala<br>                     170                       175                   180 | | 575 |
| gcc cta gag aaa cgt gcg tgg agg tgg cca gtg agc tgg gga aga gta<br>Ala Leu Glu Lys Arg Ala Trp Arg Trp Pro Val Ser Trp Gly Arg Val<br>                  185                   190                   195 | | 623 |
| cca aca cat tct tca agc ccc ctt gtg tga acg tgt tcc gat gtg gtg<br>Pro Thr His Ser Ser Ser Pro Leu Val     Thr Cys Ser Asp Val Val<br>                  200                     205                   210 | | 671 |
| gtt gtt gca atg aag aga gct tta tgt gta tga aca cca gca cct cgt<br>Val Val Ala Met Lys Arg Ala Leu Cys Val     Thr Pro Ala Pro Arg<br>               215                    220                     225 | | 719 |
| aca ttt cca aac agc tct ttg aga tat cag tgc ctt tga cat cag tac<br>Thr Phe Pro Asn Ser Ser Leu Arg Tyr Gln Cys Leu     His Gln Tyr<br>               230                    235                     240 | | 767 |
| ctg aat tag tgc ctg tta aag ttg cca atc ata cag gtt gta agt gct<br>Leu Asn     Cys Leu Leu Lys Leu Pro Ile Ile Gln Val Val Ser Ala<br>                        245                   250                   255 | | 815 |
| tgc caa cag ccc ccc gcc atc cat act caa tta tca gaa gat cca tcc<br>Cys Gln Gln Pro Pro Ala Ile His Thr Gln Leu Ser Glu Asp Pro Ser<br>                  260                     265                   270 | | 863 |
| aga tcc ctg aag aag atc gct gtt ccc att cca aga aac tct gtc cta<br>Arg Ser Leu Lys Lys Ile Ala Val Pro Ile Pro Arg Asn Ser Val Leu<br>                 275                     280                   285 | | 911 |
| ttg aca tgc tat ggg ata gca aca aat gta aat gtg ttt tgc agg agg<br>Leu Thr Cys Tyr Gly Ile Ala Thr Asn Val Asn Val Phe Cys Arg Arg<br>        290                     295                   300 | | 959 |
| aaa atc cac ttg ctg gaa cag aag acc act ctc atc tcc agg aac cag<br>Lys Ile His Leu Leu Glu Gln Lys Thr Thr Leu Ile Ser Arg Asn Gln<br>305                  310                   315                   320 | | 1007 |
| ctc tct gtg ggc cac aca tga tgt ttg acg aag atc gtt gcg agt gtg<br>Leu Ser Val Gly His Thr     Cys Leu Thr Lys Ile Val Ala Ser Val<br>                 325                    330                   335 | | 1055 |
| tct gta aaa cac cat gtc cca aag atc taa tcc agc acc cca aaa act<br>Ser Val Lys His His Val Pro Lys Ile     Ser Ser Thr Pro Lys Thr<br>                 340                    345                    350 | | 1103 |
| gca gtt gct ttg agt gca aag aaa gtc tgg aga cct gct gcc aga agc<br>Ala Val Ala Leu Ser Ala Lys Lys Val Trp Arg Pro Ala Ala Arg Ser<br>                      355                    360                   365 | | 1151 |
| aca agc tat ttc acc cag aca cct gca gct gtg agg aca gat gcc cct<br>Thr Ser Tyr Phe Thr Gln Thr Pro Ala Ala Val Arg Thr Asp Ala Pro<br>                  370                        375                   380 | | 1199 |

-continued

```
ttc ata cca gac cat gtg caa gtg gca aaa cag cat gtg caa agc att      1247
Phe Ile Pro Asp His Val Gln Val Ala Lys Gln His Val Gln Ser Ile
        385                 390                 395 gcc gct ttc caa agg aga aaa ggg ctg ccc agg ggc ccc aca gcc gaa      1295
Ala Ala Phe Gln Arg Arg Lys Gly Leu Pro Arg Gly Pro Thr Ala Glu
400                 405                 410 aga atc ctt gat tca gcg ttc caa gtt ccc cat ccc tgt cat ttt taa      1343
Arg Ile Leu Asp Ser Ala Phe Gln Val Pro His Pro Cys His Phe
415                 420                 425 cag cat gct gct ttg cca agt tgc tgt cac tgt ttt ttt ccc agg tgt      1391
Gln His Ala Ala Leu Pro Ser Cys Cys His Cys Phe Phe Pro Arg Cys
430                 435                 440                 445 taa aaa aaa aat cca ttt tac aca gca cca cag tga atc cag acc aac      1439
    Lys Lys Asn Pro Phe Tyr Thr Ala Pro Gln     Ile Gln Thr Asn
                450                 455 ctt cca ttc aca cca gct aag gag tcc ctg gtt cat tga tgg atg tct      1487
Leu Pro Phe Thr Pro Ala Lys Glu Ser Leu Val His     Trp Met Ser
460                 465                 470 tct agc tgc aga tgc ctc tgc gca cca agg aat gga gag ggg acc         1535
Ser Ser Cys Arg Cys Leu Cys Ala Pro Arg Asn Gly Glu Glu Gly Thr
475                 480                 485                 490 cat gta atc ctt ttg ttt agt ttt gtt ttt gtt ttt tgg tga atg aga      1583
His Val Ile Leu Leu Phe Ser Phe Val Phe Val Phe Trp     Met Arg
                495                 500                 505 aag gtg tgc tgg tca tgg aat ggc agg tgt cat atg act gat tac tca      1631
Lys Val Cys Trp Ser Trp Asn Gly Arg Cys His Met Thr Asp Tyr Ser
                510                 515                 520 gag cag atg agg aaa act gta gtc tct gag tcc ttt gct aat cgc aac      1679
Glu Gln Met Arg Lys Thr Val Val Ser Glu Ser Phe Ala Asn Arg Asn
                525                 530                 535 tct tgt gaa tta ttc tga ttc ttt ttt atg cag aat ttg att cgt atg      1727
Ser Cys Glu Leu Phe     Phe Phe Phe Met Gln Asn Leu Ile Arg Met
            540                 545                 550 atc agt act gac ttt ctg att act gtc cag ctt ata gtc ttc cag ttt      1775
Ile Ser Thr Asp Phe Leu Ile Thr Val Gln Leu Ile Val Phe Gln Phe
            555                 560                 565 aat gaa cta cca tct gat gtt tca tat tta agt gta ttt aaa gaa aat      1823
Asn Glu Leu Pro Ser Asp Val Ser Tyr Leu Ser Val Phe Lys Glu Asn
            570                 575                 580 aaa cac cat tat tca agc cat ata aaa aaa aaa aaa aaa aa               1864
Lys His His Tyr Ser Ser His Ile Lys Lys Lys Lys Lys
585                 590                 595
```

<210> SEQ ID NO 70
<211> LENGTH: 26
<212> TYPE: PRT
<213> ORGANISM: Homo sapiens

<400> SEQUENCE: 70

```
His Glu Val Phe Phe Phe Phe His Leu Ser Leu Pro Thr Pro Lys
1               5                   10                  15

Ile Val Gln Lys Lys Arg Thr Leu Pro Asn
            20                  25
```

<210> SEQ ID NO 71
<211> LENGTH: 6
<212> TYPE: PRT
<213> ORGANISM: Homo sapiens

<400> SEQUENCE: 71

Asn Asn Phe Ile Gly Phe

<210> SEQ ID NO 72
<211> LENGTH: 9
<212> TYPE: PRT
<213> ORGANISM: Homo sapiens

<400> SEQUENCE: 72

Ser Glu Leu Ile Ile Trp Phe Ser Val
1               5

<210> SEQ ID NO 73
<211> LENGTH: 21
<212> TYPE: PRT
<213> ORGANISM: Homo sapiens

<400> SEQUENCE: 73

Ser Phe Glu Val Ser Asn Phe Pro Ser Gly Glu Cys Leu Leu Lys Gln
1               5                   10                  15

Phe Ser Leu Ala Ala
            20

<210> SEQ ID NO 74
<211> LENGTH: 19
<212> TYPE: PRT
<213> ORGANISM: Homo sapiens

<400> SEQUENCE: 74

Cys Gln Leu Leu Ser Asn Gln Trp Ile Leu Lys Tyr Ser Lys Cys Thr
1               5                   10                  15

Glu Ser Gly

<210> SEQ ID NO 75
<211> LENGTH: 16
<212> TYPE: PRT
<213> ORGANISM: Homo sapiens

<400> SEQUENCE: 75

Cys Cys Thr Ser Ser Trp Cys Arg Ala Pro Val Met Asn Met Asp Gln
1               5                   10                  15

<210> SEQ ID NO 76
<211> LENGTH: 39
<212> TYPE: PRT
<213> ORGANISM: Homo sapiens

<400> SEQUENCE: 76

Ser Asp His Leu Ser Pro His Trp Asn Asp Leu Asn Ser Arg Ser Gly
1               5                   10                  15

Leu Leu Leu Val Trp Arg Asn Tyr Phe Glu Leu Leu Thr Leu Arg Thr
            20                  25                  30

Gly Ser Cys Gly Asp Ala Gly
            35

<210> SEQ ID NO 77
<211> LENGTH: 29
<212> TYPE: PRT
<213> ORGANISM: Homo sapiens

<400> SEQUENCE: 77

Gly Ser Lys Val Leu Pro Val Trp Thr Leu Ala Gln His Pro Ile Gly
1               5                   10                  15

Pro Leu Gly Leu Arg Gln Leu Ser Met Thr Leu Lys His

<210> SEQ ID NO 78
<211> LENGTH: 34
<212> TYPE: PRT
<213> ORGANISM: Homo sapiens

<400> SEQUENCE: 78

Met Lys Asn Gly Lys Glu Leu Ser Ala Ala Leu Glu Lys Arg Ala Trp
1               5                   10                  15
Arg Trp Pro Val Ser Trp Gly Arg Val Pro Thr His Ser Ser Ser Pro
            20                  25                  30
Leu Val

<210> SEQ ID NO 79
<211> LENGTH: 16
<212> TYPE: PRT
<213> ORGANISM: Homo sapiens

<400> SEQUENCE: 79

Thr Cys Ser Asp Val Val Val Ala Met Lys Arg Ala Leu Cys Val
1               5                   10                  15

<210> SEQ ID NO 80
<211> LENGTH: 17
<212> TYPE: PRT
<213> ORGANISM: Homo sapiens

<400> SEQUENCE: 80

Thr Pro Ala Pro Arg Thr Phe Pro Asn Ser Ser Leu Arg Tyr Gln Cys
1               5                   10                  15
Leu

<210> SEQ ID NO 81
<211> LENGTH: 5
<212> TYPE: PRT
<213> ORGANISM: Homo sapiens

<400> SEQUENCE: 81

His Gln Tyr Leu Asn
1               5

<210> SEQ ID NO 82
<211> LENGTH: 83
<212> TYPE: PRT
<213> ORGANISM: Homo sapiens

<400> SEQUENCE: 82

Cys Leu Leu Lys Leu Pro Ile Ile Gln Val Val Ser Ala Cys Gln Gln
1               5                   10                  15
Pro Pro Ala Ile His Thr Gln Leu Ser Glu Asp Pro Ser Arg Ser Leu
            20                  25                  30
Lys Lys Ile Ala Val Pro Ile Pro Arg Asn Ser Val Leu Leu Thr Cys
        35                  40                  45
Tyr Gly Ile Ala Thr Asn Val Asn Val Phe Cys Arg Arg Lys Ile His
    50                  55                  60
Leu Leu Glu Gln Lys Thr Thr Leu Ile Ser Arg Asn Gln Leu Ser Val
65                  70                  75                  80
Gly His Thr

<210> SEQ ID NO 83

```
<211> LENGTH: 18
<212> TYPE: PRT
<213> ORGANISM: Homo sapiens

<400> SEQUENCE: 83

Cys Leu Thr Lys Ile Val Ala Ser Val Ser Lys His His Val Pro
1               5                   10                  15

Lys Ile

<210> SEQ ID NO 84
<211> LENGTH: 85
<212> TYPE: PRT
<213> ORGANISM: Homo sapiens

<400> SEQUENCE: 84

Ser Ser Thr Pro Lys Thr Ala Val Ala Leu Ser Ala Lys Lys Val Trp
1               5                   10                  15

Arg Pro Ala Ala Arg Ser Thr Ser Tyr Phe Thr Gln Thr Pro Ala Ala
                20                  25                  30

Val Arg Thr Asp Ala Pro Phe Ile Pro Asp His Val Gln Val Ala Lys
            35                  40                  45

Gln His Val Gln Ser Ile Ala Ala Phe Gln Arg Arg Lys Gly Leu Pro
        50                  55                  60

Arg Gly Pro Thr Ala Glu Arg Ile Leu Asp Ser Ala Phe Gln Val Pro
65                  70                  75                  80

His Pro Cys His Phe
                85

<210> SEQ ID NO 85
<211> LENGTH: 16
<212> TYPE: PRT
<213> ORGANISM: Homo sapiens

<400> SEQUENCE: 85

Gln His Ala Ala Leu Pro Ser Cys Cys His Cys Phe Phe Pro Arg Cys
1               5                   10                  15

<210> SEQ ID NO 86
<211> LENGTH: 10
<212> TYPE: PRT
<213> ORGANISM: Homo sapiens

<400> SEQUENCE: 86

Lys Lys Asn Pro Phe Tyr Thr Ala Pro Gln
1               5                   10

<210> SEQ ID NO 87
<211> LENGTH: 16
<212> TYPE: PRT
<213> ORGANISM: Homo sapiens

<400> SEQUENCE: 87

Ile Gln Thr Asn Leu Pro Phe Thr Pro Ala Lys Glu Ser Leu Val His
1               5                   10                  15

<210> SEQ ID NO 88
<211> LENGTH: 32
<212> TYPE: PRT
<213> ORGANISM: Homo sapiens

<400> SEQUENCE: 88

Trp Met Ser Ser Ser Cys Arg Cys Leu Cys Ala Pro Arg Asn Gly Glu
1               5                   10                  15
```

Glu Gly Thr His Val Ile Leu Leu Phe Ser Phe Val Phe Trp
            20                  25                  30

<210> SEQ ID NO 89
<211> LENGTH: 39
<212> TYPE: PRT
<213> ORGANISM: Homo sapiens

<400> SEQUENCE: 89

Met Arg Lys Val Cys Trp Ser Trp Asn Gly Arg Cys His Met Thr Asp
1               5                   10                  15

Tyr Ser Glu Gln Met Arg Lys Thr Val Val Ser Glu Ser Phe Ala Asn
            20                  25                  30

Arg Asn Ser Cys Glu Leu Phe
        35

<210> SEQ ID NO 90
<211> LENGTH: 55
<212> TYPE: PRT
<213> ORGANISM: Homo sapiens

<400> SEQUENCE: 90

Phe Phe Phe Met Gln Asn Leu Ile Arg Met Ile Ser Thr Asp Phe Leu
1               5                   10                  15

Ile Thr Val Gln Leu Ile Val Phe Gln Phe Asn Glu Leu Pro Ser Asp
            20                  25                  30

Val Ser Tyr Leu Ser Val Phe Lys Glu Asn Lys His His Tyr Ser Ser
        35                  40                  45

His Ile Lys Lys Lys Lys Lys
    50                  55

<210> SEQ ID NO 91
<211> LENGTH: 1864
<212> TYPE: DNA
<213> ORGANISM: Homo sapiens
<220> FEATURE:
<221> NAME/KEY: misc_feature
<222> LOCATION: (1)..(1864)
<223> OTHER INFORMATION: Reverse complement  - see Fig. 2

<400> SEQUENCE: 91
tttttttttt tttttttat atggcttgaa taatggtgtt tattttcttt aaatacactt      60
aaatatgaaa catcagatgg tagttcatta aactggaaga ctataagctg gacagtaatc    120
agaaagtcag tactgatcat acgaatcaaa ttctgcataa aaaagaatca gaataattca    180
caagagttgc gattagcaaa ggactcgag actacagttt tcctcatctg ctctgagtaa     240
tcagtcatat gacacctgcc attccatgac cagcacacct ttctcattca ccaaaaaaca    300
aaaacaaaac taaacaaaag gattacatgg gtcccctcct ctccattcct tggtgcgcag    360
aggcatctgc agctagaaga catccatcaa tgaaccaggg actccttagc tggtgtgaat    420
ggaaggttgg tctggattca ctgtggtgct gtgtaaaatg gatttttttt ttaacacctg    480
ggaaaaaaac agtgacagca acttggcaaa gcagcatgct gttaaaaatg acagggatgg    540
ggaacttgga acgctgaatc aaggattctt tcggctgtgg ggcccctggg cagccctttt    600
ctcctttgga aagcggcaat gctttgcaca tgctgttttg ccacttgcac atggtctggt    660
atgaaagggg catctgtcct cacagctgca ggtgtctggg tgaaatagct tgtgcttctg    720
gcagcaggtc tccagacttt ctttgcactc aaagcaactg cagttttggg ggtgctggat    780
tagatctttg ggacatggtg ttttacagac acactcgcaa cgatcttcgt caaacatcat    840

```
gtgtggccca cagagagctg gttcctggag atgagagtgg tcttctgttc cagcaagtgg    900
attttcctcc tgcaaaacac atttacattt gttgctatcc catagcatgt caataggaca    960
gagtttcttg gaatgggaac agcgatcttc ttcagggatc tggatggatc ttctgataat   1020
tgagtatgga tggcgggggg ctgttggcaa gcacttacaa cctgtatgat tggcaactt    1080 aacaggcact aattcaggta ctgatgtcaa aggcactgat atctcaaaga gctgtttgga   1140
aatgtacgag gtgctggtgt tcatacacat aaagctctct tcattgcaac aaccaccaca   1200
tcggaacacg ttcacacaag ggggcttgaa gaatgtgttg gtactcttcc ccagctcact   1260
ggccacctcc acgcacgttt ctctagggct gcactgagtt ctttgccatt cttcatctat   1320
aacttttagt gtttcaatgt catagaaagt tgccgcaaac ctagtggacc gatgggatgc   1380
tgagcgagag tccatactgg taaaacttt gagcctcagc ctgcatctcc acagcttcca   1440
gtcctcagag tgagtaattc gaagtagttc ctccaaacta gaagcagccc tgatctgctg   1500
ttcagatcgt tccaatgtgg actgagatga tcgcttcact ggtccatgtt cattactgga   1560
gccctgcacc agctggacgt acaacatcat gaaaacattc accactaccc actctctgta   1620 catttgaat atttcaatat ccactgatta ctaagcagtt gacatcaggc agctagagaa   1680
aattgtttca aaaggcattc tccagaagga aagtttgaaa cctcaaaact tcacacagaa   1740
aaccaaataa tcagttctga tcaaaatcca atgaaattat ttcaattagg caaggtacgc   1800
tttttttgca caatcttagg ggtggggaga gagagatgaa aaaaaaaaaa aaaaacctcg   1860
tgcc                                                                1864

<210> SEQ ID NO 92
<211> LENGTH: 12
<212> TYPE: PRT
<213> ORGANISM: Artificial Sequence
<220> FEATURE:
<223> OTHER INFORMATION: Synthetic consensus pattern of the PDGF family
      signature
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 92

Cys Val Xaa Xaa Xaa Arg Cys Xaa Gly Cys Cys Asn
1               5                   10
```

That which is claimed is:

1. An isolated nucleotide molecule selected from the group consisting of:
   (a) a cDNA comprising nucleotides 283 through 1356 of SEQ ID NO: 1; and
   (b) the cDNA encoding the protein comprising amino acid residues 1 through 358 of SEQ ID NO: 2.

2. The isolated nucleotide molecules of claim 1, further comprising vector nucleotide sequences.

3. An isolated host cell stably transformed with the nucleotide molecule of claim 2, said host cell being a bacterial cell, a yeast cell or a mammalian cell.

4. The isolated host cell of claim 3, wherein said host cell is a mammalian cell.

5. The isolated host cell of claim 4, wherein said mammalian cell is a fibroblast.

6. An isolated nucleotide molecule that comprises a nucleotide sequence having at least 90% sequence homology relative to the full length of nucleotides 283 through 1356 of SEQ ID NO: 1, wherein said nucleotide sequence is a cDNA.

7. An isolated nucleotide molecule encoding a full length protein having at least 95% homology to the protein encoded by amino acid residues 1 through 358 of SEQ ID NO: 2, wherein said nucleotide molecule is a cDNA.

8. An isolated nucleotide molecule encoding a protein comprising an amino acid sequence that differs from 1 to 10 amino acid residues from amino acid residues 1 through 358 of SEQ ID NO: 2, wherein said molecule is a cDNA.

9. An isolated nucleotide molecule, that is complementary to an isolated nucleotide molecule that is a cDNA encoding a protein comprising an amino acid sequence that differs from 1 to 10 amino acid residues from amino acid residues 1 through 358 of SEQ ID NO: 2.

10. The isolated nucleotide molecule of claim 6, further comprising vector nucleotide sequences.

11. An isolated host cell stably transformed with the nucleotide molecule of claim 10, said host cell being a bacterial cell, a yeast cell or a mammalian cell.

12. The isolated host cell of claim 11, wherein said host cell is a mammalian cell.

13. The isolated host cell of claim 12, wherein said mammalian cell is a fibroblast.

14. The isolated nucleotide molecule of claim 7, further comprising vector nucleotide sequences.

15. An isolated host cell stably transformed with the nucleotide molecule of claim 14, said host cell being a bacterial cell, a yeast cell or a mammalian cell.

16. The isolated host cell of claim 15, wherein said host cell is a mammalian cell.

17. The isolated host cell of claim 15, wherein said mammalian cell is a fibroblast.

18. The isolated nucleic acid molecule of claim 8, wherein expression of said nucleotide molecule is induced in c-fos (−/−) mammalian fibroblasts by transient transfection of exogenous c-fos.

19. The isolated nucleic acid molecule of claim 8, wherein over-expression of said nucleotide molecule in mammalian fibroblasts leads to transformation.

20. An isolated nucleotide molecule that is complementary to the full length of an isolated nucleotide molecule selected from the group consisting of:
 (a) a cDNA comprising nucleotides 283 through 1356 of SEQ ID NO: 1; and
 (b) a cDNA encoding the protein comprising amino acid residues 1 through 358 of SEQ ID NO: 2.

21. An isolated nucleotide molecule that is complementary to the full length of an isolated nucleotide molecule that is a cDNA that comprises a nucleotide sequence having at least 90% sequence homology relative to the full length of nucleotides 283 through 1356 of SEQ ID NO: 1.

22. An isolated nucleic acid comprising a nucleotide sequence that encodes amino acids 1 to 358 of SEQ ID NO: 2.

23. The isolated nucleic acid according to claim 22 that is a cDNA comprising nucleotides 283 through 1356 of SEQ ID NO: 1.

\* \* \* \* \*